United States Patent
Yeates et al.

(10) Patent No.: US 11,911,482 B2
(45) Date of Patent: Feb. 27, 2024

(54) SELF ASSEMBLING PROTEIN NANOPARTICLES AS CARRIER MOLECULES

(71) Applicant: The Regents of the University of California, Oakland, CA (US)

(72) Inventors: Todd Yeates, Agoura Hills, CA (US); Yen-Ting Lai, Allston, MA (US); Justin Miller, Los Angeles, CA (US); Phillip Nguyen, Ithaca, NY (US); Yashes Srinivasan, San Diego, CA (US); Nithin Dharmaraj, San Diego, CA (US); Scott Taylor, Los Angeles, CA (US); Andrew Liu, Monrovia, CA (US)

(73) Assignee: The Regents of the University of California, Oakland, CA (US)

( * ) Notice: Subject to any disclaimer, the term of this patent is extended or adjusted under 35 U.S.C. 154(b) by 650 days.

(21) Appl. No.: 17/002,571

(22) Filed: Aug. 25, 2020

(65) Prior Publication Data
US 2022/0062430 A1  Mar. 3, 2022

(51) Int. Cl.
*A61K 47/62* (2017.01)
*A61K 47/65* (2017.01)
*A61K 47/69* (2017.01)

(52) U.S. Cl.
CPC .............. *A61K 47/62* (2017.08); *A61K 47/65* (2017.08); *A61K 47/6929* (2017.08)

(58) Field of Classification Search
CPC ..... A61K 47/6929; A61K 47/65; A61K 47/62
See application file for complete search history.

(56) References Cited

U.S. PATENT DOCUMENTS

| 10,400,015 B2 * | 9/2019 | Kwong | C07K 14/005 |
| 11,459,360 B2 * | 10/2022 | Kwong | A61K 39/21 |
| 2005/0233473 A1 | 10/2005 | Cicero | |
| 2006/0078951 A1 | 4/2006 | Youn | |
| 2014/0303014 A1 * | 10/2014 | Kwong | C07K 14/001 530/300 |
| 2016/0000901 A1 * | 1/2016 | Blackburn | A61K 39/145 530/358 |
| 2016/0184443 A1 | 6/2016 | Lu | |
| 2016/0311859 A1 | 10/2016 | Jerala | |
| 2017/0233441 A1 * | 8/2017 | Kwong | C07K 14/005 424/188.1 |
| 2022/0196655 A1 | 6/2022 | Hodge | |

FOREIGN PATENT DOCUMENTS

| WO | 2013052015 | 4/2013 |
| WO | 2014124301 | 8/2014 |
| WO | 2016037154 | 3/2016 |
| WO | 2018170362 | 9/2018 |
| WO | 2018172447 | 9/2018 |
| WO | 2020220044 | 10/2020 |

OTHER PUBLICATIONS

Bowie et al., 1990, Science 247: 1306-1310.*
Wells, 1990, Biochemistry 29:8509-8517.*
Badieyan et al., Symmetry-Directed Self-Assembly of a Tetrahedral Protein Cage Mediated by de Novo-Designed Coiled Coils, Oct. 5, 2017, pp. 1888-1892, vol. 18, No. 19, Publisher: Chembiochem.
Kang et al., Developing an antibody-binding protein cage as a molecular recognition drug modular nanoplatform, Jul. 1, 2012, pp. 5423-5430, vol. 33, No. 21, Publisher: Biomaterials.
Lee et al., Self-Assembling Peptides and Their Application in the Treatment of Diseases, Nov. 21, 2019, p. 5850, vol. 20, No. 23, Publisher: Int J Mol Sci.
Majsterkiewicz et al., Connectability of protein cages, May 18, 2020, pp. 2255-2264, vol. 2, No. 6, Publisher: Nanoscale Adv.

* cited by examiner

*Primary Examiner* — Gyan Chandra
(74) *Attorney, Agent, or Firm* — Suzannah K. Sundby, Esq.; Canady + Lortz LLP

(57) ABSTRACT

Disclosed herein are self-assembling protein nanoparticles comprising passenger molecules of interest.

15 Claims, 18 Drawing Sheets

Specification includes a Sequence Listing.

```
       ***    ******  *     ****  **  ******* *  **    *  ** *********
MPFITVGQENSTSIDLYYEDHGTGTPVVLIHGFPLSGHSWERQSAALLDAGYRVITYDRRGFGQ
1                                                              64

*****  * ****** **        *     *****   ****       *****     *** ** *
SSQPTTGYDYDTFAADLNTVLETLDLQDAVLVGFSMGTGEVARYVSSYGTARIAAVAFLASLEP
                                                              128

#                          #
  *  *****  *  *    **  *    *******   *   ** *****************
FLLKTDDNPDGAAPQEFFDGIVAAVKADRYAFYTGFFNDFYNLDENLGTRISEEAVRNSWNTAA
                                                              192

#    #
* *****  ***    *  ****   *   *** **  *** ****    * *    **** *  *   **
SGGFFAAAAAPTTWYTDFRADIPRIDVPALILHGTGDRTLPIENTARVFHKALPSAEYVEVEGA
                                                              256

@@@@@@@@
                                                                      $^^
 *  ******   *  **  **    *        ********* *******  ***  *  ** *
PHGLLWTHAEEVNTALLAFLAKAQEAQKQKLLTEVETYVLSIIPSGPLKAEIAQRLEDVFAGKN
                                                              320

^$
  ***   *** ******* ****   ***  *************  **  *  **  ***** *** ** **
TDLEVLMEWLKTRPILSPLTKGILGFVFTLTVPSERGLQRRRFVQNALNGNGDPNNMDKAVKLY
                                                              384

$^^^^^^
******  *******     ** ***  ********  **  *  *  * **  ********
RKLKREITFHGAKEISLSYSAGALASCMGLIYNRMGAVTTEVAFGLVCATCEQIADSQHRSHRQ
                                                              448

$
LEHHHHHH
     456
```

FIG. 6

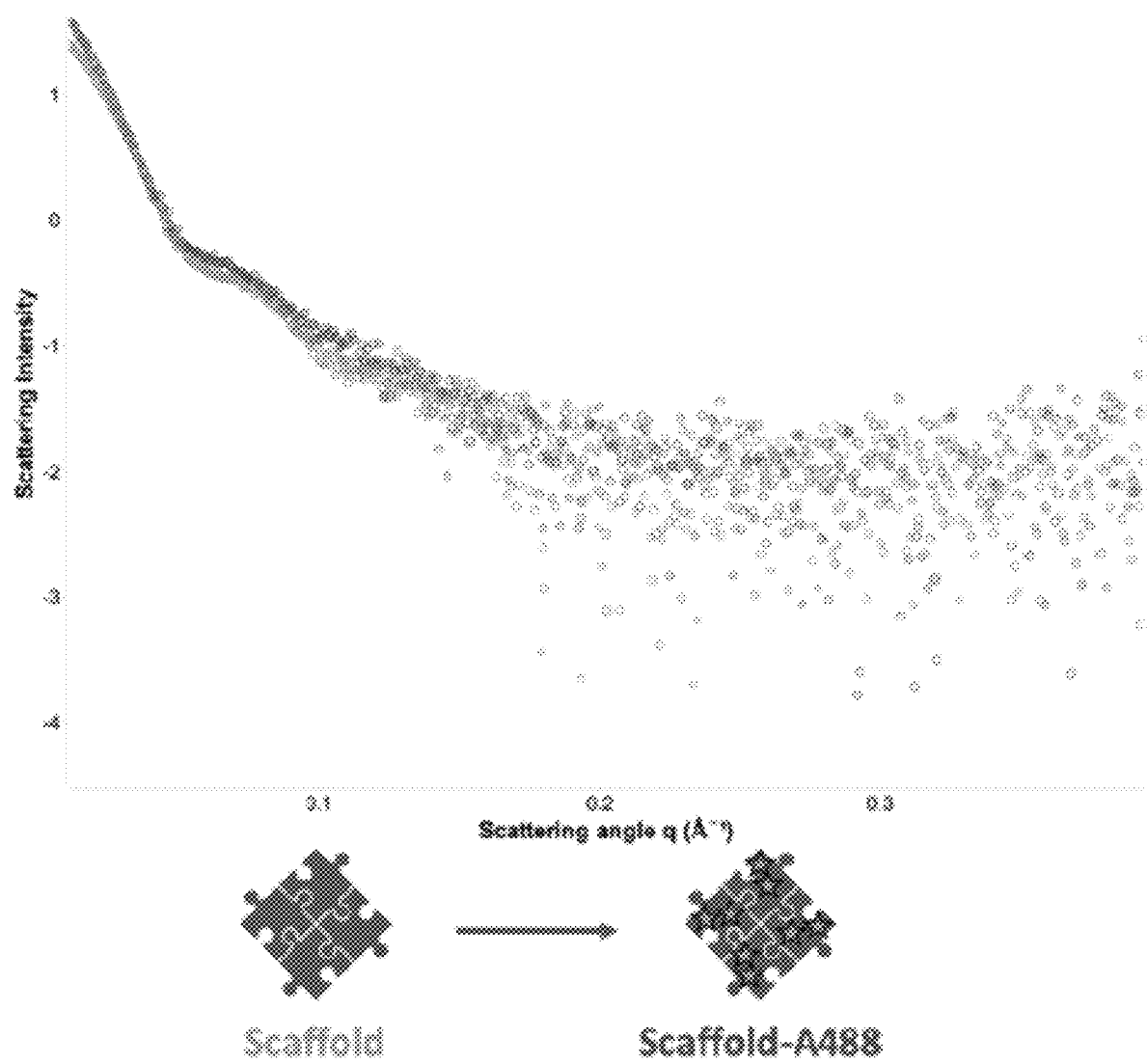
- Prototype maintains tetrahedral form
- Labeling with AlexaFluor-488 does not disrupt structure
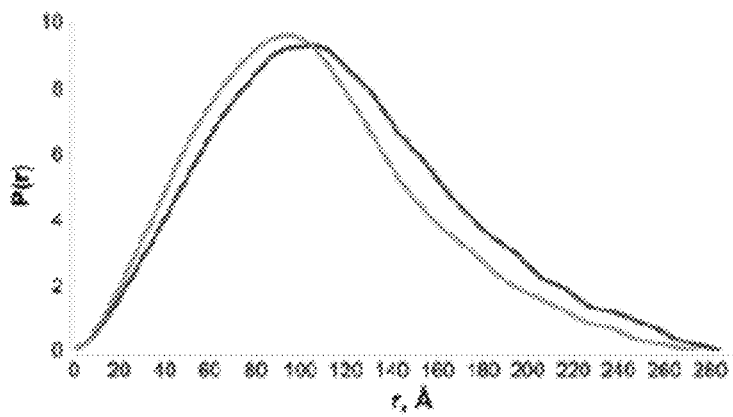
FIG. 12

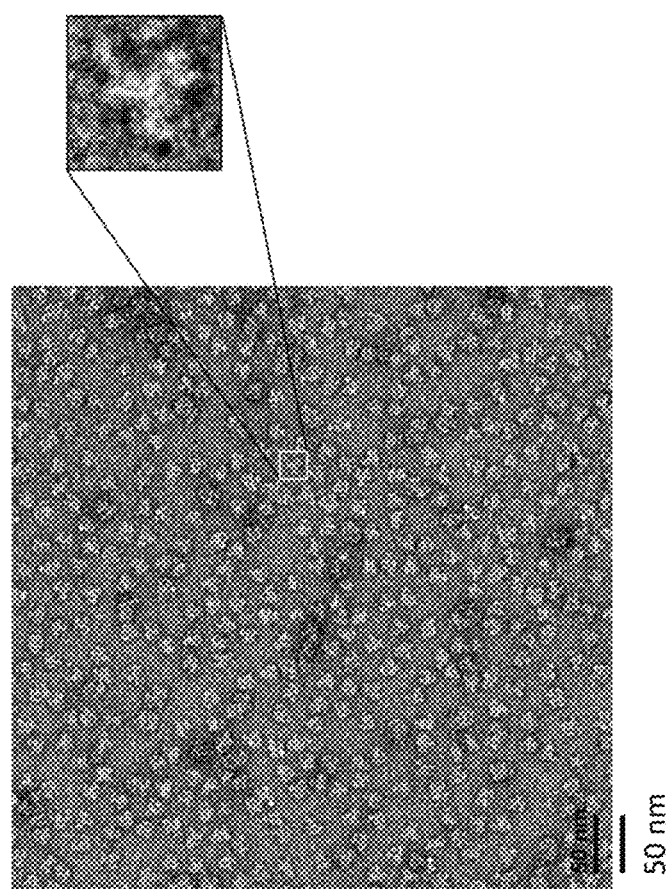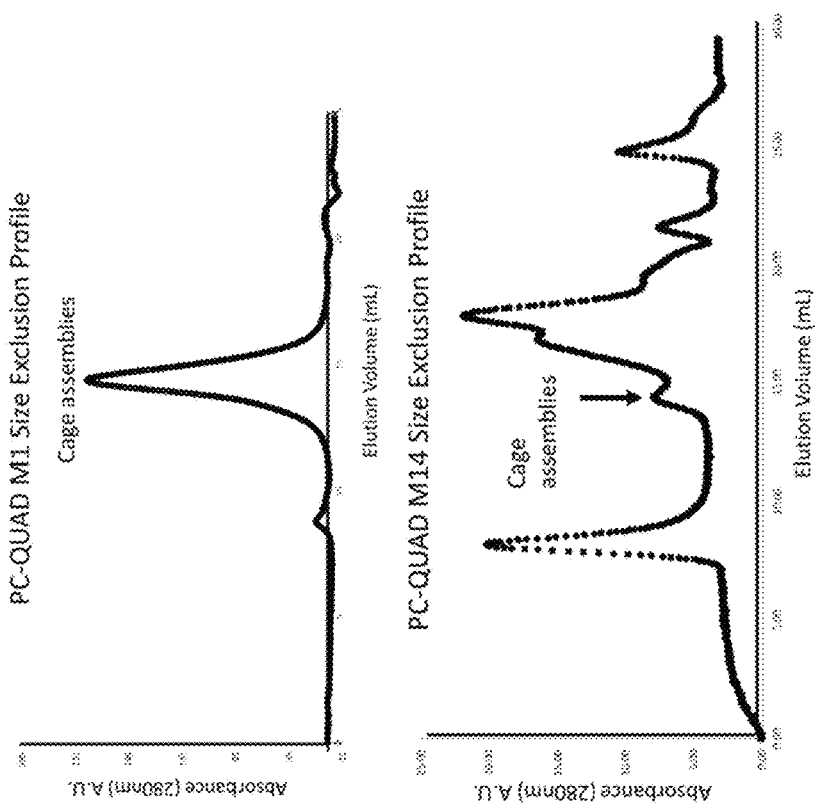
FIG. 17

SELF ASSEMBLING PROTEIN NANOPARTICLES AS CARRIER MOLECULES

RELATED APPLICATIONS

The application is related to the subject matter disclosed in PCT/US2020/030142, filed Apr. 27, 2020, which claims the benefit of U.S. Application No. 62/838,826, filed Apr. 25, 2019, both of which are herein incorporated by reference in their entirety.

REFERENCE TO A SEQUENCE LISTING SUBMITTED VIA EFS-WEB

The content of the ASCII text file of the sequence listing named "20200825_034044_222_ST25" which is 208 kb in size was created on Aug. 25, 2020 and electronically submitted via EFS-Web herewith the application is incorporated herein by reference in its entirety.

ACKNOWLEDGEMENT OF GOVERNMENT SUPPORT

This invention was made with Government support under 1332907, awarded by the National Science Foundation & DE-FC02-02ER63421 awarded by Department of Energy. The Government has certain rights in the invention.

FIELD OF THE INVENTION

The field of the invention generally relates to Self-Assembling Protein Nanoparticles (SAPN) and their use as carrier molecules for passenger molecules of interest.

BACKGROUND OF THE INVENTION

The global market for protein therapeutics exceeds $100 billion, with products treating diverse diseases through various modes of biological action. Proteins provide unmatched versatility in their specificity and function, enabling therapeutics that bind specific cellular targets and are reactive in ways that modulate health and disease. Antibodies, and components thereof, represent major areas of therapeutic focus, while other protein-based components provide additional opportunities for binding and interaction with cellular targets. A major current theme is the creation of polyvalent therapeutics with the capacity to interact with multiple cellular targets, often simultaneously; this enables more complex functions while also enabling stronger binding interactions. Therapeutics that are responsive—i.e., that alter their structure or reactivity—as a function of their interactions with cellular targets are likewise of major interest. Recent advances in protein design, especially in designing multi-subunit, self-assembling protein cages, have opened opportunities to create new types of polyvalent and responsive protein therapeutics. The market for this next generation of protein therapeutics is expected to be expansive.

U.S. Pat. No. 6,756,039 (Yeates, Padilla, and Colovos) discloses fusion proteins capable of self-assembling into regular structures, wherein the fusion proteins comprise at least two oligomerization domains rigidly linked together, e.g., through an alpha helical linking group.

U.S. Pat. No. 7,608,681 (Dennis, Lowman and DeLano) discloses peptide ligands with affinity for IgG or for serum albumin.

U.S. Pat. No. 8,969,521 (Baker, King, Sheffler and, Yeates) discloses a general method for designing self-assembling protein nanomaterials, and an isolated polypeptide, comprising a specific 184 amino acid sequence, capable of forming a multimeric assembly.

U.S. Patent Application Publication No. 20070218547 (Yeates, Padilla, Yoshida, and Colovos) discloses self-assembling proteins for producing extended materials, including a fusion protein comprising a first oligomerization domain that naturally associates into homodimeric structures and a second oligomerization domain that naturally associates into homotetrameric structures, wherein said first and second oligomerization domains are rigidly linked to each other.

SUMMARY OF THE INVENTION

In some embodiments, the present invention provides

Embodiment 1: A polypeptide comprising (a) a scaffolding protein which comprises an amino acid sequence having at least 90%, at least 91%, at least 92%, at least 93%, at least 94%, at least 95%, at least 96%, at least 97%, at least 98%, at least 99%, or 100% sequence identity to SEQ ID NO: 64, and (b) a given passenger peptide covalently linked thereto.

Embodiment 2: The polypeptide according to Embodiment 1, wherein the scaffolding protein further comprises CATCEQIAD (SEQ ID NO: 45).

Embodiment 3: The polypeptide according to Embodiment 1, wherein the scaffolding protein lacks CATCEQIAD (SEQ ID NO: 45).

Embodiment 4: The polypeptide according to any one of Embodiments 1-3, wherein the scaffolding protein further comprises a histidine tag such as EHHHHHH (SEQ ID NO: 52).

Embodiment 5: The polypeptide according to any one of Embodiments 1-4, wherein the scaffolding protein further comprises CATCEQIADSQHRSHRQLEHHHHHH (SEQ ID NO: 56).

Embodiment 6: The polypeptide according to any one of Embodiments 1-5, wherein the scaffolding protein comprises a sequence selected from the group consisting of: LTEVETYVLS (SEQ ID NO: 43), FTLTVPSERGLQR (SEQ ID NO: 44), AQEAQKQK (SEQ ID NO: 46), YGTAR (SEQ ID NO: 47), TDD (SEQ ID NO: 48), LXENLGTR (SEQ ID NO: 49), IDV (SEQ ID NO: 50), TGXRT (SEQ ID NO: 51), LVPRGSG (SEQ ID NO: 53), and GSENLYFQGGS (SEQ ID NO: 54).

Embodiment 7: The polypeptide according to any one of Embodiments 1-6, wherein the passenger peptide is covalently linked to an amino acid at an amino acid position selected from the group consisting of: residues 19-26, 131-141, 245-257, 300-304, and 350-357 of the scaffolding protein based on SEQ ID NO: 64 when optimally aligned thereto.

Embodiment 8: The polypeptide according to any one of Embodiments 1-6, wherein the passenger peptide replaces one or more amino acids at an amino acid position selected from the group consisting of: residues 19-26, 131-141, 245-257, 300-304, and 350-357 of the scaffolding protein based on SEQ ID NO: 64 when optimally aligned thereto.

Embodiment 9: The polypeptide according to any one of Embodiments 1-6, wherein the passenger peptide is covalently linked to or replaces an amino acid at an amino acid position selected from the group consisting of: residues 19, 20, 21, 22, 23, 24, 25, 26, 131, 132, 133, 134, 135, 136, 137, 138, 139, 140, 141, 245, 246, 247, 248, 249, 253, 254, 255, 256, 257, 300, 301, 302, 303, 304, 350, 351, 352, 353, 354, 355, 356, and 357 of the scaffolding protein based on SEQ ID NO: 64 when optimally aligned thereto.

Embodiment 10: The polypeptide according to any one of Embodiments 1-6, wherein the passenger peptide is covalently linked to or replaces an amino acid at an amino acid position selected from the group consisting of: residues 22, 23, 24, 25, 139, 238, 244, 245, 246, 301, 302, 303, 352, 353, 354, 355, and 356 of the scaffolding protein based on SEQ ID NO: 64 when optimally aligned thereto.

Embodiment 11: The polypeptide according to any one of Embodiments 1-10, wherein the passenger peptide neither comprises nor consists of SEQ ID NO: 41 or SEQ ID NO: 42.

Embodiment 12: The polypeptide according to any one of Embodiments 1-11, wherein the passenger peptide is cleaved by a protease.

Embodiment 13: The polypeptide according to any one of Embodiments 1-11, wherein the passenger peptide is a substrate for an enzyme.

Embodiment 14: The polypeptide according to Embodiment 12 or Embodiment 13, wherein the enzyme or protein is a protease such as thrombin or TEV protease.

Embodiment 15: The polypeptide according to any one of Embodiments 1-14, wherein the passenger peptide comprises LVPRGSG (SEQ ID NO: 53) or GSENLYFQGGS (SEQ ID NO: 54).

In some embodiments, the present invention provides for a protein cage polypeptide (or scaffolding protein) useful or capable of forming a hollow tetrahedral pyramid structure, wherein the protein cage polypeptide (i.e., the scaffolding protein or a passenger peptide covalently linked thereto is capable of binding specifically to an antibody or part thereof, or any chimeric protein, molecule or compound comprising the antibody, or part thereof.

In some embodiments, the antibody is an IgG antibody. In some embodiments, the part of the antibody is an Fc region of an antibody, such as an IgG, IgA, IgD, IgE, or IgM antibody. In some embodiments, the antibody is a human, chicken, mice, rabbit, sheep, or goat antibody. In some embodiments, the antibody is a humanized antibody. In some embodiments, the IgG antibody is a human IgG antibody. In some embodiments, the antibody is part of a chimeric protein, molecule or compound, comprising the antibody, or part thereof. In some embodiments, the chimeric protein, or other molecule or compound, comprises an Fc region of an antibody. In some embodiments, the antibody, or part thereof, is covalently bonded to the chimeric protein, molecule or compound. In some embodiments, the binding affinity $K_a$ of the protein cage polypeptide, or scaffolding protein, to the antibody or part thereof, is equal to or more than $10^7 M^{-1}$, $10^8 M^{-1}$, or $10^9 M^{-1}$.

In some embodiments, the protein cage polypeptide comprises a polypeptide of from about 400 to about 700 amino acid residues. In some embodiments, the protein cage polypeptide comprises a polypeptide of from about 450 to about 650 amino acid residues.

In some embodiments, the protein cage polypeptide comprises an amino acid sequence having the following structure:

Polypeptide 1-AHL-Polypeptide 2-INSERT A-Polypeptide 3-INSERT B-Polypeptide 4    (Chemical Structure I);

wherein AHL is an "alpha helix linker" and INSERT A and/or INSERT B are passenger polypeptides, which each independently capable of specifically binding to an antibody or part thereof.

In some embodiments, the INSERT A has a length of about 17 to about 25 amino acids. In some embodiments, the INSERT B has a length of about 28 to about 85 amino acids. In some embodiments, the binding affinity $K_a$ of INSERT A and/or INSERT B to the antibody or part thereof, are each independently equal to or more than $10^7 M^{-1}$, $10^8 M^{-1}$, or $10^9 M^{-1}$. In some embodiments, the INSERT A and/or INSERT B each independently comprise the amino acid sequence DCAWHLGELVWCT (SEQ ID NO: 41) or GCDCAWHLGELVWCTCG (SEQ ID NO: 42).

In some embodiments, the protein cage polypeptide comprises an amino acid sequence having the following structure:

Polypeptide 1-AHL-Polypeptide 2-INSERT A-Polypeptide 3-INSERT B-Polypeptide 4    (Chemical Structure I);

wherein AHL is an "alpha helix linker", INSERT A having a length of about 17 to about 25 amino acids and comprising the amino acid sequence DCAWHLGELVWCT (SEQ ID NO: 41) or GCDCAWHLGELVWCTCG (SEQ ID NO: 42), and INSERT B having a length of about 28 to about 85 amino acids and comprising the amino acid sequence DCAWHLGELVWCT (SEQ ID NO: 41) or GCDCAWHLGELVWCTCG (SEQ ID NO: 42). SEQ ID NOs:41 and 42 are capable of binding to the Fc-region of IgG.

In some embodiments, Polypeptide 1 comprises an amino acid sequence comprising at least about 70%, 75%, 80%, 85%, 90%, 95%, 99%, or 100% amino acid identity to the amino acid sequence from the N-terminus to up to AQEAQKQK (SEQ ID NO: 46) in any one of SEQ ID NOs: 1-40. In some embodiments, Polypeptide 1 comprises an amino acid sequence comprising the following: YGTAR (SEQ ID NO: 47), TDD (SEQ ID NO: 48), LXENLGTR (SEQ ID NO: 49), IDV (SEQ ID NO: 50), TGXRT (SEQ ID NO: 51), and/or SA; wherein X is any charged amino acid residue. In some embodiments, Polypeptide 1 comprises about 278 to about 303 amino acid residues.

In some embodiments, AHL comprises an amino acid sequence comprising: AQEAQKQK (SEQ ID NO: 46). In some embodiments, AHL comprises about 5, 6, 7, 8, 9, 10, or 11 amino acid residues.

In some embodiments, Polypeptide 2 comprises an amino acid sequence comprising at least about 70%, 75%, 80%, 85%, 90%, 95%, or 100% amino acid identity to the amino acid sequence from the C-end of AQEAQKQK (SEQ ID NO: 46) to the N-end of INSERT A of any one of SEQ ID NOs: 1-40. In some embodiments, Polypeptide 2 comprises an amino acid sequence comprising the following: LTEVETYVLS (SEQ ID NO: 43). In some embodiments, Polypeptide 2 comprises about 30 to about 36 amino acid residues. In some embodiments, Polypeptide 2 comprises about 33 amino acid residues.

In some embodiments, Polypeptide 3 comprises an amino acid sequence comprising at least about 70%, 75%, 80%, 85%, 90%, 95%, or 100% amino acid identity to the amino acid sequence from the C-end of INSERT A to the N-end of INSERT B of any one of SEQ ID NOs: 1-40. In some embodiments, Polypeptide 3 comprises an amino acid sequence comprising the following: FTLTVPSERGLQR (SEQ ID NO: 44) and/or CATCEQIAD (SEQ ID NO: 45). In some embodiments, Polypeptide 3 comprises about 110 to about 130 amino acid residues. In some embodiments, Polypeptide 3 comprises about 121 amino acid residues.

In some embodiments, Polypeptide 4 comprises an amino acid sequence comprising at least about 70%, 75%, 80%, 85%, 90%, 95%, or 100% amino acid identity to the amino acid sequence from the C-end of INSERT B of any one of SEQ ID NOs: 1-40. In some embodiments, Polypeptide 4 comprises an amino acid sequence comprising: EHHHHHH (SEQ ID NO: 52). In some embodiments, Polypeptide 4 comprises about 5 to about 13 amino acid residues. In some embodiments, Polypeptide 4 comprises about 8 amino acid residues.

In some embodiments, the protein cage polypeptide comprises an amino acid sequence with at least about 70%, 75%, 80%, 85%, 90%, 95%, 99%, or 100% amino acid identity to any one of SEQ ID NOs: 1-40. In some embodiments, the protein cage polypeptide comprises an amino acid sequence comprising any one or more, or all, stretches of or individual amino acid residues indicated by an asterisk in FIG. 6. In some embodiments, the protein cage polypeptide comprises an amino acid sequence comprising any one or more, or all, charged amino acids stretches in the corresponding position(s) indicated by "#" in FIG. 6.

The present invention provides for a hollow tetrahedral pyramid structure comprising twelve protein cage polypeptides of the present invention assembled as the hollow tetrahedral pyramid structure, wherein the protein cage polypeptide is capable of binding to an antibody or part thereof. In some embodiments, the hollow tetrahedral pyramid structure encapsulates one or more smaller molecules of interest. In some embodiments, the smaller molecules of interest are therapeutic or detectable. In some embodiments, the tetrahedral pyramid structure is disrupted by a protease, thereby releasing any passenger molecules encapsulated within the interior of the tetrahedral pyramid structure.

The present invention provides for a "self-assembling protein nanoparticle decorated with antibodies" (SAPNA) which is a chimeric protein assembly comprising: (a) one or more antibodies and (b) a protein cage polypeptide that provides a scaffold upon which to array the antibodies, wherein the one or more antibodies are bound to the INSERT A and/or INSERT B of the protein cage polypeptide.

The present invention provides for a SAPNA which is a chimeric protein assembly comprising: (a) one or more antibodies and (b) an engineered protein that provides a scaffold upon which to array the antibodies. The scaffolding protein forms hollow tetrahedral pyramids that can be assembled or disassembled based on buffer conditions. As the scaffold is hollow, the system can encapsulate smaller molecules of interest for release once the antibodies have localized the SAPNA to a target. These particles are engineered to modularly bind and display any IgG antibody (or Fc region only), such as a human or rabbit IgG antibody (or Fc region only), or fragment thereof, through a high-affinity interaction with the antibody Fc CH2/CH3 domains. The physically constrained localization of from 1, 2, 3, 4, 5, 6, 7, 8, 9, 10, 11, or 12 antibodies or Fc domains per nanoparticle allows activation of any oligomerization-dependent receptor-mediated pathways for which an antibody is available. In some embodiments, through separate loading and mixing, antibodies that recognize different epitopes can be loaded onto the same nanoparticle, conferring multi-functionality. In some embodiments, the nanoparticles can be used to stimulate innate or adaptive immune cells, as Fc receptor oligomerization is a necessary component of activation.

The present invention provides for a SAPNA structure comprising: (1) one protein cage polypeptide or scaffolding protein (or engineered protein cage protein (PC)), or a plurality of protein cage polypeptides or scaffolding proteins (or engineered protein cage proteins (PCs)) assembled into a 3-dimensional assembly, such as a tetrahedral pyramid, (2) optionally one or more human or rabbit IgG antibodies, (3) optionally an IgG binding loop, and (4) optionally, when the plurality of polypeptides or scaffolding proteins (or engineered protein cage proteins (PCs)) are assembled into a 3-dimensional assembly with antibodies, a cargo of interest, such as a compound or molecule, such as a macromolecule, confined or enclosed by the 3-dimensional assembly. One embodiment of the invention is shown in FIG. 1A.

The human IgG antibodies recognize and bind tightly to a variety of targets. In some embodiments, the targets are parts of pathogens. In some embodiments, the targets are native cellular components. In some embodiments, the IgG binding loop is a sequence of protein that is incorporating into the PC and serves as a connection between the antibody and the PC. The PC has had several publications devoted to it (1-3), however never with any context related to antibodies. Under most physiological conditions the PC component can self-assemble into a hollow tetrahedral pyramid from 12 copies of itself. In some embodiments, the SAPNA structure is capable of delivering or carrying cargo to wherever the SAPNA is localized by the antibodies. In some embodiments, the cargo size ranges between about 150 kDa and about 20 kDa. Many useful macromolecules fit this range.

SAPNA structures can be assembled and disassembled. This functionality can be used to initially capture cargo or release cargo. In addition, since there are many kinds of antibodies. PCs with a variety of antibodies can be mixed to create a SAPNA with a diverse set of antibodies on its surface. The capacity to interchange antibodies provides additional functionality.

In some embodiments, aside from a capacity to carry and localize cargo, SAPNAs can alter cellular behavior without cargo. External stimuli that affect cells often start from a ligand binding to bring transmembrane receptors into close contact (oligomerization).

This is achieved through the binding of two or more receptors to a ligand, such as a cytokine, however the ligands for many receptors are unknown, or could be restricted to the cell surface of another cell. In some embodiments, through display on the PC (FIG. 1A, B; FIG. 7), the functional power of any IgG antibody developed against any single receptor would be significantly enhanced. Instead of largely being limited to blocking the receptor, the antibody could activate the intracellular signaling pathway, resulting in much finer control of cellular activity. In some embodiments, different kinds of antibodies are displayed on the PC and the protein can influence signals that operate through multi-chain immune recognition receptors (MIRRs). Many immune cells rely on MIRRs for control of intracellular signaling. MIRRs often require multi-chain engagement by an extracellular ligand for oligomerization and subsequent activation. In some embodiments, the SAPNAs would modularly confer activation/signaling abilities to IgG antibodies that are currently limited to blocking mechanisms. This could open entirely new therapeutic avenues for existent and newly developed human IgG antibodies against any disease where modulation of cell signaling is desired.

SAPNAs have a huge potential, as their use would not be limited to a single, or few diseases. Their potential is also not fixed, as the number of monoclonal antibody products developed increases, so does the potential uses for the SAPNAs. In some embodiments, the SAPNA structure is used to target cancer in immunotherapy, as there are well-defined ligand-receptor interactions that can be modulated, along with several therapeutic IgG antibodies available (such as, anti-PD-1/PD-L1, anti-CTLA4). For a list of therapeutic antibodies, their origin and isotype, method of action, and licensed indication see reference. Additionally, cancer immunology is a research field largely based on the use of antibody-staining based flow cytometry, which would allow for extensive pre-clinical candidates to test. The present invention provides for a nucleic acid encoding the protein cage polypeptide of the present invention. In some embodiments, the nucleic acid is polynucleotide. In some embodiments, the nucleic acid is vector, such as an expression vector. In some embodiments, the nucleic acid encoding the protein cage polypeptide is operatively linked to a promoter capable of expressing the protein cage polypeptide in a host cell. In some embodiments, the nucleic acid is a vector capable of stable introduction into and/or maintenance in the host cell.

The present invention provides for a host cell comprising the nucleic acid encoding the protein cage polypeptide of the present invention. In some embodiments, the nucleic acid is a vector capable of stable introduction into and/or maintenance in the host cell.

The present invention provides for a composition comprising the protein cage polypeptide (or scaffolding protein) or hollow tetrahedral pyramid structure of the present invention, wherein the protein cage polypeptide (or scaffolding protein) or hollow tetrahedral pyramid structure is binding specifically to an antibody or part thereof, or any chimeric protein, molecule or compound comprising the antibody, or part thereof.

The present invention provides for a method for producing the protein cage polypeptide, comprising: (a) providing a host cell of the present invention, (b) culturing the host cell under a suitable condition wherein the protein cage polypeptide is expressed, and (c) optionally recovering the protein cage polypeptide.

The present invention provides for a method for detecting or isolating a pathogenic biological agent, or part thereof, the method comprising: (a) providing a SAPNX (e.g., SAPNA) wherein the antibody is capable of binding specifically to a pathogenic biological agent, or part thereof; (b) contacting the SAPNX with a sample comprising the pathogenic biological agent, or part thereof, such that the SAPNX binds the pathogenic biological agent, or part thereof; (c) detecting the SAPNX pathogenic biological agent, or part thereof via detection, and/or separating the SAPNX bound pathogenic biological agent, or part thereof, from the rest of the sample; and (d) determining the abundance of the pathogenic biological agent, or part thereof.

In some embodiments, the method further comprises: obtaining a sample from a subject suffering from, diagnosed with, or suspected to be suffering from a disease caused by a pathogenic biological agent. In some embodiments, the subject is a human. In some embodiments, the subject is a mammal or bird. In some embodiments, the subject is a common pet or livestock animal. In some embodiments, method further comprises: treating the subject for the disease, such as administering a therapeutically effective dose of a medication to the subject known or capable of curing or alleviating the effects of the disease.

The present invention provides for a SAPNX (e.g., SAPNA) that is chemically conjugated with one or more chemical compounds, such as one or more drugs, and then targeted to biological/cellular sites for drug deposition in an analogous fashion to antibody-drug conjugates (ADCs).

In some embodiments, the present invention provides a SAPNX (e.g., SAPNA) comprising one or more passenger molecules within its interior cavity, wherein said one or more passenger molecules are released from the interior cavity when the SAPNX is cleaved by a protease.

In some embodiments, when one or more passenger molecules are covalently linked to a surface of the interior cavity of a SAPNX, the one or more passenger molecules are exposed to the exterior environment of the SAPNX when the SAPNX is cleaved by a protease.

BRIEF DESCRIPTION OF THE DRAWINGS

This invention is further understood by reference to the drawings wherein:

FIG. 6: Conserved SAPNA sequence (SEQ ID NO: 40). Legend: 284 residues conserved/maintained (284/456=62%); "*"=conserved oligomerization interface residues and highly conserved residues based on evolution (multiple sequence alignments); also includes residues that were determined not to tolerate insertions/deletions. This includes residues on either side of attempted insertion (bolded *); "$"=insertions allowed and tolerated between these residues; "^"=deletions allowed with replacement insertions of varying lengths (First site: 17 to 25 residues in length and must include DCAWHLGELVWCT (SEQ ID NO: 41) or GCDCAWHLGELVWCTCG (SEQ ID NO: 42) and Second site: 28 to 85 residues in length and must include DCAWHLGELVWCT (SEQ ID NO: 41) or GCDCAWHLGELVWCTCG (SEQ ID NO: 42)); "#"=point mutation, such as single charge swap mutations from negative to positive allowed; "@"=alpha helix linking two domains that could tolerate length adjustment; ""=blank space above residue means non conserved, can be any amino acid.

FIG. 12: SAPNA maintains its structure after chemical conjugation with Alexa Fluor®-488.

FIG. 17: Panel A) Characterization of cages formed by M1 and M14-TEV by size exclusion chromatography. Panel B) Characterization of M1 cages by negative stain electron microscopy.

Figure 1A:
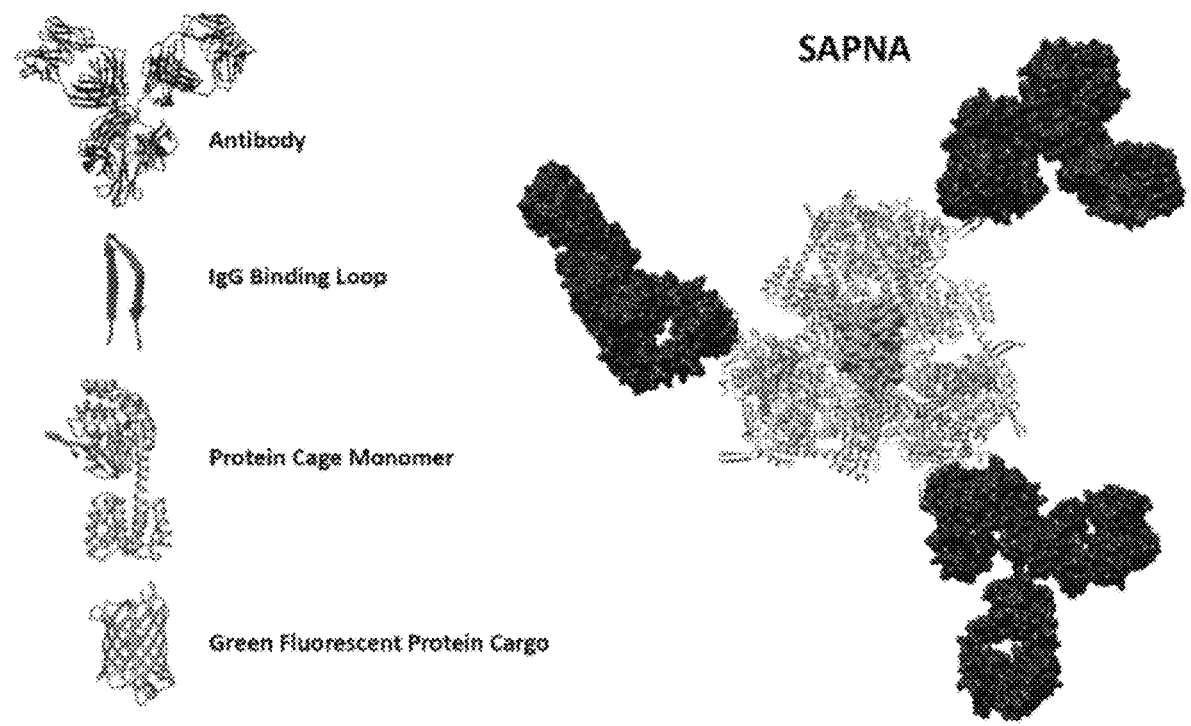
FIG. 1A: A SAPNA model and parts thereof.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DETAILED DESCRIPTION OF THE INVENTION

Disclosed herein are Self-Assembling Protein Nanoparticles (SAPN) decorated with given passenger molecules (X) of interest, referred to herein as "SAPNX". As disclosed herein, SAPNX comprise a protein scaffold and a given passenger molecule attached covalently or non-covalently thereto. SAPNX include SAPNAs as described herein; however, as exemplified herein, the given passenger molecule need not be an antibody or binding fragment thereof.

As used herein, "passenger molecules" refer to molecules of interest that are carried on the surface of SAPNX, molecules of interest that are enclosed within the interior cavities of SAPNX, and molecules of interest that are covalently attached to the SAPNX (e.g., as a fusion protein). In some embodiments, the passenger molecule is a protein (or fragment thereof), which is referred to herein as a "passenger peptide" or "passenger protein". Passenger peptides are amino acid sequences that are in addition to SEQ ID NO: 64. In some embodiments, the passenger peptide is a binding partner involved in a protein-protein interaction. In some embodiments, the passenger peptide comprises the CDRs of the $V_L$ chain and/or $V_H$ chain of an antibody known in the art and may be provided in the form of any antibody format known in the art, e.g., ScFv fragments, Fab fragments, nanobodies, minibodies, diabodies, single-chain antibodies, DARPins, and the like. In some embodiments, the passenger peptide is a peptide tag such as an ALFA-tag, an AviTag, a C-tag, a Calmodulin-tag, a polyglutamate tag, a polyarginine tag, an E-tag, a FLAG-tag, an HA-tag, a His-tag, a Myc-tag, an NE-tag, a Rho1D4-tag, an S-tag, a SBP-tag, a Softag 1, a Softag 3, a Spot-tag, a Strep-tag, a T7-tag, a TC tag, a Ty tag, a V5 tag, a VSV-tag, an Xpress tag, and the like. In some embodiments, the passenger peptide is a covalent peptide tag such as an Isopeptag which covalent binds to pillin-C protein, a SpyTag which covalently binds SpyCatcher protein, a SnoopTag which covalently binds SnoopCatcher protein, a SnoopTagJr which covalently binds SnoopCatcher or DogTag, a DogTag which covalently binds SnoopTagJr, a SdyTag which covalently binds SdyCatcher protein, and the like. In some embodiments, the passenger peptide is a protein tag such as a BCCP (Biotin Carboxyl Carrier Protein) which is biotinylated by BirA enabling recognition by streptavidin, a Glutathione-S-transferase-tag which binds glutathione, a Green fluorescent protein-tag, a HaloTag which covalently binds haloalkane substrates, a SNAP-tag which covalently binds benzylguanine derivatives, a CLIP-tag which covalently binds benzylcytosine derivatives, a HUH endonuclease (HUH-tag) which covalently bind their given target single-stranded DNA, a Maltose binding protein-tag which binds amylose agarose, a Nus-tag, a Thioredoxin-tag, a Fc-tag, a Carbohydrate Recognition Domain or CRDSAT-tag which binds lactose agarose or sepharose, and the like. In some embodiments, SAPNX comprising such passenger peptides may be used in detection assays. In some embodiments, SAPNX comprising such passenger peptides may be used to attach one or more additional passenger molecules (which comprise the binding partner(s) of the given covalent peptide or protein tag(s) attached thereto) to the SAPNX. In some embodiments, the passenger peptide is an enzyme such as alkysulfatases, amylolytic enzymes (e.g., amylases), cellulolytic enzymes (e.g., cellulases), chitinases, cyanidases, hydratases, oxygenases (e.g., biphenyl dioxygenase (BphA), 2,3-dihydroxy-biphenyl-dioxygenase (BphC)), oxidases, hydrolases (e.g., biphenyl hydrolase (BphD)), hydrogenases (e.g., dihydro-dihydroxybiphenyl dehydrogenase (BphB)), peroxidases, lipases, esterases, phosphatases, proteases, tyrosinases, and the like. See, e.g., Nicell, J. (2001) Interdisciplinary Environmental Review 2001 3(1): 14-41; see also McConnell, et al. ACS Synth Biol. 9, 381-391 (2020), which herein incorporated by reference in their entirety. In some embodiments, the protease has broad specificity and cleaves at a position defined primarily by a single amino acid type; such proteases include trypsin, chymotrypsin, glutamyl endopeptidase (GluC), Arg-C protease, and lysC. In some embodiments, the protease has narrow-specificity and cleaves specific amino acid sequences; such proteases include thrombin, TEV, Factor Xa, and Caspase types 1 through 10. In some embodiments, the passenger peptide is a substrate for an enzyme such as those exemplified herein. In some embodiments, proteolysis of the passenger peptide results in instability of the tetrahedral pyramid structure and thereby releases any passenger molecules contained in the interior cavity of the SAPNX. In some embodiments, proteolysis of the passenger peptide results in instability of the tetrahedral pyramid structure and thereby exposes amino acids facing the interior cavity of the SAPNX and any passenger molecules linked thereto to the environment surrounding the SAPNX. In some embodiments, the passenger peptide is LVPRGSG (SEQ ID NO: 53), GSENLYFQGGS (SEQ ID NO: 54), LPXTG (SEQ ID NO: 65), AHIVMV-DAYKPTK (SEQ ID NO: 66), ATHIKFSKRD (SEQ ID NO: 67), CCPGCC (SEQ ID NO: 68), DIPATYEFTDGKHYITNEPIPPK (SEQ ID NO: 69), DLYDDDDK (SEQ ID NO: 70), DPIVMIDNDKPIT (SEQ ID NO: 71), DYKDDDDK (SEQ ID NO: 72), EEEEEE (SEQ ID NO: 73), EQKLISEEDL (SEQ ID NO: 74), EVHTNQDPLD (SEQ ID NO: 75), GAPVPYPDPLEPR (SEQ ID NO: 76), GKPIPNPLLGLDST (SEQ ID NO: 77), GLNDIFEAQKIEWHE (SEQ ID NO: 78), KETAAAKFERQHMDS (SEQ ID NO: 79), KLGDIEFIKVNK (SEQ ID NO: 80), KLGSIEFIKVNK (SEQ ID NO: 81), KRRWKKNFIAVSAANRFKKISSSGAL (SEQ ID NO: 82), MASMTGGQQMG (SEQ ID NO: 83), MDEKTTGWRGGHVVEGLAGELEQLRAR-LEHHPQGQREP (SEQ ID NO: 84), PDRVRAVSHWSS (SEQ ID NO: 85), SLAELLNAGLGGS (SEQ ID NO: 86), SRLEEELRRRLTE (SEQ ID NO: 87), TDKDM-TITFTNKKDAE (SEQ ID NO: 88), TETSQVAPA (SEQ ID NO: 89), TKENPRSNQEESYDDNES (SEQ ID NO: 90), TQDPSRVG (SEQ ID NO: 91), VPTIVMVDAYKRYK (SEQ ID NO: 92), WSHPQFEK (SEQ ID NO: 93), YPYDVPDYA (SEQ ID NO: 94), or YTDIEMNRLGK (SEQ ID NO: 95). In some embodiments, INSERT A and/or INSERT B is a passenger peptide as described above.

In some embodiments, the passenger molecule is covalently linked to its SAPNX using methods, e.g., recombinant techniques, in the art. In some embodiments, the passenger molecule is covalently linked to SAPNX using a linker, e.g., a flexible amino acid linker, in the art. In some embodiments, one or more passenger molecules are attached directly or indirectly (e.g., via a linker) to the outside, the inside, or both the outside and inside of the SAPNX. In some embodiments, the covalent link between a given passenger molecule and a given SAPNX is by way of chemical modification and/or protein coupling methods in the art. See, e.g., Benner, et al. (2017) ACS Nano 11: 872-881. In some embodiments, where multiple passenger molecules (which may be the same or different) are attached to a given SAPNX, the manner in which the multiple passenger molecules are attached may be the same or different, e.g., some passenger molecules may be indirectly attached by way of affinity binding, while other passenger molecules are covalently attached.

One can modify the expression of a nucleic acid encoding any protein cage polypeptide taught herein by a variety of methods in accordance with the methods of the invention. Those skilled in the art would recognize that increasing gene copy number, ribosome binding site strength, promoter strength, and various transcriptional regulators can be employed to alter a protein expression level.

The present invention can be used for a variety of purposes (which as described can be used in a research context as a tool, or a clinical setting as a therapeutic): In some embodiments, the SAPNX (e.g., SAPNA) structure is a therapeutic or research tool capable of modulating the immune system by binding/blocking cell-surface and soluble receptor/ligands in humans or research models. In some embodiments, the SAPNX (e.g., SAPNA) structure is capable of activating one or more internal cellular pathways through enforcing external cell-surface receptor/ligand oligomerization. In some embodiments, the SAPNX (e.g., SAPNA) structure is labeled, such as with a fluorescent dye or label, and can be used to visualize cell-surface targeting antibodies, such as in immunofluorescence or flow cytometry. In some embodiments, the fluorescent dye is an Alexa Fluor® fluorescent dye. In some embodiments, the SAPNX (e.g., SAPNA) structure is a tool to test/screen the feasibility of using any combination of human/rabbit IgG antibodies to effect a cellular change or physiological response in a living organism. In some embodiments, the SAPNX (e.g., SAPNA) structure is useful for opsonization of circulating and invading particles in vivo. In some embodiments, the SAPNX (e.g., SAPNA) structure is capable of targeting and manipulating viruses/viral particles in an aqueous or semi-aqueous environment. In some embodiments, the SAPNX (e.g., SAPNA) structure is capable of encapsulating a cargo, with subsequent targeting to cell-surfaces. In some embodiments, the SAPNX (e.g., SAPNA) structure is capable of gaining access to an internal cellular environment through endocytosis, with or without cargo (initiation and modulation of endocytosis). In some embodiments, the SAPNX (e.g., SAPNA) structure is a vaccine or vaccine adjuvant. In some embodiments, the SAPNX (e.g., SAPNA) structure is an in vitro immune cell activation tool. In some embodiments, the SAPNX (e.g., SAPNA) structure is a biodegradable aesthetic product that binds fluorescent proteins to keratin in hair and skin through displaying an anti-fluorescent antibody and anti-keratin antibody on the same scaffold. In some embodiments, the SAPNX (e.g., SAPNA) molecule loaded with antibodies can positively or negatively select cellular populations from a mixed pool of cells.

Many antibodies fail clinical trials, which has led to research into enhancing antibody dependent cell mediated cytotoxicity (ADCC). However, these efforts are largely aimed at enhancing Fc-gamma receptor binding to antibody Fc regions through Fc mutations. The SAPNX (e.g., SAPNA) nanocages would be superior to these methods, as ADCC requires Fc-gamma receptor aggregation through Fc binding, which the SAPNX (e.g., SAPNAs) would physically enforce.

Additionally, the SAPNX (e.g., SAPNAs) could take advantage of these efforts, and in fact be loaded with the mutated Fcs to further augment therapeutic efficacy.

Bi-/multi-specific antibodies, which are essentially antibodies that contain two or more different antigen recognition regions, are connected in a variety of ways. While bi-/multi-specific antibodies have great potential, each one must be individually designed, tested, and optimized, compared to the SAPNX (e.g., SAPNA), which would be modular and available for use by almost any commercially available IgG antibody. A major advantage possessed by the SAPNX (e.g., SAPNAs), is that other non-antibody molecules can be displayed at the same time as the antibodies. Pre-formulating mixtures of different antibodies and subsequent addition of unloaded SAPNX (e.g., SAPNA) cages, would allow for loading of several (~2-12) different antibodies onto the same nanocage. This can then act as a large multi-specific nanoparticle, which is a great advantage over the current multi-specific antibodies. The modular nature and multi-functionality of the SAPNX (e.g., SAPNAs) are highly desirable characteristics in next-generation biological therapeutics.

In some embodiments, the protein cage polypeptide (or scaffolding protein) is binding specifically to the antibody or part thereof, or any chimeric protein, molecule or compound comprising the antibody, or part thereof; wherein the antibody or part thereof is binding specifically to a pathogenic biological agent, or part thereof.

In some embodiments, the tetrahedral pyramid structure is binding specifically to the antibody or part thereof, or any chimeric protein, molecule or compound comprising the antibody, or part thereof; wherein the antibody or part thereof is binding specifically to a pathogenic biological agent, or part thereof.

In some embodiments, the SAPNX (e.g., SAPNA) molecule can be used as a multi-valent detection platform for pathogenic biological agents, including, but not limited to, viruses, bacteria, and misfolded proteins implicated in any human/mammalian diseases (such as prions and other amyloids), by loading the SAPNX (e.g., SAPNA) molecule with one or more antibodies against antigenic proteins or other surface molecules specific to those agents. Detection applications extend to isolation and determination of abundance (i.e., infection severity) for the pathogenic agents. As previously noted, for purposes of analysis, the SAPNX (e.g., SAPNA) molecule can be covalently labeled with a molecule such as a fluorophore for detection, while the multi-valent His-tags (up to 12 copies) can be used to manipulate and isolate various antigen-bound fractions. In addition to humans, the pathogenic agents to be analyzed extend to those affecting animals that are of interest to human health and welfare (e.g., common pets, livestock, etc.). In some embodiments, the common pet is a dog, cat, rabbit, guinea pig, hamster, mouse, or the like. In some embodiments, the livestock is a mammal, such as cattle, horse, pig, sheep, or goat, or a bird, such a chicken, duck, or goose.

The surfaces of viruses and bacteria are coated or decorated with proteins or other molecules that are necessary for their biological functions, including for host cell attachment and host entry, and for survival under harsh conditions. Owing to their importance to propagation, such molecules, or parts of those molecules, tend to be conserved for a given species or strain of virus or bacterium. As a result, such molecules can serve as robust targets for identification. Such molecules are furthermore specific and distinct for different viruses and bacteria and are therefore suitable for specific assignment of identity in diagnostic applications. The ability to recognize specific viruses and bacteria by antibody binding to their surface molecules, or sometimes to molecules produced by their lysis, is understood and widely applied in practice. In some embodiments, the SAPNX (e.g., SAPNA) molecules provide distinct and advantageous features for identifying and isolating viruses and bacteria owing to the polyvalent and modular capacity of SAPNX (e.g., SAPNA) to display selected antibodies conferring specific recognition profiles for binding, and their support of chemical features for isolation and reporter readout, for example by fluorescence.

Different embodiments of the invention may present more than one distinct type of antibody on the SAPNX (e.g., SAPNA) molecule. For example, a SAPNX (e.g., SAPNA) molecule can simultaneously present antibodies specific for different strains or subtypes of one type of virus or bacterium. This would provide for facile and efficacious identification of viruses with known variants or subtypes in a population. The influenza virus is a well-understood example. This would obviate the need to design different reagents for the detection of variant strains of a virus.

Presentation of more than one type of antibody could furthermore provide a valuable advantage in discriminating between pathogens (e.g. different bacteria) that express partially overlapping sets of surface antigens. As an example, if bacterium A expresses surface proteins X and Y, and bacterium B expressed proteins Y and Z, and bacterium C expresses proteins X and Z, then a SAPNX (e.g., SAPNA) molecule presenting antigens directed against proteins Y and Z will, by avidity effects, preferentially identify bacterium B. Of course, other scenarios for preferential detection of combinations of surface antigens will be possible, which is true for both bacteria and viruses.

Different embodiments of the invention may have different numbers of a single type of antibody presented on the SAPNX (e.g., SAPNA) molecule, achieved by addition of antibodies in different stoichiometric amounts relative to the SAPNX (e.g., SAPNA) core. Because the degree of polyvalency in molecular binding is understood to strongly affect binding avidity, the ability to tailor the number of antibodies presented on a SAPNX (e.g., SAPNA) molecule can confer valuable control over final binding affinity (i.e., tunability). Such control provides value in creating a reagent with the most desirable window of detection for positive binding of intended target molecules, while still giving negative binding readout for non-cognate molecules that may be similar in different degrees to the intended detection target. A narrow range of affinity versus target specificity is a common challenge for previous mono-valent or low-valent reagents used for bacterial target identification.

Different embodiments of the invention will be specific for different viral, bacterial, and amyloid marker proteins. The possible target list is expansive, continually growing with the discovery of new pathogens, and requires only that specific antibodies are known or can be established for the marker protein of interest (a capability routinely demonstrated in industry today). Among viruses of medical urgency, the spike (S) proteins of various coronaviruses, including SARS-CoV, SARS-CoV-2, and MERS-CoV, would be example targets for identification. The gp120 glycoprotein is an example identification target for the HIV virus. The GP surface protein is an example target for Ebola virus. The hemagglutinin (HA) protein is an example target for the influenza virus, with different viral subtypes identifiable by different HA variants. For bacterial targets, example embodiments would be directed against diverse surface proteins and polysaccharide molecules. Specific examples of value in human pathogenesis would include SAPNX (e.g., SAPNA) molecules bearing antibodies to capsular polysaccharides (CPS) from *Haemophilus influenza* type b (Hib) or group B *Streptococcus*, or any number of other pathogens with capsular polysaccharide coats. Further examples would be SAPNX (e.g., SAPNA) molecules with antibodies to: the outer surface protein (OspA) of the causative agent of Lyme disease (*Borrelia burgdorferi* or related species), the poly D-glutamic acid capsule antigen of *Bacillus anthracis*, or the heparin binding antigen (NHBA) of *Neisseria* gonorrhea. Prion and other amyloid diseases are often neurodegenerative and can affect both humans and animals. In these pathologies, otherwise natural proteins misfold and then aggregate to form cytotoxic amyloid aggregates, which can distribute systemically, accumulate in diverse organ systems, and lead to disease. Of relevance to this embodiment of the invention, the unfolded/aggregated toxic forms of prion/amyloid proteins have conformations different from the natively folded forms of the proteins, making the toxic forms of these pathogenic agents distinguishable by antibodies. Examples of prion diseases, whose pathogenic proteins could be detected using SAPNX (e.g., SAPNA) molecules, are Creutzfeldt-Jokob Disease in humans and Bovine Spongiform Encephalopathy ("Mad Cow Disease") in cows. Detection of pathogenic proteins would extend to other amyloid proteins: A-beta (involved in Alzheimer's Disease), tau protein (involved in diverse tauopathies), alpha-synuclein (involved in Parkinson's disease), transthyretic (involved in systemic amyloidosis), and others. These represent only selected examples.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Materials and Methods
Design of Self-Assembling Protein Nanoparticles Decorated with Antibodies (SAPNA)

The workflow for SAPNA was an iterative process of: engineer a set of DNA constructs, attempt to express protein, and if protein expressed, characterize said construct and test it for human Fc (hFc) binding. Site-directed mutagenesis was used to incorporate synthesized DNA fragments into the template scaffold (cloned into the pET22b$^+$ vector) and make subsequent mutations to any new constructs. The scaffold template, a self-assembling tetrahedral protein cage, originated from work in the Yeates lab of UCLA. Through recent collaboration, the unique capabilities of the high-throughput small-angle X-ray scattering (HT-SAXS) beamline was used to structurally characterize two scaffold variants under varying salt and pH conditions in solution. These two scaffold variants were used as templates for further functional engineering. The aim was to functionalize the scaffold to display antibodies with many possible uses in mind (see above). Through viewing of the available structures of the template scaffold and multiple sequence alignments of evolutionarily-related homologs, potential sites for mutagenesis were identified. Upon sequencing verification of correct sequence, constructs were expressed and purified in parallel. The following buffers were used in the purification: 1. Lysis (50 mM Tris pH 8.0, 300 mM NaCl, 10 mM Imidazole), 2. Wash (50 mM Tris pH 8.0, 300 mM NaCl, 100 mM Imidazole), 3. Elution (50 mM Tris pH 8.0, 300 mM NaCl, 300 mM Imidazole), 4. Gel Filtration (20 mM Tris pH 7.4 or 8.0, 100 mM NaCl, OR PBS pH 7.4, OR PBS pH 7.4, 0.05% Triton-X100). Upon elution of the His-tagged proteins from Ni-NTA beads, the concentration was measured via absorbance and theoretical extinction coefficients. Due to the high valency of the constructs (12 monomers, each with a His-tag), the increased affinity for the Ni-NTA beads resulted in relatively pure fractions. Therefore, any appreciable concentration of protein above baseline was predicted to be properly- to semi-folded mutant scaffold. Those constructs that resulted in said protein, were further purified by size exclusion chromatography (SEC) and tested in peak-shift assays for hFc binding. This mutagenesis process was repeated until configurations were found that bound hFc without forming an appreciable amount of scaffold oligomers (Table 2). A set of the most optimal configurations were further characterized via the structural technique size exclusion chromatography small-angle X-ray scattering coupled to multi-angle light scattering (SEC-SAXS-MALS).

Relevant Research

The original small peptide motif engineered to bind the Fc region of IgG antibodies was first described in 2000, termed Fc-III. The motif was discovered through the use of peptide phage display, which is an iterative way of selecting for macromolecular binding interactions. Fc-III was further enhanced through the addition of stabilizing amino acids in a cyclic peptide form called Fc-III-4C. In 2012, the Fc-III peptide was incorporated into the loop of a ferritin protein cage and the ability to bind and target antibodies was demonstrated. This ferritin protein cage looks to have been disclosed (WO2013055058A9). As described below, the Fc-III and Fc-III-4C sequences, as well as other protein sequences, were engineered into several sites in the previously mentioned scaffold template. The experimental data show that the proteins demonstrate functional activity when bound or covalently attached to the self-assembling protein-based cages. For example, the Fc-III and Fc-III-4C sequences can reproducibly bind and display human and rabbit IgG antibodies in solution.

Results

Figure 1B:
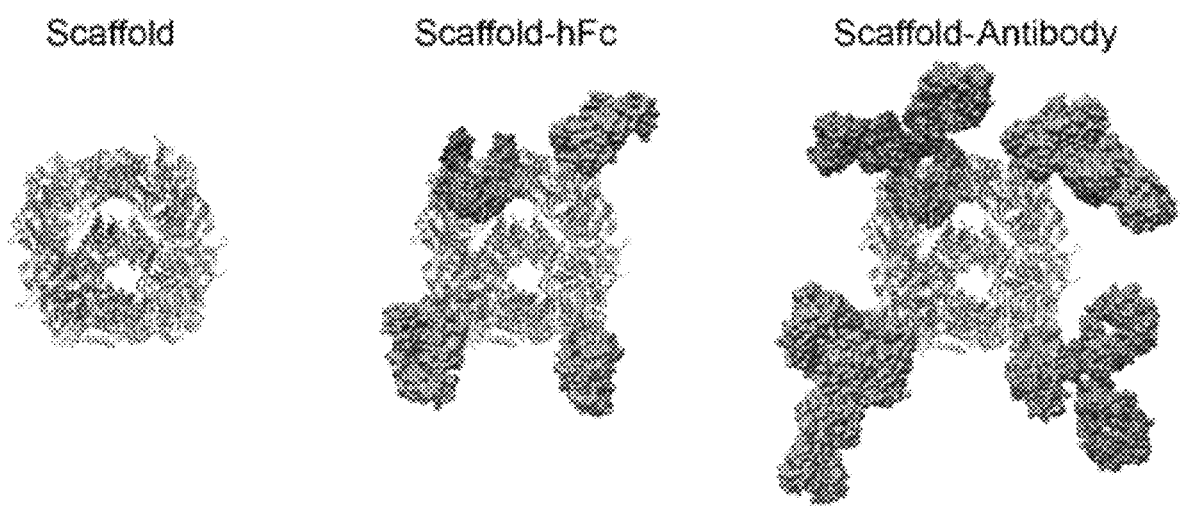
FIG. 1B: Models of predicted structures of various scaffold states.
Figure 2A:
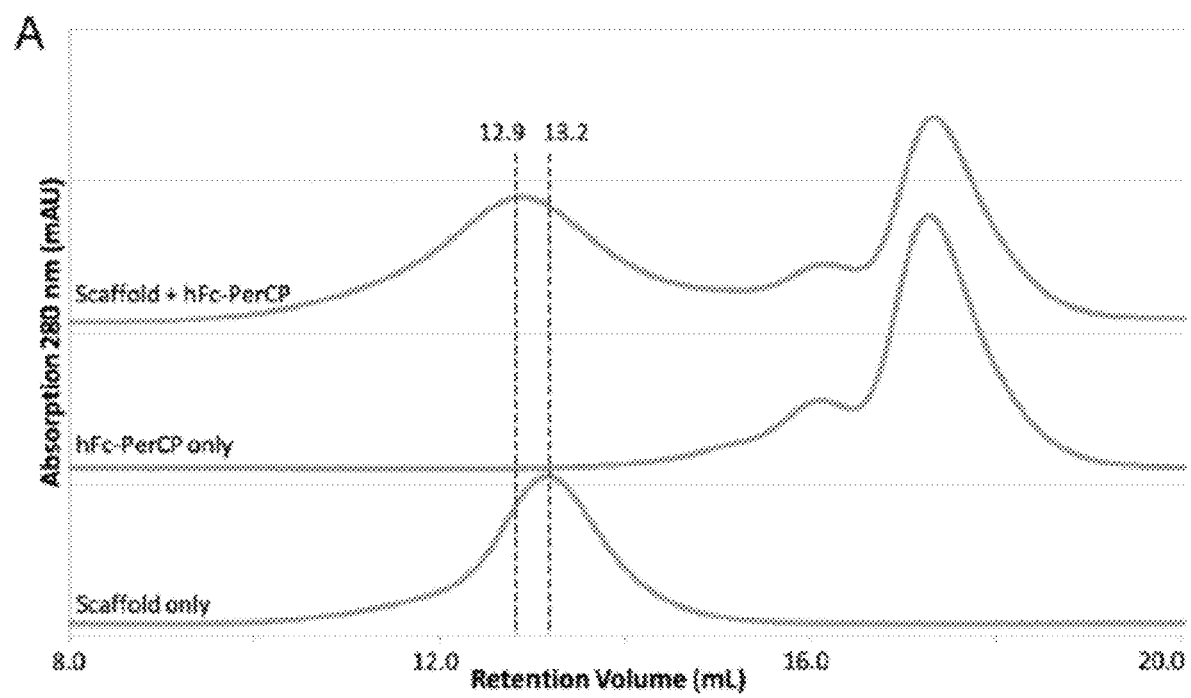
FIG. 2A: SEC peak shift binding assays of a scaffold with the PerCP-labeled human IgG1 Fc domain. Absorbance at 280 nm.
Figure 2B:
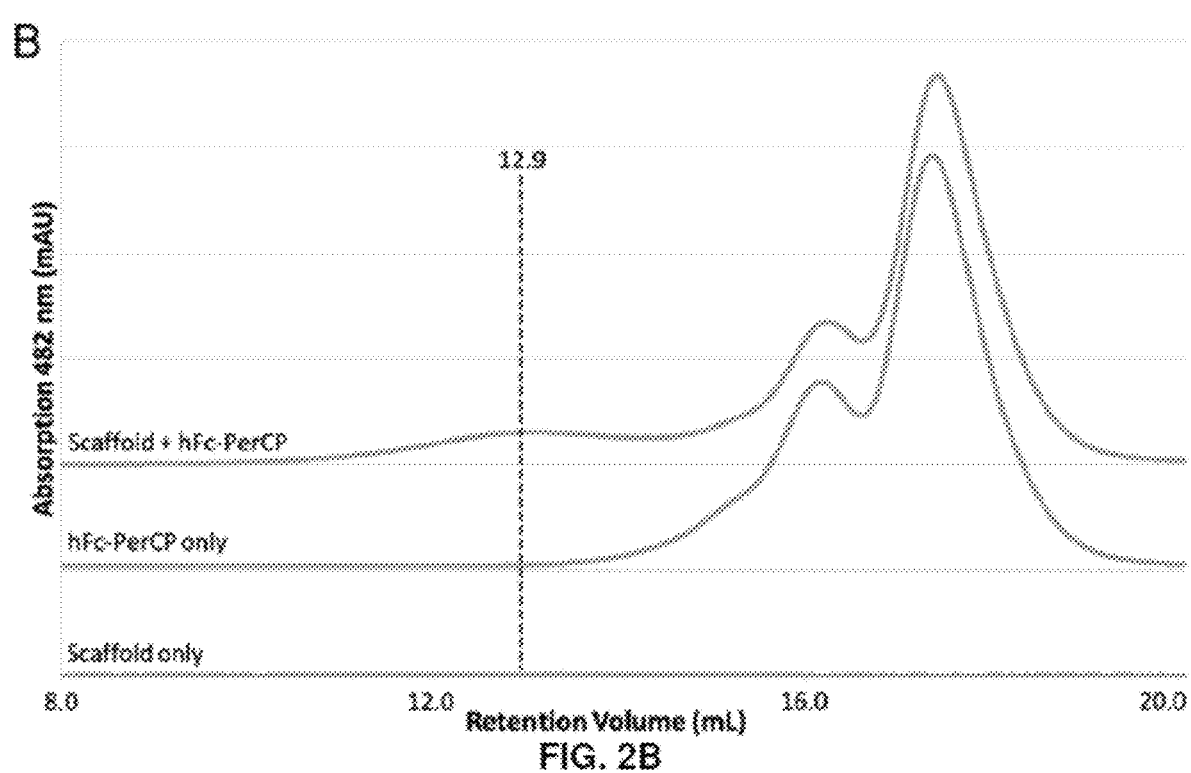
FIG. 2B: SEC peak shift binding assays of a scaffold with the PerCP-labeled human IgG1 Fc domain. Absorbance at 482 nm.
Figure 3A:
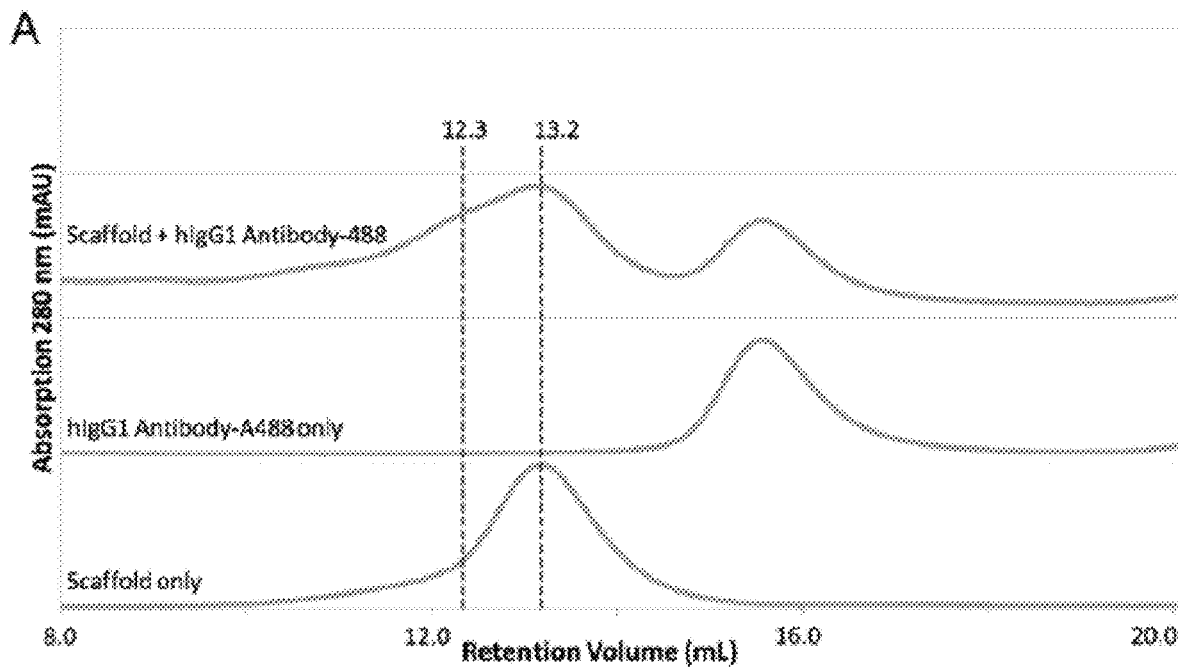
FIG. 3A: SEC peak shift binding assays of a scaffold with an Alexa Fluor®-488-labeled human IgG1 isotype antibody. Absorbance at 280 nm. Alexa Fluor® is a registered trademark owned by Thermo Fisher Scientific (Waltham, Mass.).
Figure 3B:
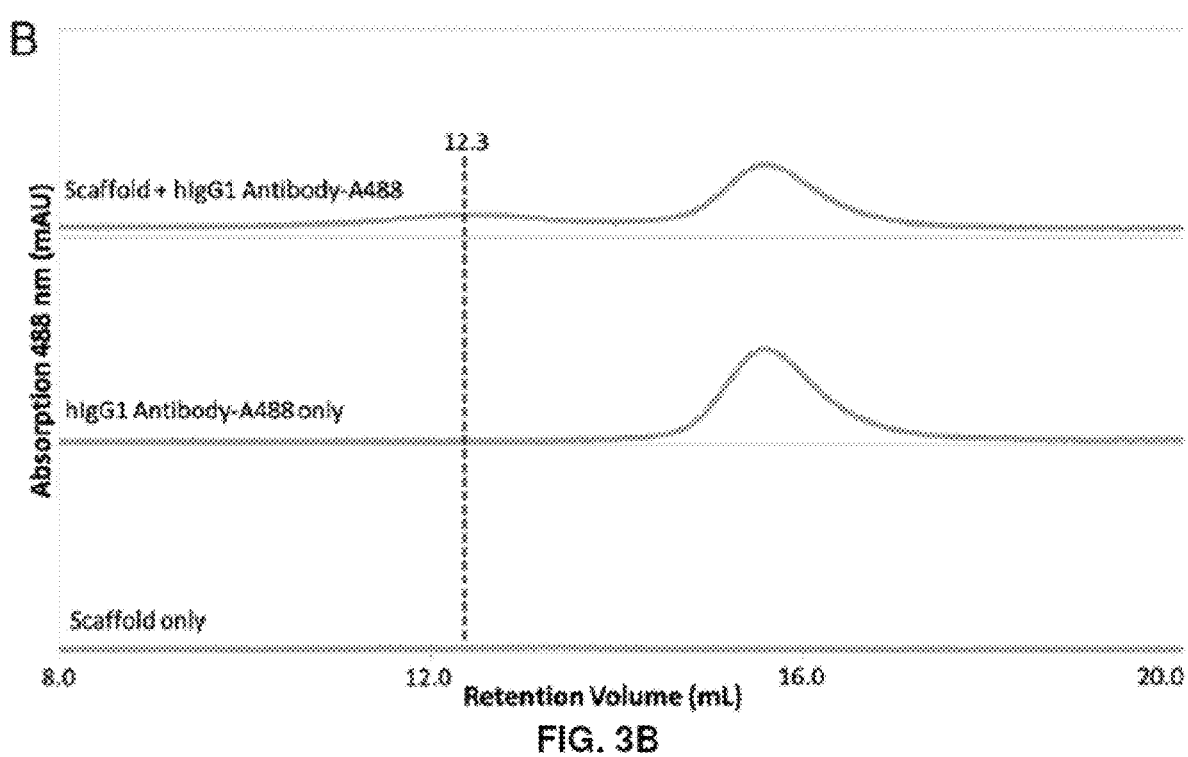
FIG. 3B: SEC peak shift binding assays of a scaffold with an Alexa Fluor®-488-labeled human IgG1 isotype antibody. Absorbance at 488 nm.

Self-assembling protein-based scaffolds that bind and display antibodies have been successfully engineered. The SAPNA structures in FIG. 1 are representative models of predicted structures that the dynamic system can sample in solution when binding human or rabbit IgG Fc domains or antibodies. To biochemically demonstrate the antibody/Fc binding abilities of the scaffold molecules, human IgG1 Fc conjugated to the fluorescent protein, PerCP (Fc-PerCP), was added to a scaffold and run on SEC (FIGS. 2A and 2B). The peak absorbance at 280 nm (A280) which is a readout for protein (FIG. 2A), is shifted from retention volume 13.2 mL to 12.9 mL, showing an increase in size of the scaffold. Additionally, a peak absorbance at 482 nm (A482) which is a readout for the fluorescence from PerCP, appears at 12.9 mL, supporting that the increase in size of the scaffold is due to binding of Fc-PerCP. Similarly, a peak shift assay with an Alexa Fluor®-488 labeled human IgG1 isotype antibody (hIgG1 Antibody-488) was done with a scaffold (FIGS. 3A and 3B). The A280 peak (FIG. 3A), is shifted from retention volume 13.2 mL to 12.3 mL, showing an increase in size of the scaffold. An absorbance 488 (A488) peak which is a readout for the fluorescence from the Alexa Fluor®-488 fluorescent dye, appears at 12.3 mL, supporting that the increase in size of the scaffold is due to binding of hIgG1 Antibody-488. Chemical conjugation of fluorophores and fluorescent proteins to the antibodies/Fcs may reduce the ability of antibodies/Fcs to bind the functionalized scaffold. Therefore, large A482 and A488 peaks in FIG. 2B and FIG. 3B were neither expected nor observed.

Figure 4A:
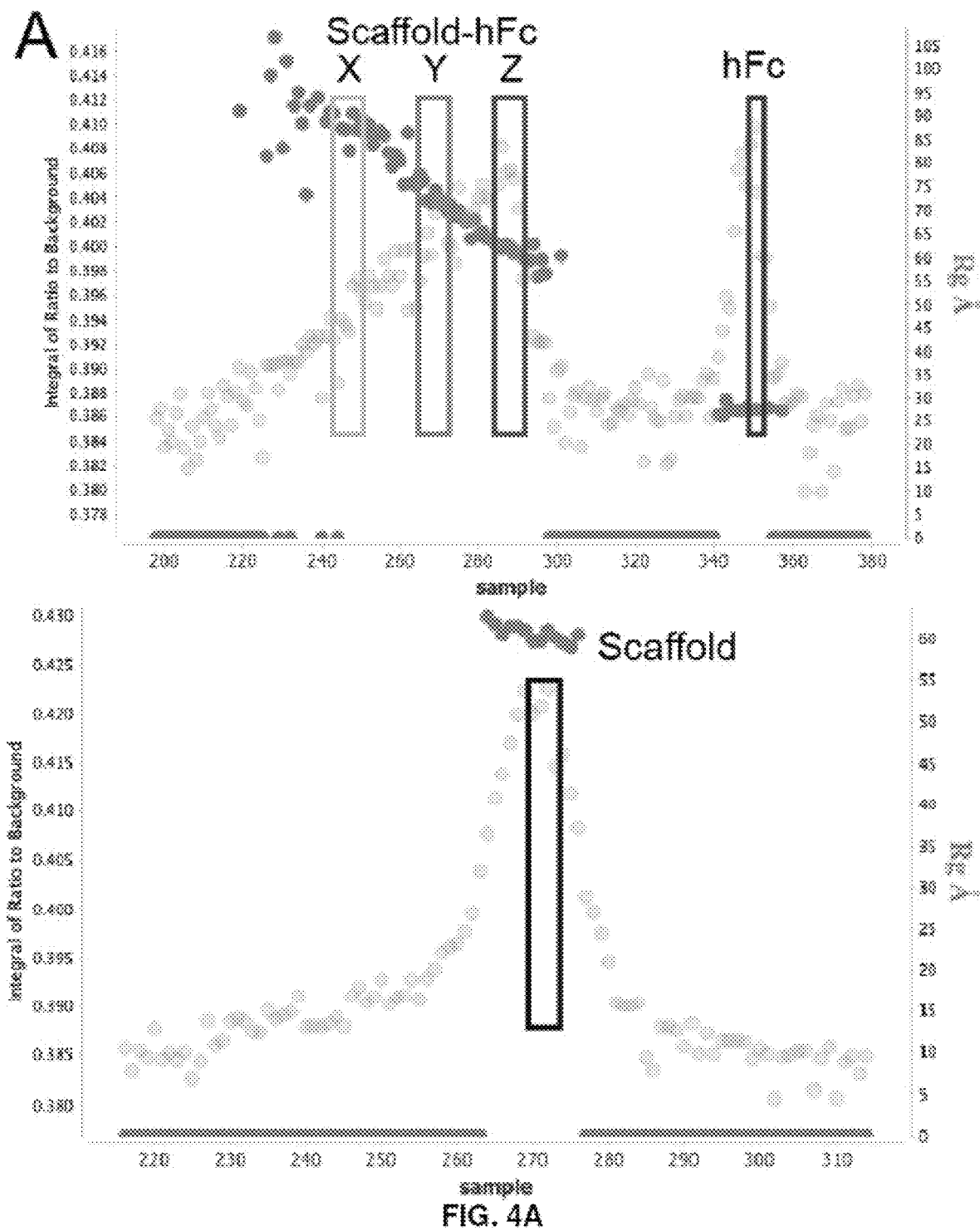
FIG. 4A: SEC SAXS of a scaffold with human IgG1 Fc domain. Sample trace from SEC-SAXS-MALS.
Figure 4B:
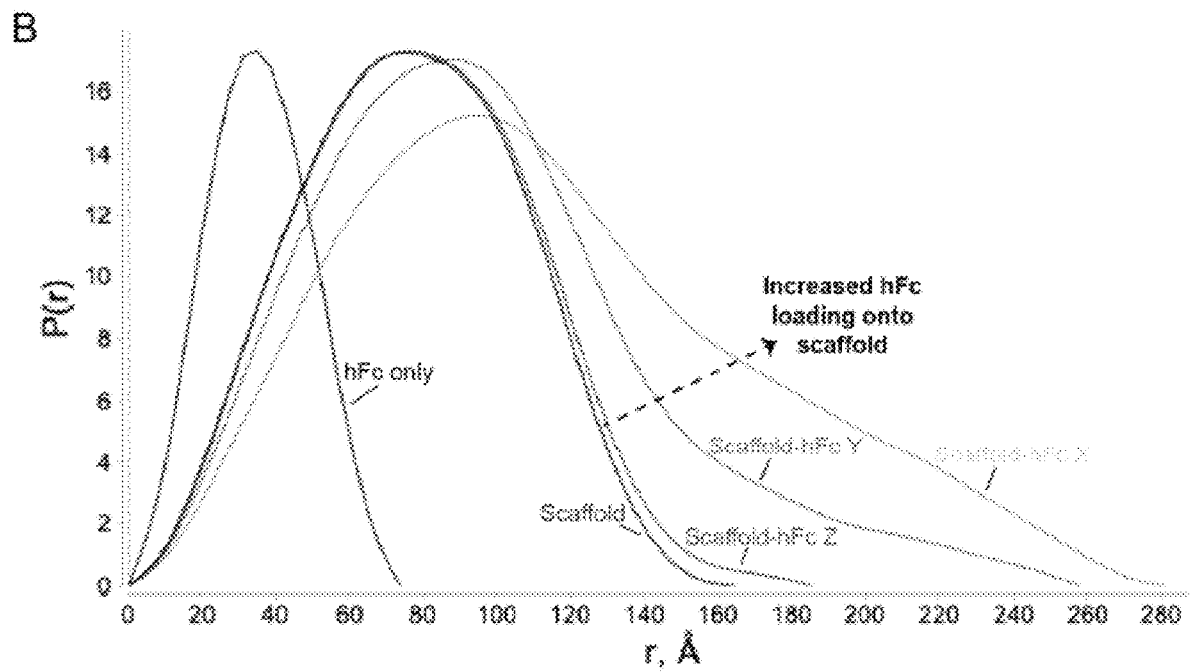
FIG. 4B: SEC SAXS of a scaffold with human IgG1 Fc domain. P(r) function histograms.
Figure 5A:
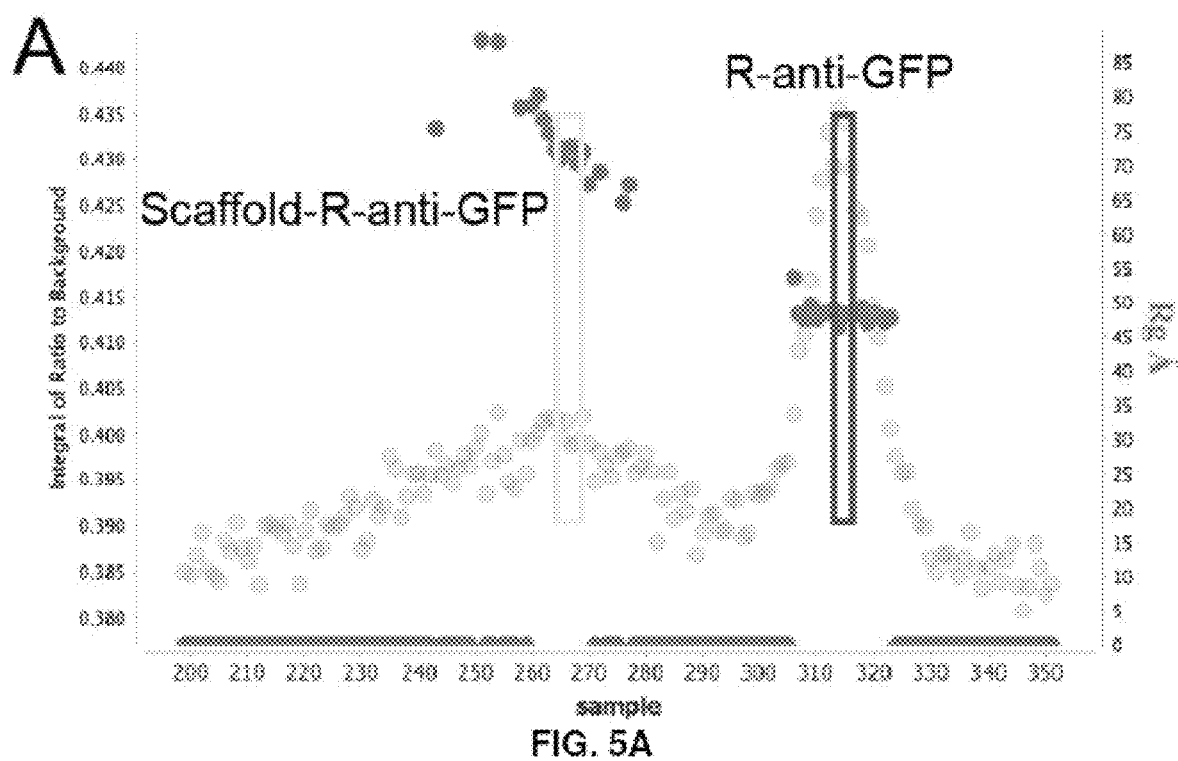
FIG. 5A: SEC SAXS of a scaffold with a rabbit anti-GFP antibody. Sample trace from SEC-SAXS-MALS.
Figure 5B:
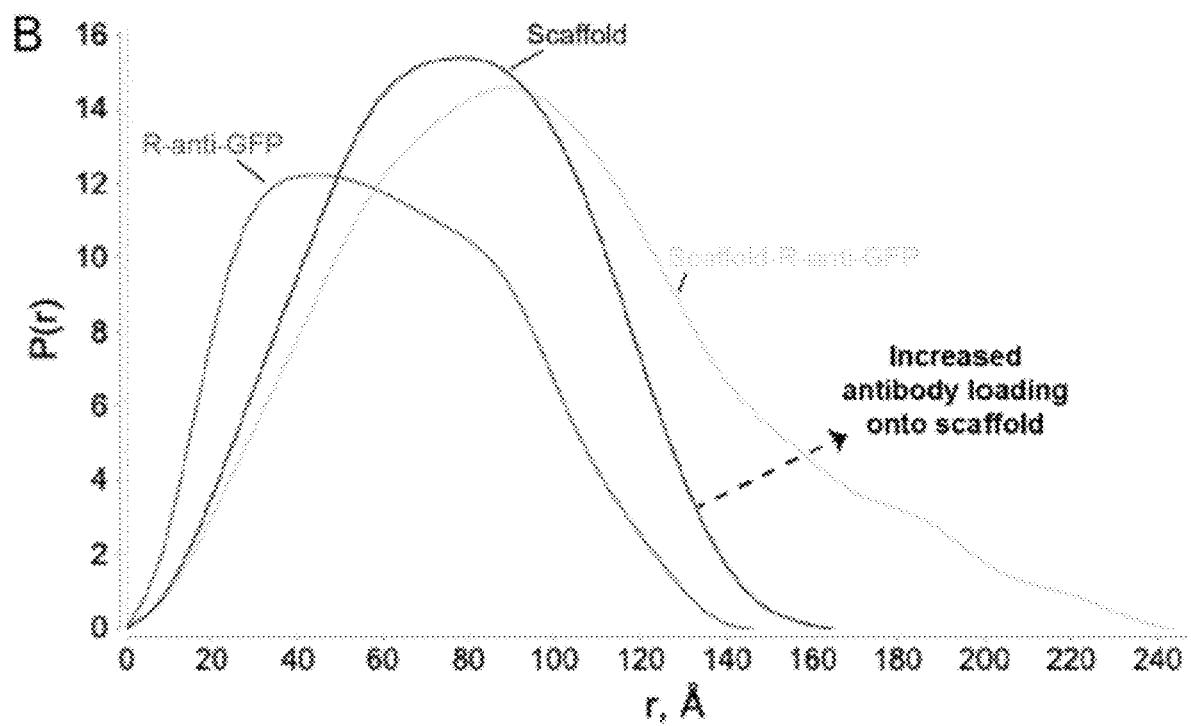
FIG. 5B: SEC SAXS of a scaffold with a rabbit anti-GFP antibody. P(r) function histograms.

To structurally assess the scaffold for Fc and antibody binding, a solution technique SEC-SAXS-MALS (FIGS. 4A, 4B, 5A and 5B, respectively) was employed. Regions of sample peaks of scaffold, hFc, and scaffold-hFc complex were chosen for further scattering analysis (FIG. 4A). All molecules/complexes are compared in FIG. 4B using the P(r) function, which are histograms of orientationally averaged distances of the scattering particles. Thus, the greater the area under these histograms, the greater the magnitude and number of 'molecule edge-to-molecule edge' distances within the molecules there are. Therefore, the increased diameters of the scaffold through the addition of hFc and antibody molecules will be readily apparent via the P(r) function. In FIG. 4B it is clear that the various scaffold states (X, Y, Z) along the Scaffold-hFc peak in FIG. 4A represent loading of hFc molecules onto the scaffold. This loading trend is also seen in the increase in radius of gyration (Rg) and maximum dimension (Dmax) in Table 1. Further support for hFc loading onto the scaffold is in the MALS data in Table 1, where the MALS Averaged Molecular Weight of the Peak increased from 764 kDa to 1020 kDa with the addition of hFc to the scaffold. Similar results were found when characterizing the binding of a polyclonal IgG rabbit anti-GFP antibody to the scaffold (scaffold-R-anti-GFP) using SEC-SAXS-MALS in FIGS. 5A and 5B. Analysis of a single region of the scaffold-R-anti-GFP peak, demonstrates an increase in the P(r) function (FIG. 5B), and the Rg, Dmax, and MALS Averaged Molecular Weight of the Peak (Table 1).

TABLE 1

Characteristics of SAPNA scaffold with hFc (IgG1) and R-anti-GFP antibody (IgG)

| Molecule/Complex | Radius of Gyration (Å) | Maximum Dimension (Å) | MALS Averaged Molecular Weight of Peak (kDa) |
| --- | --- | --- | --- |
| hFc | 27.31 | 74 | 61 |
| Scaffold | 59.76 | 165 | 764 |
| Scaffold-hFc Z | 61.56 | 185 | 1020 |
| Scaffold-hFc Y | 72.47 | 258 | |
| Scaffold-hFc X | 81.39 | 281 | |

TABLE 1-continued

Characteristics of SAPNA scaffold with hFc (IgG1) and R-anti-GFP antibody (IgG)

| Molecule/ Complex | Radius of Gyration (Å) | Maximum Dimension (Å) | MALS Averaged Molecular Weight of Peak (kDa) |
|---|---|---|---|
| R-anti-GFP | 48.09 | 74 | 145 |
| Scaffold-R-anti-GFP | 72.41 | 244 | 1568 |

TABLE 2

Sequences of SAPNA scaffold variants designed and experimentally tested to-date

Initial Published Template (SEQ ID NO: 40)
SAPNA_1 (SEQ ID NO: 1)
SAPNA_2 (SEQ ID NO: 2)
SAPNA_3 (SEQ ID NO: 3)
SAPNA_4 (SEQ ID NO: 4)
SAPNA_5 (SEQ ID NO: 5)
SAPNA_6 (SEQ ID NO: 6)
SAPNA_7 (SEQ ID NO: 7)
SAPNA_8 (SEQ ID NO: 8)
SAPNA_9 (SEQ ID NO: 9)
SAPNA_10 (SEQ ID NO: 10)
SAPNA_11 (SEQ ID NO: 11)
SAPNA_12 (SEQ ID NO: 12)
SAPNA_13 (SEQ ID NO: 13)
SAPNA_14 (SEQ ID NO: 14)
SAPNA_15 (SEQ ID NO: 15)
SAPNA_16 (SEQ ID NO: 16)
SAPNA_17 (SEQ ID NO: 17)
SAPNA_18 (SEQ ID NO: 18)
SAPNA_19 (SEQ ID NO: 19)
SAPNA_20 (SEQ ID NO: 20)
SAPNA_21 (SEQ ID NO: 21)
SAPNA_22 (SEQ ID NO: 22)
SAPNA_23 (SEQ ID NO: 23)
SAPNA_24 (SEQ ID NO: 24)
SAPNA_25 (SEQ ID NO: 25)
SAPNA_26 (SEQ ID NO: 26)
SAPNA_27 (SEQ ID NO: 27)
SAPNA_28 (SEQ ID NO: 28)
SAPNA_29 (SEQ ID NO: 29)
SAPNA_30 (SEQ ID NO: 30)
SAPNA_31 (SEQ ID NO: 31)
SAPNA_32 (SEQ ID NO: 32)
SAPNA_33 (SEQ ID NO: 33)
SAPNA_34 (SEQ ID NO: 34)
SAPNA_35 (SEQ ID NO: 35)
SAPNA_36 (SEQ ID NO: 36)
SAPNA_37 (SEQ ID NO: 37)
SAPNA_38 (SEQ ID NO: 38)
SAPNA_39 (SEQ ID NO: 39)

Example 2

Dynamic Light Scattering (DLS) Analysis of SAPNA Binding of Antibody

Samples were diluted in PBS pH 7.4 and run on a DynaPro Plate Reader III. The DLS acquisition time was 5 seconds and 5 acquisitions were taken per sample. The temperature was 20 degrees Celsius.

Primary Human T Cell Expansion Assay

Primary human pan-T cells (includes CD4$^+$ and CD8$^+$ T cells as well as some gamma/delta T cell subsets) isolated from peripheral blood (PB) mononuclear cells (MNCs) of a random donor were plated in a 96-well plate.

Triplicate wells were treated with soluble SAPNA loaded with varying ratios of anti-CD3/anti-CD28 antibodies, or competing technologies on Day 1. Fresh xeno-free medium containing exogenous recombinant human IL-2 was added every 3-4 days. T cells were stained with the following: Live/Dead stain, anti-CD3, anti-CD4, anti-CD8, anti-CCR7, anti-CD45RA, and anti-CD95 antibodies. T cell differentiation was assessed via flow cytometry, using the literature-supported T cell subset identification staining scheme: $T_{CM}$ (CCR7$^+$ CD45RA$^-$), $T_{EM}$ (CCR7$^-$ CD45RA$^-$), $T_{EMRA}$ (CCR7$^-$ CD45RA$^+$), $T_{SCM}$ (CD45RA$^+$ CCR7$^+$→CD95$^+$), $T_{naive}$ (CD45RA$^+$ CCR7$^+$→CD95$^-$). Samples were run on an LSR Fortessa X20 Analyzer flow cytometer, and data analyzed using FlowJo 10.6.1.

CD8$^+$ T Cell Isolation Using Magnetic Bead-Bound SAPNA 14-day expanded primary human pan-T cells were plated in a 96-well plate. SAPNA was first incubated with magnetic Ni-NTA (mag) beads for 5 minutes at room temperature, and then a rabbit-anti-CD8 antibody was added and incubated for an additional 20 minutes. A control was prepared that withheld SAPNA from the mixture. The control and mag-SAPNA-CD8 beads were added to triplicate wells and the plate was returned to the 37 degrees Celsius, 5% $CO_2$ incubator for 1 hour. The cell-bead solution was resuspended and placed on a magnet for 2 minutes. The bead-bound component was attracted to the magnet, while the supernatant containing the cell suspension was transferred to a new plate for flow cytometry staining. Cells were stained and assessed the same as in the "Primary human T cell expansion assay" section.

Immunofluorescence Microscopy

HeLa cells were cultured in a 37 degree Celsius, 5% $CO_2$ incubator, and seeded on coverslips. Cells were fixed in 4% paraformaldehyde in PBS+0.2% Triton X-100. They were then permeabilized for 30 minutes in PBS+0.5% Triton X-100 (PBST). Permeabilized cells were blocked for 30 minutes in PBST (+5% FBS). Control staining was done using the rabbit-anti-ROBO1 antibody and a goat-anti-rabbit-A488 secondary antibody. For the experimental group, SAPNA was chemically labeled with Alexa Fluor®-488, and incubated with rabbit-anti-ROBO1 for at least 30 minutes. The loaded SAPNA molecule was then incubated in PBST (+5% FBS) for 1 hr at room temperature. Coverslips were washed with PBST, and then PBS only. Coverslips were mounted using and antifade mounting media containing the DNA stain, DAPI.

Results

Figure 7:
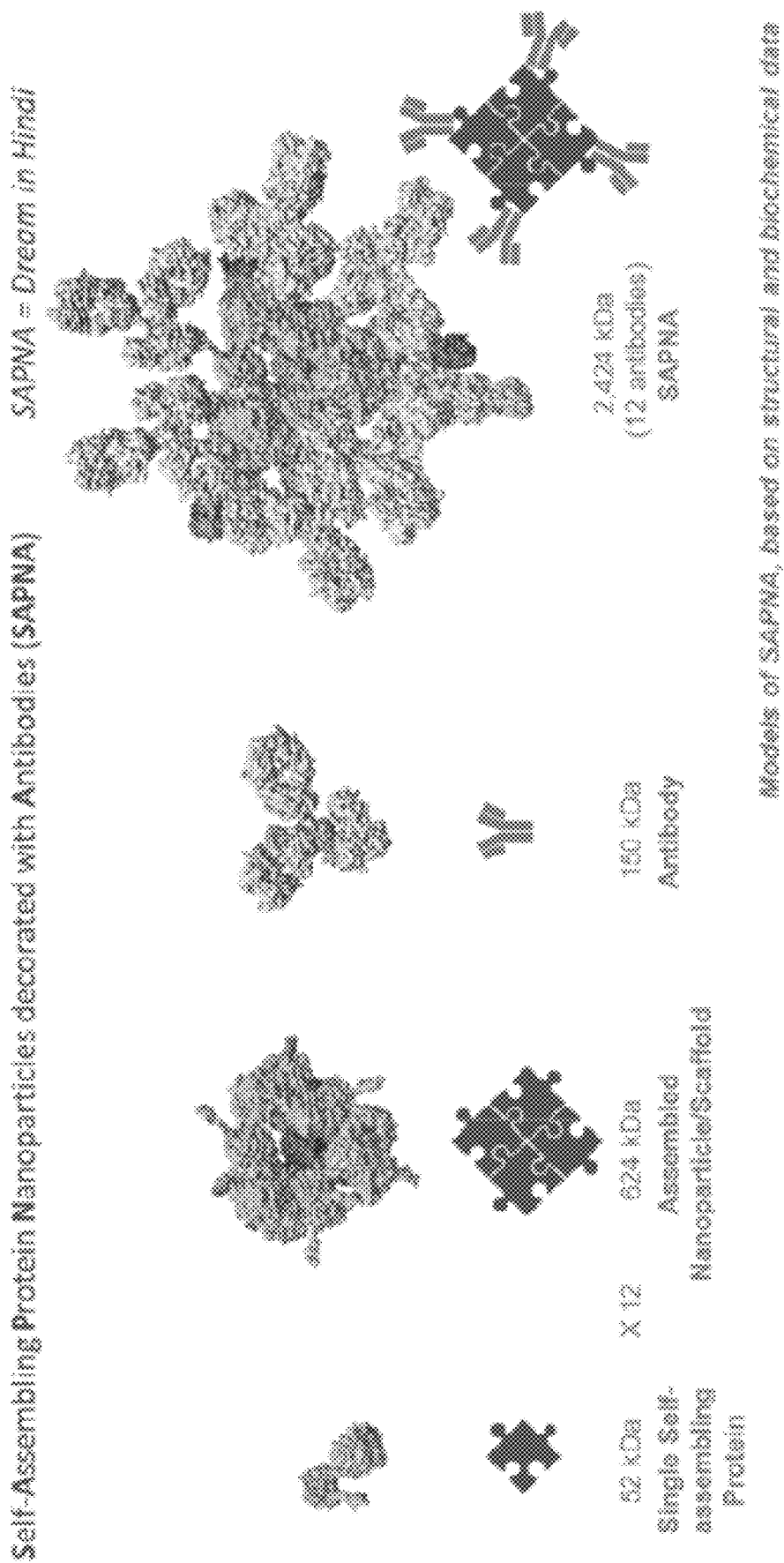
FIG. 7: SAPNA can be loaded with up to 12 antibodies.
Figure 8:
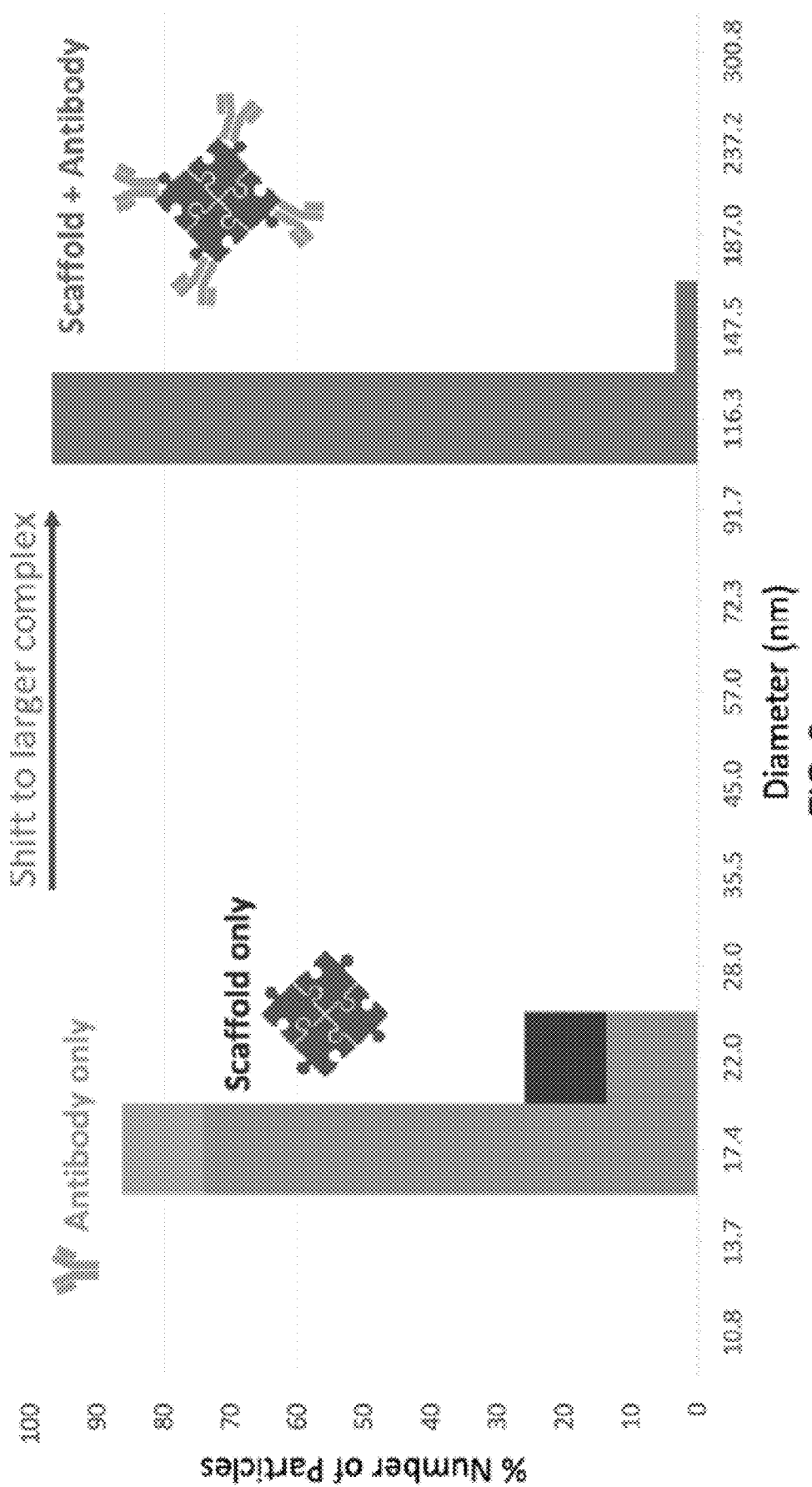
FIG. 8: Dynamic Light Scattering shows SAPNA loaded with a rabbit-anti-ROBO1 antibody.
Figure 9:
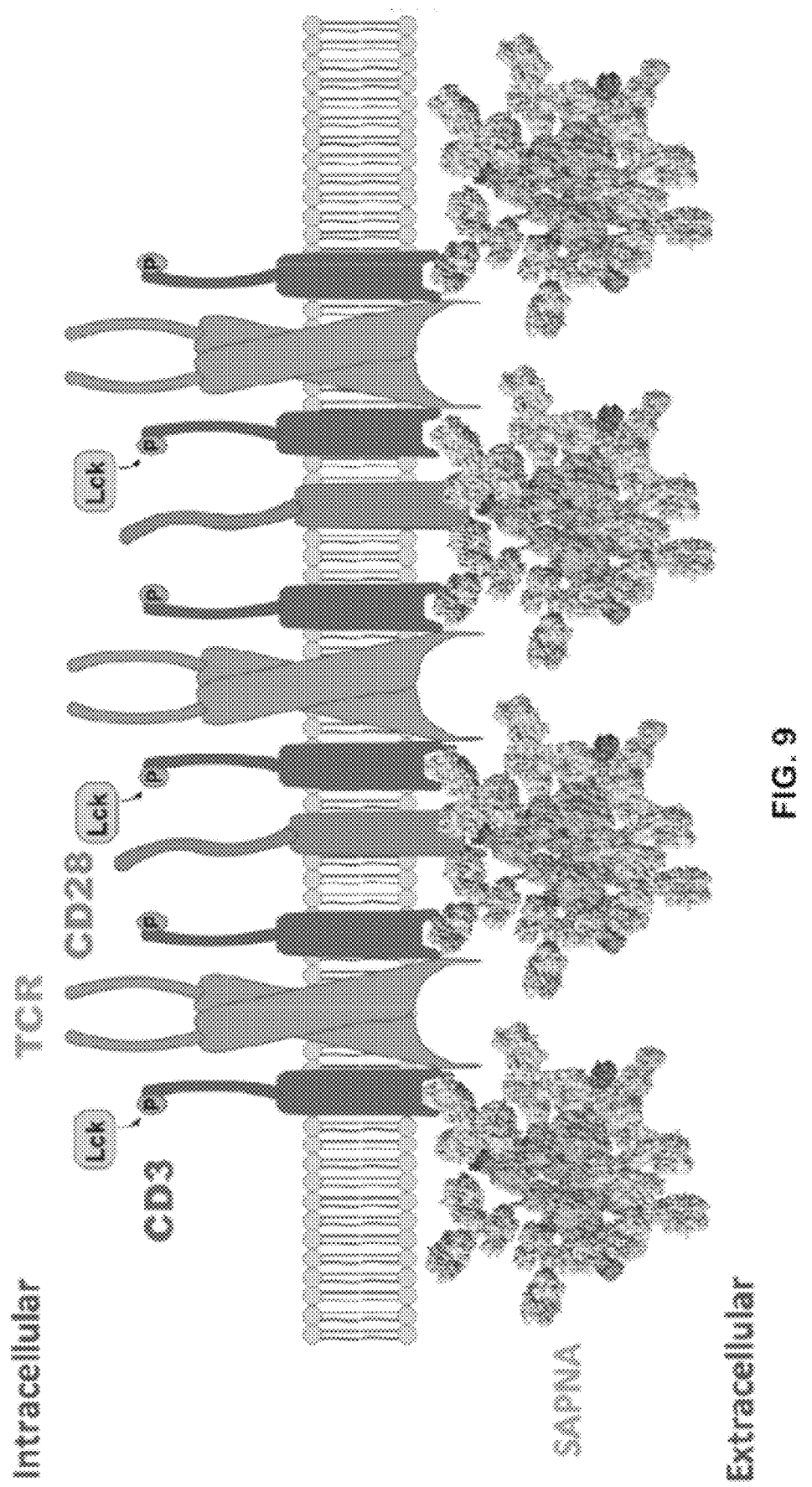
FIG. 9: Schematic of SAPNA enforcing receptor clustering at the T cell immunological synapse.

The SAPNA molecule has twelve potential antibody Fc binding sites and can mount any human or rabbit IgG (FIG. 7). Demonstrated herein is an example of SAPNA's abilities by binding it to a rabbit-anti-ROBO1 antibody (FIG. 8). SAPNA is hypothesized to physically force cell-surface receptors into close proximity, which is a required step in the activation and expansion of T cells (FIG. 9).

Figure 10:
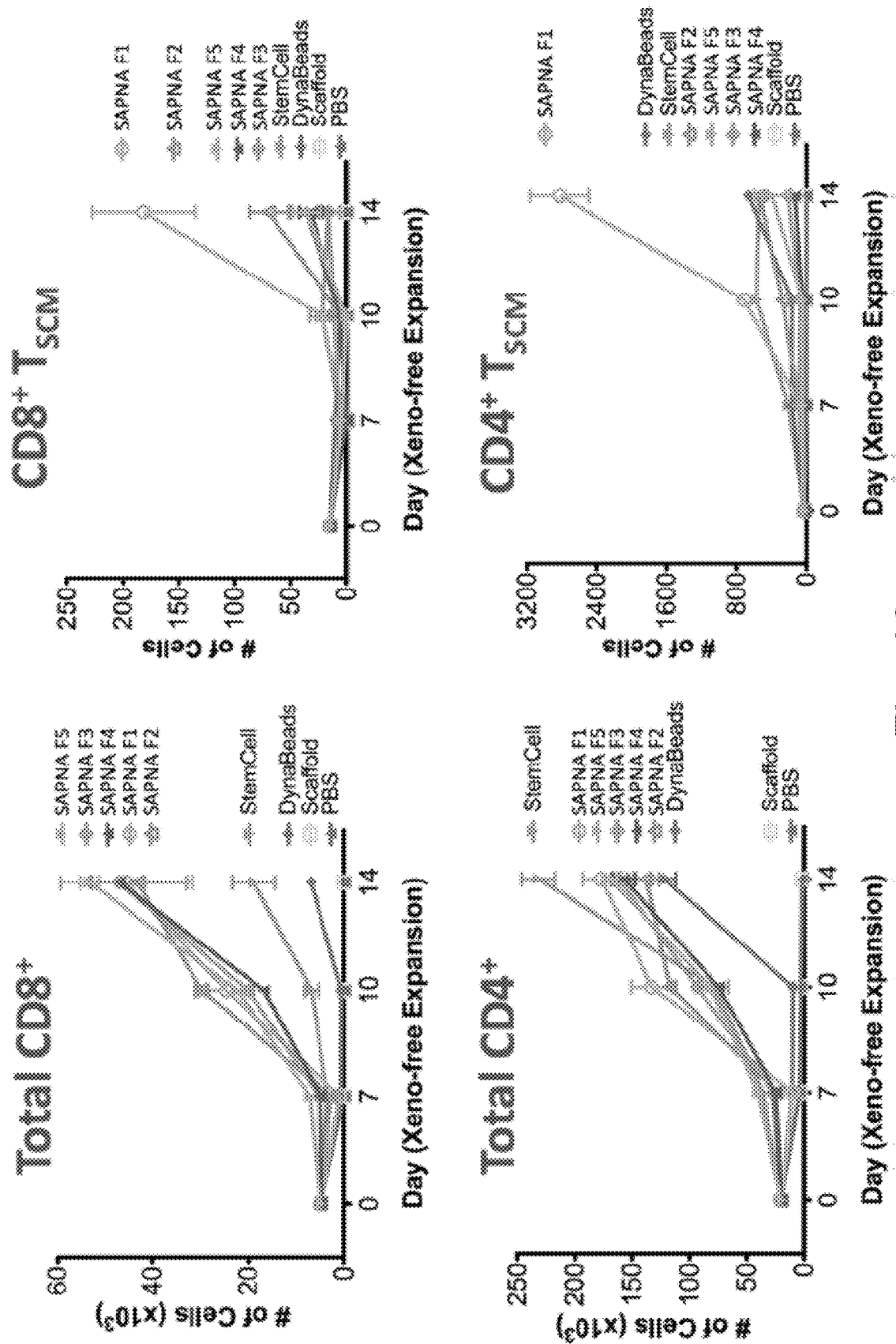
FIG. 10: SAPNA loaded with anti-CD3/anti-CD28 antibodies used to stimulate and expand blood donor-derived T cells over 14 days with flow cytometry as a readout. These data demonstrate superior primary T cell expansion abilities relative to two on-market technologies, ThermoFisher's Dynabeads CD3/CD28, and StemCell's ImmunoCult CD3/CD28.

To assess and benchmark SAPNA, 14-day T cell expansions were performed with clinically-relevant donor-derived peripheral blood T cells (FIG. 10). These data demonstrate that SAPNA produces a T cell product containing the highest number of cytotoxic CD8$^+$ T cells (FIG. 4—top left panel), which are the intended cells for engineering with chimeric antigen receptors (CARs) meant to target them to cancer cells. SAPNA performs in the top 2 for CD4$^+$ T cell expansion relative to competing technologies (FIG. 10—bottom left panel); these are an important component of the final CAR T cell product.

Additionally, it has been shown that T cell subsets with a more stem-like phenotype, such as memory stem ($T_{SCM}$) T cells, have the greatest long-term anti-cancer efficacy in vivo and it is therefore very therapeutically valuable to have increased numbers of these present in the final expanded CAR T cell product (Turtle, C. J. et al. CD19 CAR$^-$ T cells of defined CD4+:CD8+ composition in adult B cell ALL patients. *J. Clin. Invest.* 126, 2123-2138 (2016); Gattinoni, L. et al. Wnt signaling arrests effector T cell differentiation and generates CD8+ memory stem cells. *Nat. Med.* 15, 808-813 (2009)). The SAPNA technology produces the greatest number of CD4+ and CD8+ T$_{SCM}$ cells (FIG. 10—top & bottom right panels) during the expansion. Collectively, these data demonstrate that SAPNA is technically superior, and has the potential to generate greater numbers of CAR T cells with more efficacious anti-cancer activity.

Figure 11:
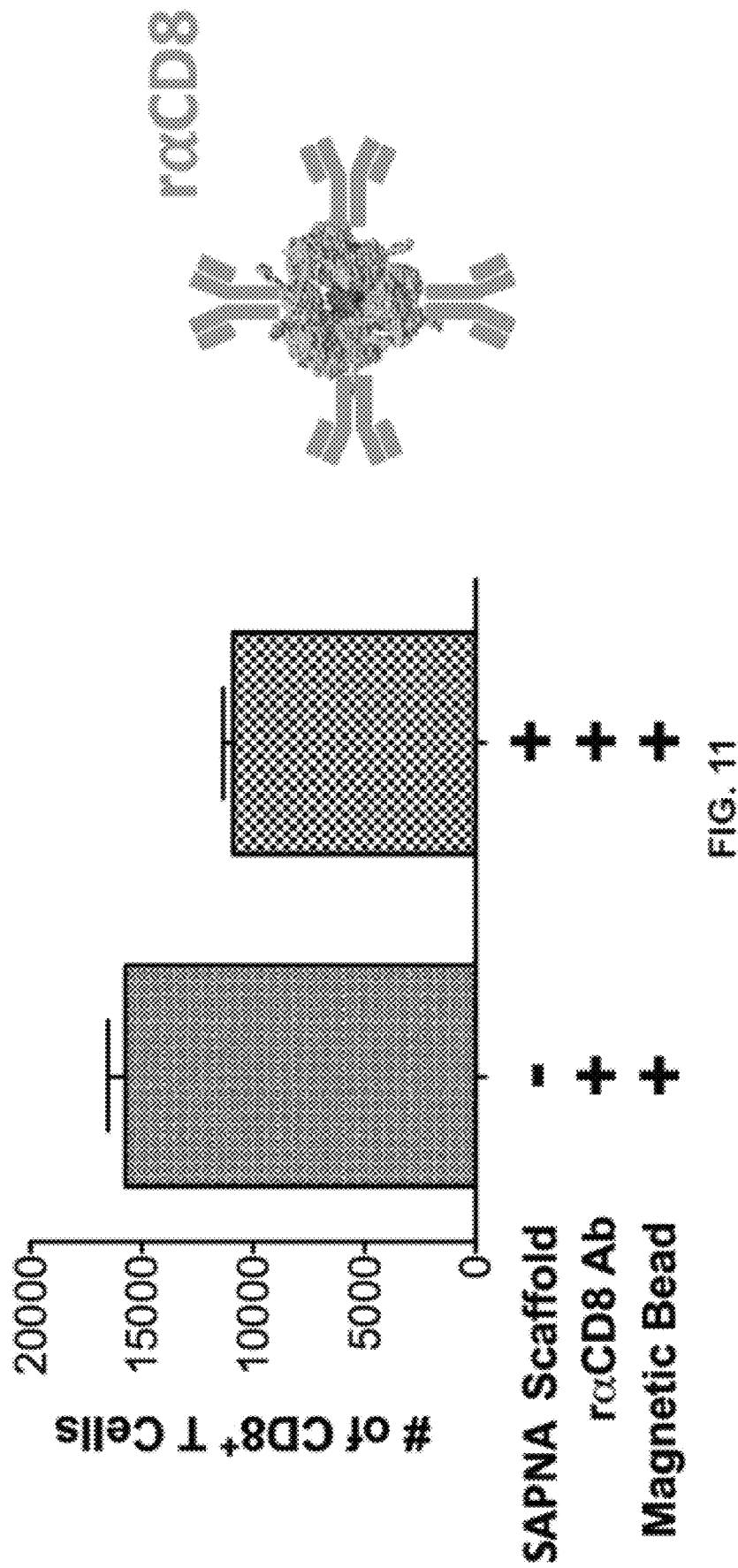
FIG. 11: SAPNA bound to beads can isolate (negatively select) T cell populations.

Due to the 12 his-tags on the SAPNA molecule (one on each monomer), it was hypothesized that it could bind to magnetic nickel beads, while also binding and displaying antibodies. Through this dual action, it has been demonstrated that SAPNA can be used to isolate (or negatively select) cell populations with a particular cell-surface marker, such as CD8, from a mixed group of cells (FIG. 11).

Figure 13:
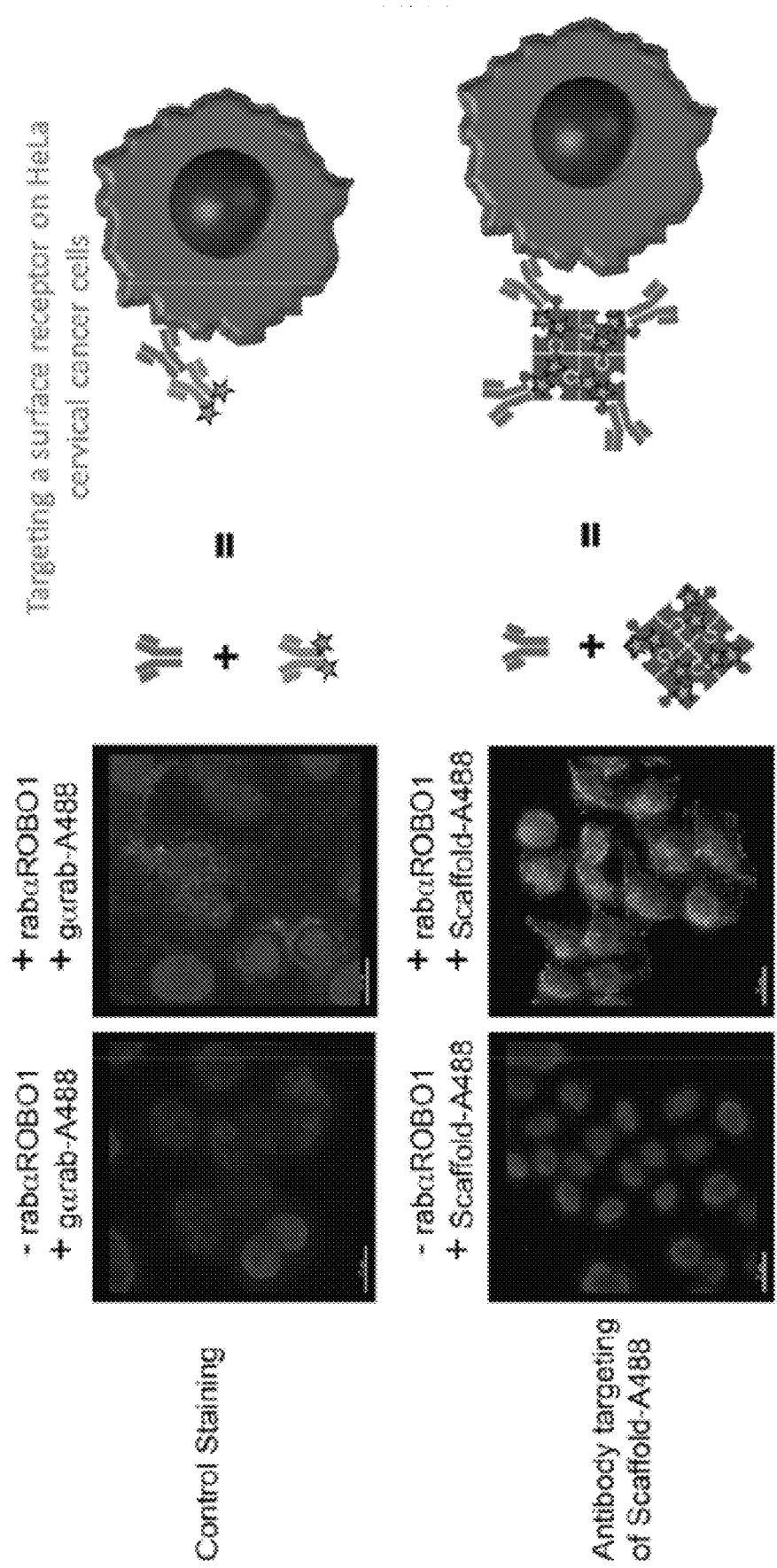
FIG. 13: Alexa Fluor®-488 labeled SAPNA binds to rabbit-anti-ROBO1 antibodies target to the surface of HeLa cervical cancer cells.

To evaluate if SAPNA could be targeted to the surface of cancer cells, immunofluorescence microscopy was employed. After using small angle X-ray scattering (SAXS) to validate that chemically labeling SAPNA with Alexa Fluor®-488 had little impact on its structure (FIG. 12), the labeled nanoparticle was targeted to the surface of HeLa cervical cancer cells by loading it with the same rabbit-anti-ROBO1 antibody as used for the DLS in FIG. 8. The 488-labeled SAPNA was specifically targeted to the surface of the cells (FIG. 13).

Example 3

Additional SAPNX Having Passenger Peptides

Despite the amino acid and positional restrictions indicated in FIG. 6, additional SAPNX carrying other passenger peptides were constructed using methods in the art. Specifically, passenger peptides that are cleaved by thrombin (i.e., LVPRGSG (SEQ ID NO: 53), which may or may not have a G at the N-terminus) or TEV protease (i.e., GSEN-LYFQGGS (SEQ ID NO: 54)) were inserted at various locations in the following scaffolding protein (bold indicates the positions of the insertions or substitutions):

(SEQ ID NO: 55)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTDRTLPIENTARVFHKALPSAEY

VEVEGAPHGLLWTHAEEVNTALLAFLAKAQEAQKQKLLTEVETYVLSIIP

SGPLKAEIAQRLEDVFAGKNTDLEVLMEWLKTRPILSPLTKGILGFVFTL

TVPSERGLQRRRFVQNALNGNGDPNNMDKAVKLYRKLKREITFHGAKEIS

LSYSAGALASCMGLIYNRMGAVTTEVAFGLV which further comprised (SEQ ID NO: 56)
CATCEQIADSQHRSHRQLEHHHHHH covalently attached to the C-terminus.

The resulting exemplary SAPNX include (bold font indicates the inserted passenger protein):

M1—Insertion after Amino Acid Residue 302

(SEQ ID NO: 57)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTDRTLPIENTARVFHKALPSAEY

VEVEGAPHGLLWTHAEEVNTALLAFLAKAQEAQKQKLLTEVETYVLSIIP

SGLVPRGSGPLKAEIAQRLEDVFAGKNTDLEVLMEWLKTRPILSPLTKGI

LGFVFTLTVPSERGLQRRRFVQNALNGNGDPNNMDKAVKLYRKLKREITF

HGAKEISLSYSAGALASCMGLIYNRMGAVTTEVAFGLVCATCEQIADSQH

RSHRQHHHHHH

M2—Insertion after Amino Acid Residue 139

(SEQ ID NO: 58)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGLVPRGSGAAPQ

EFFDGIVAAVKADRYAFYTGFFNDFYNLDENLGTRISEEAVRNSWNTAAS

GGFFAAAAAPTTWYTDFRADIPRIDVPALILHGTDRTLPIENTARVFHK

ALPSAEYVEVEGAPHGLLWTHAEEVNTALLAFLAKAQEAQKQKLLTEVET

YVLSIIPSGPLKAEIAQRLEDVFAGKNTDLEVLMEWLKTRPILSPLTKGI

LGFVFTLTVPSERGLQRRRFVQNALNGNGDPNNMDKAVKLYRKLKREITF

HGAKEISLSYSAGALASCMGLIYNRMGAVTTEVAFGLVCATCEQIADSQH

RSHRQHHHHHH

M4—Insertion after Amino Acid Residue 255

(SEQ ID NO: 59)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTDRTLPIENTARVFHKALPSAEY

VEVELVPRGSGAPHGLLWTHAEEVNTALLAFLAKAQEAQKQKLLTEVET

YVLSIIPSGPLKAEIAQRLEDVFAGKNTDLEVLMEWLKTRPILSPLTKGI

LGFVFTLTVPSERGLQRRRFVQNALNGNGDPNNMDKAVKLYRKLKREITF

HGAKEISLSYSAGALASCMGLIYNRMGAVTTEVAFGLVCATCEQIADSQH

RSHRQHHHHHH

M10—Insertion after Amino Acid Residue 247

(SEQ ID NO: 60)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTGDRTLPIENTARVFHKALPGLVP

RGSGSAEYVEVEGAPHGLLWTHAEEVNTALLAFLAKAQEAQKQKLLTEVE

TYVLSIIPSGPLKAEIAQRLEDVFAGKNTDLEVLMEWLKTRPILSPLTKG

ILGFVFTLTVPSERGLQRRRFVQNALNGNGDPNNMDKAVKLYRKLKREIT

FHGAKEISLSYSAGALASCMGLIYNRMGAVTTEVAFGLVCATCEQIADSQ

HRSHRQHHHHHH

M13—Substitution of Amino Acid Residues 353-355

(SEQ ID NO: 61)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTGDRTLPIENTARVFHKALPSAEY

VEVEGAPHGLLWTHAEEVNTALLAFLAKAQEAQKQKLLTEVETYVLSIIP

SGPLKAEIAQRLEDVFAGKNTDLEVLMEWLKTRPILSPLTKGILGFVFTL

TGLVPRGSGERGLQRRRFVQNALNGNGDPNNMDKAVKLYRKLKREITFHG

AKEISLSYSAGALASCMGLIYNRMGAVTTEVAFGLVCATCEQIADSQHRS

HRQHHHHHH

M1-TEV—Insertion after Amino Acid Residue 302

(SEQ ID NO: 62)
MPFITVGQENSTSIDLYYEDHGTGTPVVLIHGFPLSGHSWERQSAALLDA

GARVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTGDRTLPIENTARVFHKALPSAEY

VEVEGAPHGLLWTHAEEVNTALLAFLAKAQEAQKQKLLTEVETYVLSIIP

SGGSENLYFQGGSPLKAEIAQRLEDVFAGKNTDLEVLMEWLKTRPILSPL

TKGILGFVFTLTVPSERGLQRRRFVQNALNGNGDPNNMDKAVKLYRKLKR

EITFHGAKEISLSYSAGALASCMGLIYNRMGAVTTEVAFGLVCATCEQIA

DSQHRSHRQLEHHHHHH

M14-TEV—Substitution of Amino Acids Residues 23-24

(SEQ ID NO: 63)
MPFITVGQENSTSIDLYYEDHGGSENLYFQGGSTPVVLIHGFPLSGHSWE

RQSAALLDAGARVITYDRRGFGQSSQPTTGYDYDTFAADLNTVLETLDLQ

DAVLVGFSMGTGEVARYVSSYGTARIAAVAFLASLEPFLLKTDDNPDGAA

PQEFFDGIVAAVKADRYAFYTGFFNDFYNLDENLGTRISEEAVRNSWNTA

ASGGFFAAAAAPTTWYTDFRADIPRIDVPALILHGTGDRTLPIENTARVF

HKALPSAEYVEVEGAPHGLLWTHAEEVNTALLAFLAKAQEAQKQKLLTEV

ETYVLSIIPSGPLKAEIAQRLEDVFAGKNTDLEVLMEWLKTRPILSPLTK

GILGFVFTLTVPSERGLQRRRFVQNALNGNGDPNNMDKAVKLYRKLKREI

TFHGAKEISLSYSAGALASCMGLIYNRMGAVTTEVAFGLVCATCEQIADS

QHRSHRQLEHHHHHH

Computational Design

Protein cages were engineered using the crystal structure of the one-component tetrahedral protein cage known as PC-quad (SEQ ID NO: 64, wherein X is A) as a starting design model. Protein sequences on the surface of protein cages were assessed for engineering potential based on secondary structure (e.g., loops between alpha helices and/or beta strands), and degree of exterior solvent accessibility. Mutant cage designs were generated by inserting thrombin recognition sites or TEV protease recognition sites into identified target locations. Genes were synthesized for making insertions at ten different sites (M1, M2, M4, M5, M9, M10, M11, M12, M13, and M14/M14-TEV). Six of the cloned genes were tested for experimental production of cages by biochemical characterization (M1, M2, M4, M10, M13, and M14-TEV).

Protein Expression and Purification

Genes corresponding to the mutant and wild-type protein cages containing restriction enzyme sites were synthesized by and purchased from Integrated DNA Technologies (IDT) in high purity. Genes were cloned into the PSB1C3 expression plasmid carrying the chloramphenicol resistance gene. Sanger sequencing-confirmed mutants were transformed into BL21 E. coli cells (New England Biolabs), and grown overnight in 5 mL of LB broth supplemented with chloramphenicol. 350 mL cultures of LB and antibiotic were inoculated with overnight starter culture and grown at 37° C. until an $OD_{600}$ of 0.6 was reached. 0.5 mm IPTG was used to induce protein expression for 4 hours at 37° C. Cells were harvested by centrifugation at 4000×g for 20 minutes at for degrees Celsius.

Cells were lysed by sonication in 20 mM Sodium Phosphate Buffer pH 8.0, 300 mM NaCl, 10 mM imidazole. Proteins were purified using His-pure Ni-affinity resin (Thermo Fisher Scientific), and eluted using lysis buffer supplemented with 500 mM imidazole. Protein was dialyzed overnight into 20 mM TRIS pH 8.0, 100 mM NaCl, 2 mM beta-mercaptoethanol. SDS-PAGE was used to confirm protein purity and solubility after affinity purification. Dynamic light scattering (DLS) was performed in a Dynapro Plate Reader II DLS (Wyatt Technology) on purified samples at a concentration of 1 mg/ml to confirm proper assembly and degree of monodispersity of purified protein cages.

Characterization of Specific Cage Constructs

Figure 14:
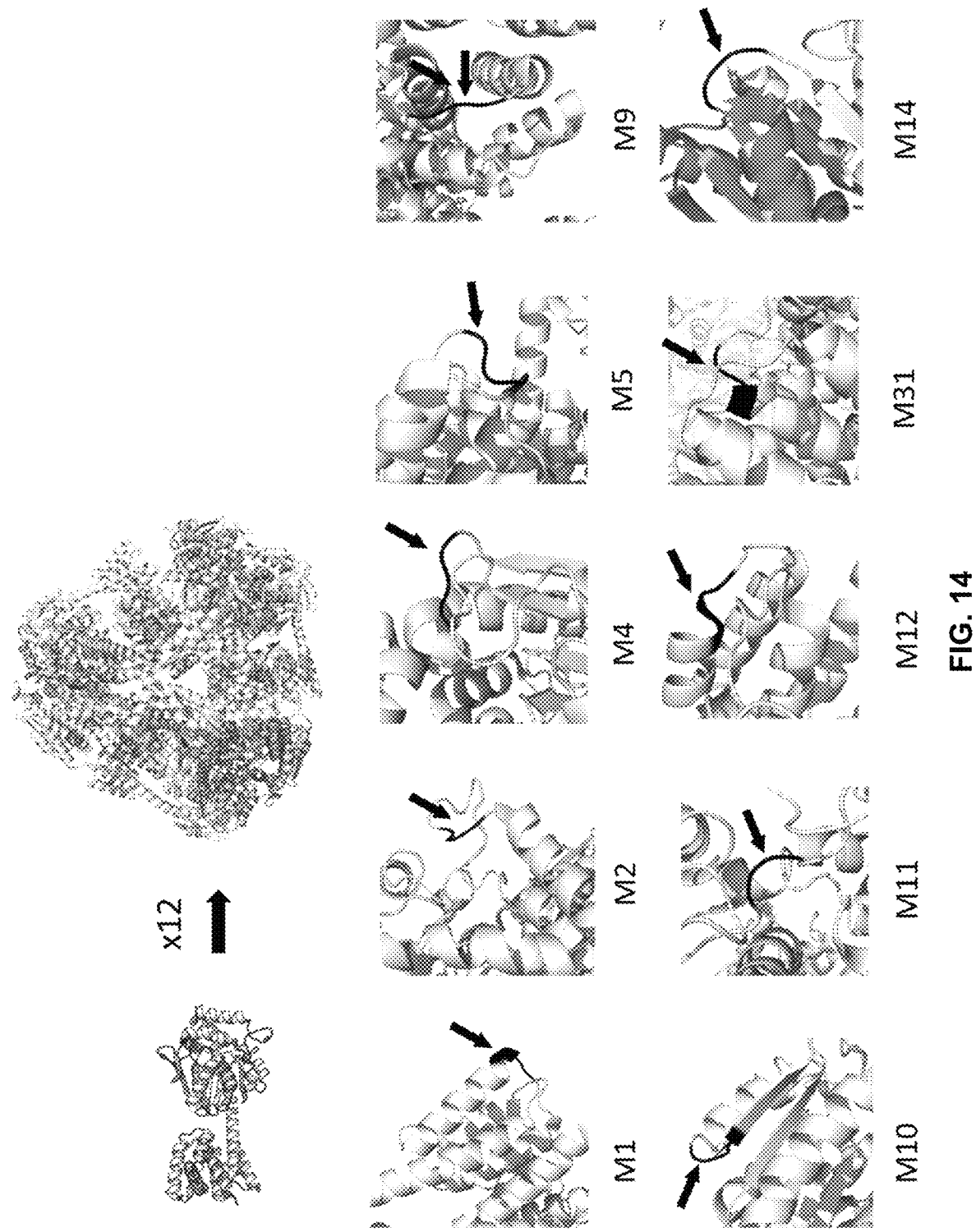
FIG. 14: Shows protein modeling of exemplary SAPNX and insertion sites for passenger peptides.

Among the constructs tested biochemically, M1, M13, and M14-TEV showed good expression and purification from E. coli based on nickel-affinity purification and SDS (FIG. 14).

Figure 15:
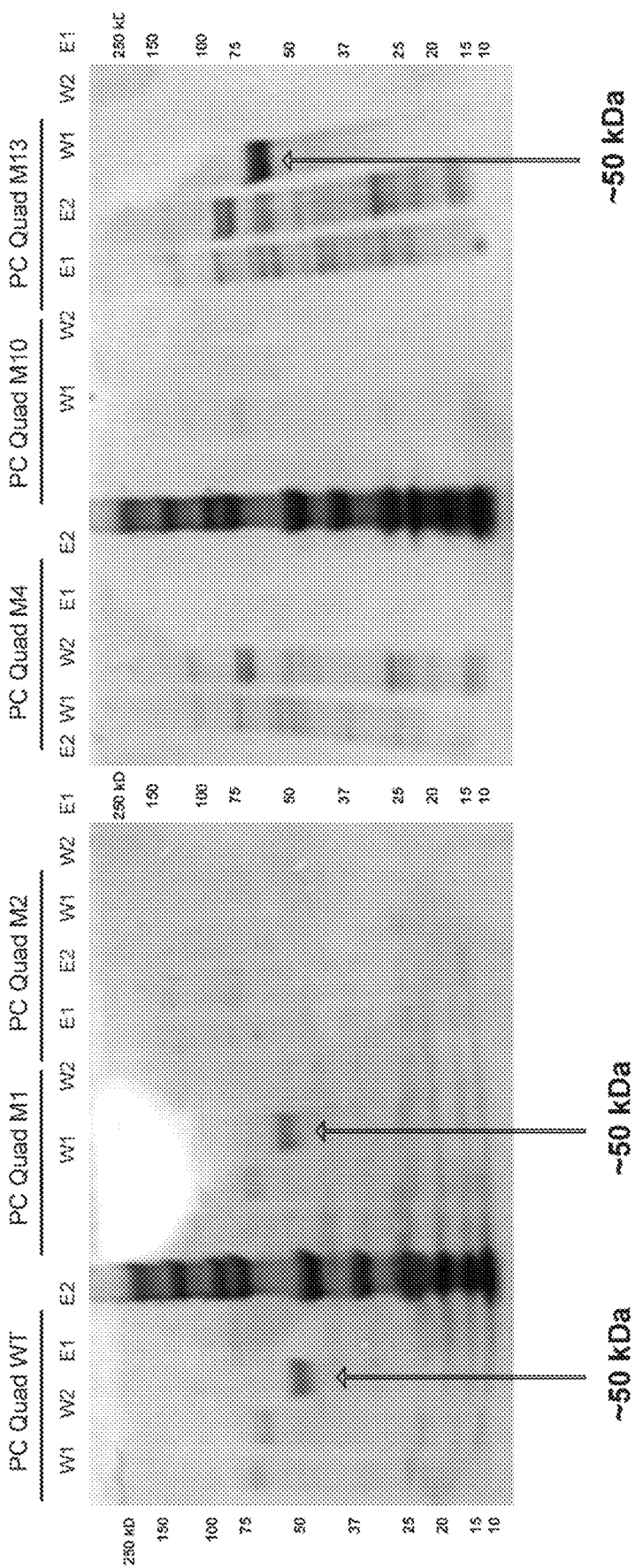
FIG. 15: SDS gels of M1 and M13 SAPNX constructs.

Based on dynamic light scattering, constructs M1 showed assembly into the large cage form as a dominant species (FIG. 15). M13 showed formation of large cage structures, but as a lesser component among other species.

Figure 16:
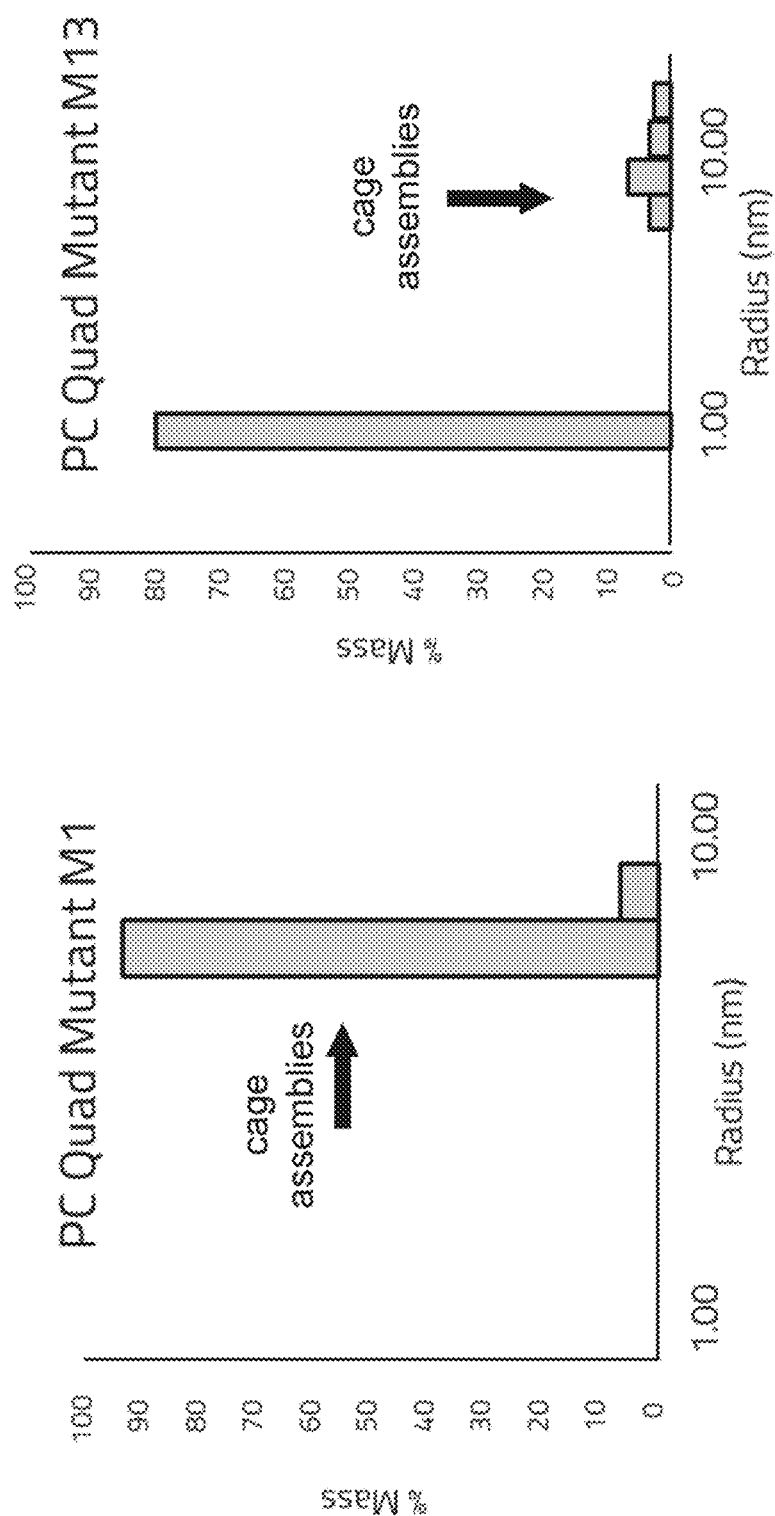
FIG. 16: Dynamic light scattering results demonstrating cage assembly for M1 and M13 SAPNX constructs.

M1 and M14-TEV were both further examined by size exclusion chromatography (SEC) (FIG. 16). There the elution patterns showed a single dominant cage species for the M1 purification and species in the correct size range for the large cage assembly among a heterogeneous assembly population in the case of M14-TEV. The purified M1 construct was also visualized by negative stain electron microscopy (FIG. 17).

Proteolysis Assays

In experiments to test for proteolytic sensitivity of various PC-cage insertion constructions, purified protein cages at a concentration of 1 mg/ml were mixed with thrombin from bovine plasma (Sigma-Aldrich) at a ratio of 1.3 mg protein/unit thrombin in a total reaction volume of 200 μL. Cleavage reactions were carried out at 22° C. for 16 hours without mixing. SDS-PAGE was used to confirm cleavage of target protein. DLS was subsequently used to characterize the size distribution of proteins in solution to confirm disruption of SAPNX by specific protease treatment.

REFERENCES

The following references are herein incorporated by reference in their entirety with the exception that, should the scope and meaning of a term conflict with a definition explicitly set forth herein, the definition explicitly set forth herein controls:

A. B. Sigalov, The SCHOOL of nature: I. Transmembrane signaling. Self Nonself 1, 4-39 (2010).

C. D. Putnam, M. Hammel, G. L. Hura, J. A. Tainer, X-ray solution scattering (SAXS) combined with crystallography and computation:defining accurate macromolecular structures, conformations and assemblies in solution. Q. Rev. Biophys. 40, 191-285 (2007).

C. Spiess, Q. Zhai, P. J. Carter, Alternative molecular formats and therapeutic applications for bispecific antibodies. Mol. Immunol. 67, 95-106 (2015).

D. M. Ecker, S. D. Jones, H. L. Levine, The therapeutic monoclonal antibody market. MAbs 7, 9-14 (2015).

D. W. LaFleur et al., Monoclonal antibody therapeutics with up to five specificities: functional enhancement through fusion of target-specific peptides. MAbs 5, 208-218 (2013).

G. A. Lazar et al., Engineered antibody Fc variants with enhanced effector function. Proc. Natl. Acad. Sci. U.S.A. 103, 4005-4010 (2006).

H. Byrne, P. J. Conroy, J. C. Whisstock, R. J. O'Kennedy, A tale of two specificities: bispecific antibodies for therapeutic and diagnostic applications. Trends Biotechnol. 31, 621-632 (2013).

H. J. Kang et al., Developing an antibody-binding protein cage as a molecular recognition drug modular nanoplatform. Biomaterials 33, 5423-5430 (2012).

J. E. Padilla, C. Colovos, T. O. Yeates, Nanohedra: using symmetry to design self assembling protein cages, layers, crystals, and filaments. Proc. Natl. Acad. Sci. U.S.A. 98, 2217-2221 (2001).

J. Stieglmaier, J. Benjamin, D. Nagorsen, Utilizing the BiTE (bispecific T-cell engager) platform for immunotherapy of cancer. Expert Opin Biol Ther 15, 1093-1099 (2015).

M. Suzuki, C. Kato, A. Kato, Therapeutic antibodies: their mechanisms of action and the pathological findings they induce in toxicity studies. J Toxicol Pathol 28, 133-139 (2015).

N. Dimasi et al., Development of a Trispecific Antibody Designed to Simultaneously and Efficiently Target Three Different Antigens on Tumor Cells. Mol. Pharm. 12, 3490-3501 (2015).

R. Mathaes, H. C. Mahler. Next Generation Biopharmaceuticals: Product Development. Adv Biochem Eng Biotechnol. 165, 253-276 (2018).

T. O. Yeates, Y. Liu, J. Laniado. The design of symmetric protein nanomaterials comes of age in theory and practice. Curr Opin Struct Biol. 39, 134-143 (2016).

W. Choe, T. A. Durgannavar, S. J. Chung, Fc-Binding Ligands of Immunoglobulin G: An Overview of High Affinity Proteins and Peptides. Materials (Basel) 9, (2016).

W. L. DeLano, M. H. Ultsch, A. M. de Vos, J. A. Wells, Convergent solutions to binding at a protein-protein interface. Science 287, 1279-1283 (2000).

Y. Gong, L. Zhang, J. Li, S. Feng, H. Deng, Development of the Double Cyclic Peptide Ligand for Antibody Purification and Protein Detection. Bioconjug Chem 27, 1569-1573 (2016).

Y. J. Kang et al., Polyvalent display of monosaccharides on ferritin protein cage nanoparticles for the recognition and binding of cell-surface lectins. Macromol. Biosci. 14, 619-625 (2014).

Y. T. Lai et al., Designing and defining dynamic protein cage nanoassemblies in solution. Sci Adv 2, e1501855 (2016).

Y. T. Lai, D. Cascio, T. O. Yeates, Structure of a 16-nm cage designed by using protein oligomers. Science 336, 1129 (2012).

Y. T. Lai, K. L. Tsai, M. R. Sawaya, F. J. Asturias, T. O. Yeates, Structure and flexibility of nanoscale protein cages designed by symmetric self-assembly. J. Am. Chem. Soc. 135, 7738-7743 (2013).

H. Byrne, P. J. Conroy, J. C. Whisstock, R. J. O'Kennedy, A tale of two specificities: bispecific antibodies for therapeutic and diagnostic applications. Trends Biotechnol. 31, 621 632 (2013).

T. Uchanski, E. Pardon, J. Steyaert. Nanobodies to study protein conformational states. Curr. Opin. Struct. Biol., 60, 117-123 (2020).

R. J. Hoey, H. Eom, J. R. Horn. Structure and development of single domain antibodies as modules for therapeutics and diagnostics. Exp Biol Med 244, 1568-1576 (2019).

P. Mittl, P. Ernst, A. Plueckthun. Chaperone-assisted structure elucidation with DARPins. Curr. Opin. Struct. Biol., 60, 93-100 (2020).

S. A. McConnell, K. A. Cannon, C. Morgan, R. McAllister, B. R. Amer, R. T. Clubb, T. O. Yeates. Designed Protein Cages as Scaffolds for Building Multienzyme Materials. ACS Synth Biol. 9, 381-391 (2020).

C. G. England, H. Luo, W. Cai. HaloTag Technology: A Versatile Platform for Biomedical Applications. Bioconjug Chem. 26, 975-986 (2015).

A. F. Hussain, M. Amoury, S. Barth. SNAP-tag technology: a powerful tool for site specific conjugation of therapeutic and imaging agents. Curr Pharm Des 19, 5437-42 (2013).

M. Fairhead and M. Howarth. Site-specific biotinylation of purified proteins using BirA. Methods Mol Biol. 1266, 171-184 (2015).

S. C. Reddington and M. Howarth. Secrets of a covalent interaction for biomaterials and biotechnology: SpyTag and SpyCatcher. Curr Opin Chem Biol., 29, 94-9 (2015).

Nicell, J. (2001) Interdisciplinary Environmental Review 2001 3(1): 14-41. McConnell, et al. ACS Synth Biol. 9, 381-391 (2020).

All scientific and technical terms used in this application have meanings commonly used in the art unless otherwise specified.

The use of the singular can include the plural unless specifically stated otherwise. As used in the specification and the appended claims, the singular forms "a", "an", and "the" can include plural referents unless the context clearly dictates otherwise.

As used herein, "and/or" means "and" or "or". For example, "A and/or B" means "A, B, or both A and B" and "A, B, C, and/or D" means "A, B, C, D, or a combination thereof" and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

As used herein, the phrase "one or more of", e.g., "one or more of A, B, and/or C" means "one or more of A", "one or more of B", "one or more of C", "one or more of A and one or more of B", "one or more of B and one or more of C", "one or more of A and one or more of C" and "one or more of A, one or more of B, and one or more of C".

As used herein, the phrase "consists essentially of" in the context of a given ingredient in a composition, means that the composition may include additional ingredients so long as the additional ingredients do not adversely impact the activity, e.g., biological or pharmaceutical function, of the given ingredient.

The phrase "comprises, consists essentially of, or consists of A" is used as a tool to avoid excess page and translation fees and means that in some embodiments the given thing at issue: comprises A, consists essentially of A, or consists of A. For example, the sentence "In some embodiments, the composition comprises, consists essentially of, or consists of A" is to be interpreted as if written as the following three separate sentences: "In some embodiments, the composition comprises A. In some embodiments, the composition consists essentially of A. In some embodiments, the composition consists of A."

Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C." As another example, the sentence "In some embodiments, the composition comprises at least A, B, or C" is to be interpreted as if written as the following three separate sentences: "In some embodiments, the composition comprises at least A. In some embodiments, the composition comprises at least B. In some embodiments, the composition comprises at least C."

As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus. Except when specifically indicated, peptides are indicated with the N-terminus on the left and the sequences are written from the N-terminus to the C-terminus. Similarly, except when specifically indicated, nucleic acid sequences are indicated with the 5' end on the left and the sequences are written from 5' to 3'.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

As used herein, a given percentage of "sequence identity" refers to the percentage of nucleotides or amino acid residues that are the same between sequences, when compared and optimally aligned for maximum correspondence over a given comparison window, as measured by visual inspection or by a sequence comparison algorithm in the art, such as the BLAST algorithm, which is described in Altschul et al., (1990) J Mol Biol 215:403-410. Software for performing BLAST (e.g., BLASTP and BLASTN) analyses is publicly available through the National Center for Biotechnology Information (ncbi.nlm.nih.gov). The comparison window can exist over a given portion, e.g., a functional domain, or an arbitrarily selection a given number of contiguous nucleotides or amino acid residues of one or both sequences. Alternatively, the comparison window can exist over the full length of the sequences being compared. For purposes herein, where a given comparison window (e.g., over 80% of the given sequence) is not provided, the recited sequence identity is over 100% of the given sequence. Additionally, for the percentages of sequence identity of the proteins provided herein, the percentages are determined using BLASTP 2.8.0$^+$, scoring matrix BLOSUM62, and the default parameters available at blast.ncbi.nlm.nih.gov/Blast.cgi. See also Altschul, et al., (1997) Nucleic Acids Res 25:3389-3402; and Altschul, et al., (2005) FEBS J 272: 5101-5109.

Optimal alignment of sequences for comparison can be conducted, e.g., by the local homology algorithm of Smith & Waterman, Adv Appl Math 2:482 (1981), by the homology alignment algorithm of Needleman & Wunsch, J Mol Biol 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "cell" or "cells" refers to any cells of any organism, ranging from single celled organisms to mammalian cells, in vitro or in vivo. The term "host cell" is used herein to refer to a living biological cell that can be transformed via insertion of an expression vector.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A polypeptide comprising (a) a scaffolding protein consisting of an amino acid sequence having 100% sequence identity to SEQ ID NO: 64, (b) a passenger peptide covalently linked thereto, wherein (i) the passenger peptide is a peptide tag, a covalent peptide tag, a protein tag, an enzyme, or an enzyme substrate, and the passenger peptide neither comprises nor consists of SEQ ID NO: 41 or SEQ ID NO: 42, and/or (ii) the passenger peptide is covalently linked to an amino acid selected from the group consisting of: residues 19-26, 131-141, 245-257, 300-304, and 350-357 of SEQ ID NO: 64 or replaces one or more amino acids selected from the group consisting of: residues 19-26, 131-141, 245-257, 300-304, and 350-357 of SEQ ID NO: 64; and (c) optionally, a peptide having a sequence selected from the group consisting of SEQ ID NO: 45, SEQ ID NO: 52, and SEQ ID NO: 56 covalently attached to a terminal end of the scaffolding protein.

2. The polypeptide according to claim 1, wherein the polypeptide comprises the peptide having SEQ ID NO: 45 covalently attached to the terminal end of the scaffolding protein.

3. The polypeptide according to claim 1, wherein the polypeptide does not contain the peptide having SEQ ID NO: 45 covalently attached to the terminal end of the scaffolding protein.

4. The polypeptide according to claim 1, wherein the polypeptide comprises the peptide having SEQ ID NO: 52 covalently attached to the terminal end of the scaffolding protein.

5. The polypeptide according to claim 1, wherein the polypeptide comprises the peptide having SEQ ID NO: 56 covalently attached to the terminal end of the scaffolding protein.

6. The polypeptide according to claim 1, wherein the passenger peptide is covalently linked to the amino acid selected from the group consisting of: residues 19-26, 131-141, 245-257, 300-304, and 350-357 of SEQ ID NO: 64.

7. The polypeptide according to claim 1, wherein the passenger peptide replaces one or more amino acids selected from the group consisting of: residues 19-26, 131-141, 245-257, 300-304, and 350-357 of SEQ ID NO: 64.

8. The polypeptide according to claim 1, wherein the passenger peptide is covalently linked to residue 19, 20, 21, 22, 23, 24, 25, 26, 131, 132, 133, 134, 135, 136, 137, 138, 139, 140, 141, 245, 246, 247, 248, 249, 253, 254, 255, 256, 257, 300, 301, 302, 303, 304, 350, 351, 352, 353, 354, 355, 356, or 357 of SEQ ID NO: 64 or replaces one or more amino acids selected from the group consisting of: residues 19, 20, 21, 22, 23, 24, 25, 26, 131, 132, 133, 134, 135, 136, 137, 138, 139, 140, 141, 245, 246, 247, 248, 249, 253, 254, 255, 256, 257, 300, 301, 302, 303, 304, 350, 351, 352, 353, 354, 355, 356, and 357 of SEQ ID NO: 64.

9. The polypeptide according to claim 1, wherein the passenger peptide is covalently linked to residue residues 22, 23, 24, 25, 139, 238, 244, 245, 246, 301, 302, 303, 352, 353, 354, 355, or 356 or replaces one or more amino acids selected from the group consisting of: residues 22, 23, 24, 25, 139, 238, 244, 245, 246, 301, 302, 303, 352, 353, 354, 355, and 356 of SEQ ID NO: 64.

10. The polypeptide according to claim 1, wherein the polypeptide comprises the passenger peptide which is a peptide tag, a covalent peptide tag, a protein tag, an enzyme, or an enzyme substrate.

11. The polypeptide according to claim 1, wherein the passenger peptide binds another molecule or is cleaved by an enzyme.

12. The polypeptide according to claim 1, wherein the passenger peptide is an enzyme that is a narrow-specificity protease, whose recognition sequence depends on two or more amino acid positions.

13. The polypeptide according to claim 1, wherein the passenger peptide is an enzyme that is a protease such as thrombin or TEV protease.

14. The polypeptide according to claim 1, wherein the passenger peptide comprises or consists of LVPRGSG (SEQ ID NO: 53), GSENLYFQGGS (SEQ ID NO: 54), LPXTG (SEQ ID NO: 65), AHIVMVDAYKPTK (SEQ ID NO: 66), ATHIKFSKRD (SEQ ID NO: 67), CCPGCC (SEQ ID NO: 68), DIPATYEFTDGKHYITNEPIPPK (SEQ ID NO: 69), DLYDDDDK (SEQ ID NO: 70), DPIVMIDNDKPIT (SEQ ID NO: 71), DYKDDDDK (SEQ ID NO: 72), EEEEEE (SEQ ID NO: 73), EQKLISEEDL (SEQ ID NO: 74), EVHTNQDPLD (SEQ ID NO: 75), GAPVPYPDPLEPR (SEQ ID NO: 76), GKPIPNPLLGLDST (SEQ ID NO: 77), GLNDIFEAQKIEWHE (SEQ ID NO: 78), KETAAAKFERQHMDS (SEQ ID NO: 79), KLGDIEFIKVNK (SEQ ID NO: 80), KLGSIEFIKVNK (SEQ ID NO: 81), KRRWKKNFIAVSAANRFKKISSSGAL (SEQ ID NO: 82), MASMTGGQQMG (SEQ ID NO: 83), MDEKTTGWRGGHVVEGLAGELEQLRAR-LEHHPQGQREP (SEQ ID NO: 84), PDRVRAVSHWSS (SEQ ID NO: 85), SLAELLNAGLGGS (SEQ ID NO: 86), SRLEEELRRRLTE (SEQ ID NO: 87), TDKDM-TITFTNKKDAE (SEQ ID NO: 88), TETSQVAPA (SEQ ID NO: 89), TKENPRSNQEESYDDNES (SEQ ID NO: 90), TQDPSRVG (SEQ ID NO: 91), VPTIVMVDAYKRYK (SEQ ID NO: 92), WSHPQFEK (SEQ ID NO: 93), YPYDVPDYA (SEQ ID NO: 94), or YTDIEMNRLGK (SEQ ID NO: 95).

15. The polypeptide according to claim 1, wherein the passenger peptide neither comprises nor consists of SEQ ID NO: 41 or SEQ ID NO: 42.

* * * * *

SEQUENCE LISTING

```
<160> NUMBER OF SEQ ID NOS: 95

<210> SEQ ID NO 1
<211> LENGTH: 472
<212> TYPE: PRT
<213> ORGANISM: Artificial Sequence
<220> FEATURE:
<223> OTHER INFORMATION: SAPNA sequence
```

<400> SEQUENCE: 1

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Cys Asp Cys Ala Trp His Leu Gly Glu Leu
    130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Glu Ala Gln Lys Gln Lys Leu Leu
    290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365

Pro Ser Glu Arg Gly Leu Gln Arg Arg Phe Val Gln Asn Ala Leu
    370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
```

```
                        405                 410                 415
Leu Ser Tyr Ser Ala Gly Ala Leu Ala Ser Cys Met Gly Leu Ile Tyr
                420                 425                 430

Asn Arg Met Gly Ala Val Thr Thr Glu Val Ala Phe Gly Leu Val Cys
            435                 440                 445

Ala Thr Cys Glu Gln Ile Ala Asp Ser Gln His Arg Ser His Arg Gln
        450                 455                 460

Leu Glu His His His His His His
465                 470

<210> SEQ ID NO 2
<211> LENGTH: 473
<212> TYPE: PRT
<213> ORGANISM: Artificial Sequence
<220> FEATURE:
<223> OTHER INFORMATION: SAPNA sequence

<400> SEQUENCE: 2

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Cys Asp Cys Ala Trp His Leu Gly Glu Leu
    130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Glu Ala Gln Lys Gln Lys Leu Leu
```

```
                290                 295                 300
Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
                340                 345                 350

Ser Pro Leu Thr Lys Gly Ile Leu Gly Phe Val Phe Thr Leu Thr Val
                355                 360                 365

Pro Ser Glu Arg Gly Leu Gln Arg Arg Arg Phe Val Gln Asn Ala Leu
370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
                405                 410                 415

Leu Ser Tyr Ser Ala Gly Ala Leu Ala Ser Cys Met Gly Leu Ile Tyr
                420                 425                 430

Asn Arg Met Gly Ala Val Thr Thr Glu Val Ala Phe Gly Leu Val Cys
                435                 440                 445

Ala Thr Cys Glu Gln Ile Ala Asp Ser Gln Glu Asn Leu Tyr Phe Gln
450                 455                 460

Gly Leu Glu His His His His His His
465                 470

<210> SEQ ID NO 3
<211> LENGTH: 480
<212> TYPE: PRT
<213> ORGANISM: Artificial Sequence
<220> FEATURE:
<223> OTHER INFORMATION: SAPNA sequence

<400> SEQUENCE: 3

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
                35                  40                  45

Asp Ala Gly Tyr Arg Val Ile Thr Tyr Asp Arg Arg Gly Phe Gly Gln
                50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
                115                 120                 125

Phe Leu Leu Lys Thr Gly Gly Ser Gly Cys Asp Cys Ala Trp His
                130                 135                 140

Leu Gly Glu Leu Val Trp Cys Thr Cys Gly Ser Gly Gly Gly Asp Asn
145                 150                 155                 160

Pro Asp Gly Ala Ala Pro Gln Glu Phe Asp Gly Ile Val Ala Ala
                165                 170                 175

Val Lys Ala Asp Arg Tyr Ala Phe Tyr Thr Gly Phe Phe Asn Asp Phe
```

```
                   180                 185                 190
Tyr Asn Leu Asp Glu Asn Leu Gly Thr Arg Ile Ser Glu Glu Ala Val
            195                 200                 205

Arg Asn Ser Trp Asn Thr Ala Ala Ser Gly Gly Phe Phe Ala Ala Ala
            210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
            245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
            275                 280                 285

Ala Glu Glu Val Asn Thr Ala Leu Leu Ala Phe Leu Ala Lys Ala Gln
            290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
            325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
            355                 360                 365

Gly Phe Val Phe Thr Leu Thr Val Pro Ser Glu Arg Gly Leu Gln Arg
            370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
            405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
            435                 440                 445

Glu Val Ala Phe Gly Leu Val Cys Ala Thr Cys Glu Gln Ile Ala Asp
            450                 455                 460

Ser Gln His Arg Ser His Arg Gln Leu Glu His His His His His His
465                 470                 475                 480

<210> SEQ ID NO 4
<211> LENGTH: 481
<212> TYPE: PRT
<213> ORGANISM: Artificial Sequence
<220> FEATURE:
<223> OTHER INFORMATION: SAPNA sequence

<400> SEQUENCE: 4

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
            50                  55                  60

Ser Ser Gln Pro Thr Thr Gly Tyr Asp Tyr Asp Thr Phe Ala Ala Asp
```

```
         65                  70                  75                  80
Leu Asn Thr Val Leu Glu Thr Leu Asp Leu Gln Asp Ala Val Leu Val
                     85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
                115                 120                 125

Phe Leu Leu Lys Thr Gly Gly Ser Gly Cys Asp Cys Ala Trp His
130                 135                 140

Leu Gly Glu Leu Val Trp Cys Thr Cys Gly Ser Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
                180                 185                 190

Tyr Asn Leu Asp Glu Asn Leu Gly Thr Arg Ile Ser Glu Glu Ala Val
            195                 200                 205

Arg Asn Ser Trp Asn Thr Ala Ala Ser Gly Gly Phe Phe Ala Ala Ala
210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
                260                 265                 270

Glu Tyr Val Glu Val Glu Gly Ala Pro His Gly Leu Leu Trp Thr His
            275                 280                 285

Ala Glu Glu Val Asn Thr Ala Leu Leu Ala Phe Leu Ala Lys Ala Gln
            290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
                340                 345                 350

Trp Leu Lys Thr Arg Pro Ile Leu Ser Pro Leu Thr Lys Gly Ile Leu
            355                 360                 365

Gly Phe Val Phe Thr Leu Thr Val Pro Ser Glu Arg Gly Leu Gln Arg
370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
            435                 440                 445

Glu Val Ala Phe Gly Leu Val Cys Ala Thr Cys Glu Gln Ile Ala Asp
            450                 455                 460

Ser Gln Glu Asn Leu Tyr Phe Gln Gly Leu Glu His His His His
465                 470                 475                 480

His
```

<210> SEQ ID NO 5
<211> LENGTH: 472
<212> TYPE: PRT
<213> ORGANISM: Artificial Sequence
<220> FEATURE:
<223> OTHER INFORMATION: SAPNA sequence

<400> SEQUENCE: 5

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Cys Asp Cys Ala Trp His Leu Gly Glu Leu
130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Gly Ala Gln Lys Gln Lys Leu Leu
    290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365
```

```
Pro Ser Glu Arg Gly Leu Gln Arg Arg Phe Val Gln Asn Ala Leu
    370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
            405                 410                 415

Leu Ser Tyr Ser Ala Gly Ala Leu Ala Ser Cys Met Gly Leu Ile Tyr
            420                 425                 430

Asn Arg Met Gly Ala Val Thr Thr Glu Val Ala Phe Gly Leu Val Cys
            435                 440                 445

Ala Thr Cys Glu Gln Ile Ala Asp Ser Gln His Arg Ser His Arg Gln
450                 455                 460

Leu Glu His His His His His His
465                 470

<210> SEQ ID NO 6
<211> LENGTH: 473
<212> TYPE: PRT
<213> ORGANISM: Artificial Sequence
<220> FEATURE:
<223> OTHER INFORMATION: SAPNA sequence

<400> SEQUENCE: 6

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Cys Asp Cys Ala Trp His Leu Gly Glu Leu
    130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255
```

Phe His Lys Ala Leu Pro Ser Ala Glu Tyr Val Glu Val Glu Gly Ala
                260                 265                 270

Pro His Gly Leu Leu Trp Thr His Ala Glu Glu Val Asn Thr Ala Leu
            275                 280                 285

Leu Ala Phe Leu Ala Lys Ala Gln Glu Ala Gln Lys Gln Lys Leu Leu
        290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365

Pro Ser Glu Arg Gly Leu Gln Arg Arg Phe Val Gln Asn Ala Leu
370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
                405                 410                 415

Leu Ser Tyr Ser Ala Gly Ala Leu Ala Ser Cys Met Gly Leu Ile Tyr
            420                 425                 430

Asn Arg Met Gly Ala Val Thr Thr Glu Val Ala Phe Gly Leu Val Cys
        435                 440                 445

Ala Thr Cys Glu Gln Ile Ala Asp Ser Gln His Asn Leu Tyr Phe Gln
        450                 455                 460

Gly Leu Glu His His His His His His
465                 470

<210> SEQ ID NO 7
<211> LENGTH: 480
<212> TYPE: PRT
<213> ORGANISM: Artificial Sequence
<220> FEATURE:
<223> OTHER INFORMATION: SAPNA sequence

<400> SEQUENCE: 7

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Ala Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Gly Gly Gly Ser Gly Cys Asp Cys Ala Trp His
        130                 135                 140

```
Leu Gly Glu Leu Val Trp Cys Thr Cys Gly Ser Gly Gly Gly Asp Asn
145                 150                 155                 160

Pro Asp Gly Ala Ala Pro Gln Glu Phe Phe Asp Gly Ile Val Ala Ala
            165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
            195                 200                 205

Arg Asn Ser Trp Asn Thr Ala Ala Ser Gly Gly Phe Phe Ala Ala Ala
        210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
                260                 265                 270

Glu Tyr Val Glu Val Gly Ala Pro His Gly Leu Leu Trp Thr His
            275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
            355                 360                 365

Gly Phe Val Phe Thr Leu Thr Val Pro Ser Glu Arg Gly Leu Gln Arg
        370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
                420                 425                 430

Ala Ser Cys Met Gly Leu Ile Tyr Asn Arg Met Gly Ala Val Thr Thr
            435                 440                 445

Glu Val Ala Phe Gly Leu Val Cys Ala Thr Cys Glu Gln Ile Ala Asp
        450                 455                 460

Ser Gln His Arg Ser His Arg Gln Leu Glu His His His His
465                 470                 475                 480
```

<210> SEQ ID NO 8
<211> LENGTH: 481
<212> TYPE: PRT
<213> ORGANISM: Artificial Sequence
<220> FEATURE:
<223> OTHER INFORMATION: SAPNA sequence

<400> SEQUENCE: 8

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30
```

```
Phe Pro Leu Ser Gly His Ser Trp Glu Arg Gln Ser Ala Leu Leu
             35                  40                  45
Asp Ala Gly Ala Arg Val Ile Thr Tyr Asp Arg Arg Gly Phe Gly Gln
 50                  55                  60
Ser Ser Gln Pro Thr Thr Gly Tyr Asp Tyr Asp Thr Phe Ala Ala Asp
 65                  70                  75                  80
Leu Asn Thr Val Leu Glu Thr Leu Asp Leu Gln Asp Ala Val Leu Val
                 85                  90                  95
Gly Phe Ser Met Gly Thr Gly Glu Val Ala Arg Tyr Val Ser Ser Tyr
                100                 105                 110
Gly Thr Ala Arg Ile Ala Ala Val Ala Phe Leu Ala Ser Leu Glu Pro
             115                 120                 125
Phe Leu Leu Lys Thr Gly Gly Ser Gly Cys Asp Cys Ala Trp His
 130                 135                 140
Leu Gly Glu Leu Val Trp Cys Thr Cys Gly Ser Gly Gly Asp Asn
 145                 150                 155                 160
Pro Asp Gly Ala Ala Pro Gln Glu Phe Phe Asp Gly Ile Val Ala Ala
                 165                 170                 175
Val Lys Ala Asp Arg Tyr Ala Phe Tyr Thr Gly Phe Phe Asn Asp Phe
             180                 185                 190
Tyr Asn Leu Asp Glu Asn Leu Gly Thr Arg Ile Ser Glu Glu Ala Val
         195                 200                 205
Arg Asn Ser Trp Asn Thr Ala Ala Ser Gly Gly Phe Phe Ala Ala Ala
     210                 215                 220
Ala Ala Pro Thr Thr Trp Tyr Thr Asp Phe Arg Ala Asp Ile Pro Arg
225                 230                 235                 240
Ile Asp Val Pro Ala Leu Ile Leu His Gly Thr Gly Asp Arg Thr Leu
                 245                 250                 255
Pro Ile Glu Asn Thr Ala Arg Val Phe His Lys Ala Leu Pro Ser Ala
             260                 265                 270
Glu Tyr Val Glu Val Glu Gly Ala Pro His Gly Leu Leu Trp Thr His
         275                 280                 285
Ala Glu Glu Val Asn Thr Ala Leu Leu Ala Phe Leu Ala Lys Ala Gln
     290                 295                 300
Glu Ala Gln Lys Gln Lys Leu Leu Thr Glu Val Glu Thr Tyr Val Leu
305                 310                 315                 320
Ser Ile Ile Pro Ser Gly Pro Leu Lys Ala Glu Ile Ala Gln Arg Leu
                 325                 330                 335
Glu Asp Val Phe Ala Gly Lys Asn Thr Asp Leu Glu Val Leu Met Glu
             340                 345                 350
Trp Leu Lys Thr Arg Pro Ile Leu Ser Pro Leu Thr Lys Gly Ile Leu
         355                 360                 365
Gly Phe Val Phe Thr Leu Thr Val Pro Ser Glu Arg Gly Leu Gln Arg
     370                 375                 380
Arg Arg Phe Val Gln Asn Ala Leu Asn Gly Asn Gly Asp Pro Asn Asn
385                 390                 395                 400
Met Asp Lys Ala Val Lys Leu Tyr Arg Lys Leu Lys Arg Glu Ile Thr
                 405                 410                 415
Phe His Gly Ala Lys Glu Ile Ser Leu Ser Tyr Ser Ala Gly Ala Leu
             420                 425                 430
Ala Ser Cys Met Gly Leu Ile Tyr Asn Arg Met Gly Ala Val Thr Thr
         435                 440                 445
Glu Val Ala Phe Gly Leu Val Cys Ala Thr Cys Glu Gln Ile Ala Asp
```

```
                450             455             460
Ser Gln Glu Asn Leu Tyr Phe Gln Gly Leu Glu His His His His
465                 470                 475                 480

His

<210> SEQ ID NO 9
<211> LENGTH: 478
<212> TYPE: PRT
<213> ORGANISM: Artificial Sequence
<220> FEATURE:
<223> OTHER INFORMATION: SAPNA sequence

<400> SEQUENCE: 9

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Arg Trp Gly Cys Asp Cys Ala Trp His Leu
130                 135                 140

Gly Glu Leu Val Trp Cys Thr Cys Gly Trp Glu Gly Asp Asn Pro Asp
145                 150                 155                 160

Gly Ala Ala Pro Gln Glu Phe Phe Asp Gly Ile Val Ala Ala Val Lys
                165                 170                 175

Ala Asp Arg Tyr Ala Phe Tyr Thr Gly Phe Phe Asn Asp Phe Tyr Asn
            180                 185                 190

Leu Asp Glu Asn Leu Gly Thr Arg Ile Ser Glu Glu Ala Val Arg Asn
        195                 200                 205

Ser Trp Asn Thr Ala Ala Ser Gly Gly Phe Phe Ala Ala Ala Ala Ala
210                 215                 220

Pro Thr Thr Trp Tyr Thr Asp Phe Arg Ala Asp Ile Pro Arg Ile Asp
225                 230                 235                 240

Val Pro Ala Leu Ile Leu His Gly Thr Gly Asp Arg Thr Leu Pro Ile
                245                 250                 255

Glu Asn Thr Ala Arg Val Phe His Lys Ala Leu Pro Ser Ala Glu Tyr
            260                 265                 270

Val Glu Val Glu Gly Ala Pro His Gly Leu Leu Trp Thr His Ala Glu
        275                 280                 285

Glu Val Asn Thr Ala Leu Leu Ala Phe Leu Ala Lys Ala Gln Glu Ala
290                 295                 300

Gln Lys Gln Lys Leu Leu Thr Glu Val Glu Thr Tyr Val Leu Ser Ile
305                 310                 315                 320

Ile Pro Ser Gly Pro Leu Lys Ala Glu Ile Ala Gln Arg Leu Glu Asp
                325                 330                 335
```

```
Val Phe Ala Gly Lys Asn Thr Asp Leu Glu Val Leu Met Glu Trp Leu
                340                 345                 350

Lys Thr Arg Pro Ile Leu Ser Pro Leu Thr Lys Gly Ile Leu Gly Phe
            355                 360                 365

Val Phe Thr Leu Thr Val Pro Ser Glu Arg Gly Leu Gln Arg Arg Arg
        370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His
465                 470                 475
```

<210> SEQ ID NO 10
<211> LENGTH: 474
<212> TYPE: PRT
<213> ORGANISM: Artificial Sequence
<220> FEATURE:
<223> OTHER INFORMATION: SAPNA sequence

<400> SEQUENCE: 10

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Arg Trp Asp Cys Ala Trp His Leu Gly Glu
    130                 135                 140

Leu Val Trp Cys Thr Trp Glu Gly Asp Asn Pro Asp Gly Ala Ala Pro
145                 150                 155                 160

Gln Glu Phe Phe Asp Gly Ile Val Ala Val Lys Ala Asp Arg Tyr
                165                 170                 175

Ala Phe Tyr Thr Gly Phe Phe Asn Asp Phe Tyr Asn Leu Asp Glu Asn
                180                 185                 190

Leu Gly Thr Arg Ile Ser Glu Glu Ala Val Arg Asn Ser Trp Asn Thr
            195                 200                 205

Ala Ala Ser Gly Gly Phe Phe Ala Ala Ala Ala Pro Thr Thr Trp
        210                 215                 220
```

Tyr Thr Asp Phe Arg Ala Asp Ile Pro Arg Ile Asp Val Pro Ala Leu
225                 230                 235                 240

Ile Leu His Gly Thr Gly Asp Arg Thr Leu Pro Ile Glu Asn Thr Ala
            245                 250                 255

Arg Val Phe His Lys Ala Leu Pro Ser Ala Glu Tyr Val Glu Val Glu
        260                 265                 270

Gly Ala Pro His Gly Leu Leu Trp Thr His Ala Glu Glu Val Asn Thr
    275                 280                 285

Ala Leu Leu Ala Phe Leu Ala Lys Ala Gln Glu Ala Gln Lys Gln Lys
290                 295                 300

Leu Leu Thr Glu Val Glu Thr Tyr Val Leu Ser Ile Ile Pro Ser Gly
305                 310                 315                 320

Pro Leu Lys Ala Glu Ile Ala Gln Arg Leu Glu Asp Val Phe Ala Gly
                325                 330                 335

Lys Asn Thr Asp Leu Glu Val Leu Met Glu Trp Leu Lys Thr Arg Pro
            340                 345                 350

Ile Leu Ser Pro Leu Thr Lys Gly Ile Leu Gly Phe Val Phe Thr Leu
        355                 360                 365

Thr Val Pro Ser Glu Arg Gly Leu Gln Arg Arg Phe Val Gln Asn
370                 375                 380

Ala Leu Asn Gly Asn Gly Asp Pro Asn Asn Met Asp Lys Ala Val Lys
385                 390                 395                 400

Leu Tyr Arg Lys Leu Lys Arg Glu Ile Thr Phe His Gly Ala Lys Glu
                405                 410                 415

Ile Ser Leu Ser Tyr Ser Ala Gly Leu Ala Ser Cys Met Gly Leu
            420                 425                 430

Ile Tyr Asn Arg Met Gly Ala Val Thr Thr Glu Val Ala Phe Gly Leu
        435                 440                 445

Val Cys Ala Thr Cys Glu Gln Ile Ala Asp Ser Gln His Arg Ser His
    450                 455                 460

Arg Gln Leu Glu His His His His His His
465                 470

<210> SEQ ID NO 11
<211> LENGTH: 480
<212> TYPE: PRT
<213> ORGANISM: Artificial Sequence
<220> FEATURE:
<223> OTHER INFORMATION: SAPNA sequence

<400> SEQUENCE: 11

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

```
Gly Thr Ala Arg Ile Ala Ala Val Ala Phe Leu Ala Ser Leu Glu Pro
            115                 120                 125

Phe Leu Leu Lys Thr Gly Gly Gly Arg Trp Asp Cys Ala Trp His
130                 135                 140

Leu Gly Glu Leu Val Trp Cys Thr Trp Glu Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
            195                 200                 205

Arg Asn Ser Trp Asn Thr Ala Ala Ser Gly Gly Phe Phe Ala Ala Ala
            210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
            275                 280                 285

Ala Glu Glu Val Asn Thr Ala Leu Leu Ala Phe Leu Ala Lys Ala Gln
            290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
            355                 360                 365

Gly Phe Val Phe Thr Leu Thr Val Pro Ser Glu Arg Gly Leu Gln Arg
370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
            435                 440                 445

Glu Val Ala Phe Gly Leu Val Cys Ala Thr Cys Glu Gln Ile Ala Asp
450                 455                 460

Ser Gln His Arg Ser His Arg Gln Leu Glu His His His His His His
465                 470                 475                 480

<210> SEQ ID NO 12
<211> LENGTH: 480
<212> TYPE: PRT
<213> ORGANISM: Artificial Sequence
<220> FEATURE:
<223> OTHER INFORMATION: SAPNA sequence

<400> SEQUENCE: 12
```

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65              70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Gly Gly Gly Arg Trp Asp Ala Ala Trp His
        130                 135                 140

Leu Gly Glu Leu Val Trp Ala Thr Trp Glu Gly Gly Gly Gly Asp Asn
145             150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
                180                 185                 190

Tyr Asn Leu Asp Glu Asn Leu Gly Thr Arg Ile Ser Glu Glu Ala Val
            195                 200                 205

Arg Asn Ser Trp Asn Thr Ala Ala Ser Gly Gly Phe Phe Ala Ala Ala
        210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415
```

```
Phe His Gly Ala Lys Glu Ile Ser Leu Ser Tyr Ser Ala Gly Ala Leu
                420                 425                 430

Ala Ser Cys Met Gly Leu Ile Tyr Asn Arg Met Gly Ala Val Thr Thr
            435                 440                 445

Glu Val Ala Phe Gly Leu Val Cys Ala Thr Cys Glu Gln Ile Ala Asp
        450                 455                 460

Ser Gln His Arg Ser His Arg Gln Leu Glu His His His His His His
465                 470                 475                 480

<210> SEQ ID NO 13
<211> LENGTH: 480
<212> TYPE: PRT
<213> ORGANISM: Artificial Sequence
<220> FEATURE:
<223> OTHER INFORMATION: SAPNA sequence

<400> SEQUENCE: 13

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Ser Gly Ala Asp Cys Ala Trp His
    130                 135                 140

Leu Gly Glu Leu Val Trp Cys Thr Ala Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300
```

```
Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
            325                 330                 335

Glu Asp Val Phe Ala Gly Lys Asn Thr Asp Leu Glu Val Leu Met Glu
                340                 345                 350

Trp Leu Lys Thr Arg Pro Ile Leu Ser Pro Leu Thr Lys Gly Ile Leu
            355                 360                 365

Gly Phe Val Phe Thr Leu Thr Val Pro Ser Glu Arg Gly Leu Gln Arg
        370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
            435                 440                 445

Glu Val Ala Phe Gly Leu Val Cys Ala Thr Cys Glu Gln Ile Ala Asp
450                 455                 460

Ser Gln His Arg Ser His Arg Gln Leu Glu His His His His His His
465                 470                 475                 480

<210> SEQ ID NO 14
<211> LENGTH: 480
<212> TYPE: PRT
<213> ORGANISM: Artificial Sequence
<220> FEATURE:
<223> OTHER INFORMATION: SAPNA sequence

<400> SEQUENCE: 14

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Gly Gly Gly Ser Gly Ala Asp Ala Ala Trp His
        130                 135                 140

Leu Gly Glu Leu Val Trp Ala Thr Ala Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
                180                 185                 190
```

```
Tyr Asn Leu Asp Glu Asn Leu Gly Thr Arg Ile Ser Glu Glu Ala Val
            195                 200                 205

Arg Asn Ser Trp Asn Thr Ala Ala Ser Gly Gly Phe Ala Ala Ala
210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480

<210> SEQ ID NO 15
<211> LENGTH: 481
<212> TYPE: PRT
<213> ORGANISM: Artificial Sequence
<220> FEATURE:
<223> OTHER INFORMATION: SAPNA sequence

<400> SEQUENCE: 15

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80
```

```
Leu Asn Thr Val Leu Glu Thr Leu Asp Leu Gln Asp Ala Val Leu Val
                 85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Gly Gly Ser Gly Cys Asp Cys Ala
                245                 250                 255

Trp His Leu Gly Glu Leu Val Trp Cys Thr Cys Gly Ser Gly Gly
            260                 265                 270

Ala Glu Tyr Val Glu Val Glu Gly Ala Pro His Gly Leu Leu Trp Thr
        275                 280                 285

His Ala Glu Glu Val Asn Thr Ala Leu Leu Ala Phe Leu Ala Lys Ala
    290                 295                 300

Gln Glu Ala Gln Lys Gln Lys Leu Leu Thr Glu Val Glu Thr Tyr Val
305                 310                 315                 320

Leu Ser Ile Ile Pro Ser Gly Pro Leu Lys Ala Glu Ile Ala Gln Arg
                325                 330                 335

Leu Glu Asp Val Phe Ala Gly Lys Asn Thr Asp Leu Glu Val Leu Met
            340                 345                 350

Glu Trp Leu Lys Thr Arg Pro Ile Leu Ser Pro Leu Thr Lys Gly Ile
        355                 360                 365

Leu Gly Phe Val Phe Thr Leu Thr Val Pro Ser Glu Arg Gly Leu Gln
    370                 375                 380

Arg Arg Arg Phe Val Gln Asn Ala Leu Asn Gly Asn Gly Asp Pro Asn
385                 390                 395                 400

Asn Met Asp Lys Ala Val Lys Leu Tyr Arg Lys Leu Lys Arg Glu Ile
                405                 410                 415

Thr Phe His Gly Ala Lys Glu Ile Ser Leu Ser Tyr Ser Ala Gly Ala
            420                 425                 430

Leu Ala Ser Cys Met Gly Leu Ile Tyr Asn Arg Met Gly Ala Val Thr
        435                 440                 445

Thr Glu Val Ala Phe Gly Leu Val Cys Ala Thr Cys Glu Gln Ile Ala
    450                 455                 460

Asp Ser Gln His Arg Ser His Arg Gln Leu Glu His His His His
465                 470                 475                 480

His

<210> SEQ ID NO 16
```

<211> LENGTH: 480
<212> TYPE: PRT
<213> ORGANISM: Artificial Sequence
<220> FEATURE:
<223> OTHER INFORMATION: SAPNA sequence

<400> SEQUENCE: 16

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Gly Gly Ser Gly Cys Asp
    210                 215                 220

Cys Ala Trp His Leu Gly Glu Leu Val Trp Cys Thr Cys Gly Ser Gly
225                 230                 235                 240

Gly Gly Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380
```

```
Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480
```

<210> SEQ ID NO 17
<211> LENGTH: 475
<212> TYPE: PRT
<213> ORGANISM: Artificial Sequence
<220> FEATURE:
<223> OTHER INFORMATION: SAPNA sequence

<400> SEQUENCE: 17

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Gly Gly Gly Ser Gly
                165                 170                 175

Cys Asp Cys Ala Trp His Leu Gly Glu Leu Val Trp Cys Thr Cys Gly
            180                 185                 190

Ser Gly Gly Gly Arg Ile Ser Glu Glu Ala Val Arg Asn Ser Trp Asn
        195                 200                 205

Thr Ala Ala Ser Gly Gly Phe Phe Ala Ala Ala Ala Pro Thr Thr
    210                 215                 220

Trp Tyr Thr Asp Phe Arg Ala Asp Ile Pro Arg Ile Asp Val Pro Ala
225                 230                 235                 240

Leu Ile Leu His Gly Thr Gly Asp Arg Thr Leu Pro Ile Glu Asn Thr
                245                 250                 255

Ala Arg Val Phe His Lys Ala Leu Pro Ser Ala Glu Tyr Val Glu Val
            260                 265                 270
```

```
Glu Gly Ala Pro His Gly Leu Leu Trp Thr His Ala Glu Glu Val Asn
            275                 280                 285

Thr Ala Leu Leu Ala Phe Leu Ala Lys Ala Gln Glu Ala Gln Lys Gln
        290                 295                 300

Lys Leu Leu Thr Glu Val Glu Thr Tyr Val Leu Ser Ile Ile Pro Ser
305                 310                 315                 320

Gly Pro Leu Lys Ala Glu Ile Ala Gln Arg Leu Glu Asp Val Phe Ala
                325                 330                 335

Gly Lys Asn Thr Asp Leu Glu Val Leu Met Glu Trp Leu Lys Thr Arg
            340                 345                 350

Pro Ile Leu Ser Pro Leu Thr Lys Gly Ile Leu Gly Phe Val Phe Thr
        355                 360                 365

Leu Thr Val Pro Ser Glu Arg Gly Leu Gln Arg Arg Phe Val Gln
    370                 375                 380

Asn Ala Leu Asn Gly Asn Gly Asp Pro Asn Asn Met Asp Lys Ala Val
385                 390                 395                 400

Lys Leu Tyr Arg Lys Leu Lys Arg Glu Ile Thr Phe His Gly Ala Lys
                405                 410                 415

Glu Ile Ser Leu Ser Tyr Ser Ala Gly Ala Leu Ala Ser Cys Met Gly
            420                 425                 430

Leu Ile Tyr Asn Arg Met Gly Ala Val Thr Thr Glu Val Ala Phe Gly
        435                 440                 445

Leu Val Cys Ala Thr Cys Glu Gln Ile Ala Asp Ser Gln His Arg Ser
    450                 455                 460

His Arg Gln Leu Glu His His His His His
465                 470                 475

<210> SEQ ID NO 18
<211> LENGTH: 478
<212> TYPE: PRT
<213> ORGANISM: Artificial Sequence
<220> FEATURE:
<223> OTHER INFORMATION: SAPNA sequence

<400> SEQUENCE: 18

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160
```

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Gly Ser Gly Cys Asp Cys Ala Trp His Leu Gly
225                 230                 235                 240

Glu Leu Val Trp Cys Thr Cys Gly Ser Gly Gly Thr Leu Pro Ile
                245                 250                 255

Glu Asn Thr Ala Arg Val Phe His Lys Ala Leu Pro Ser Ala Glu Tyr
            260                 265                 270

Val Glu Val Glu Gly Ala Pro His Gly Leu Leu Trp Thr His Ala Glu
        275                 280                 285

Glu Val Asn Thr Ala Leu Leu Ala Phe Leu Ala Lys Ala Gln Glu Ala
        290                 295                 300

Gln Lys Gln Lys Leu Leu Thr Glu Val Glu Thr Tyr Val Leu Ser Ile
305                 310                 315                 320

Ile Pro Ser Gly Pro Leu Lys Ala Glu Ile Ala Gln Arg Leu Glu Asp
                325                 330                 335

Val Phe Ala Gly Lys Asn Thr Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His
465                 470                 475

<210> SEQ ID NO 19
<211> LENGTH: 478
<212> TYPE: PRT
<213> ORGANISM: Artificial Sequence
<220> FEATURE:
<223> OTHER INFORMATION: SAPNA sequence

<400> SEQUENCE: 19

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

```
Asp Ala Gly Tyr Arg Val Ile Thr Tyr Asp Arg Arg Gly Phe Gly Gln
            50                  55                  60

Ser Ser Gln Pro Thr Thr Gly Tyr Asp Tyr Asp Thr Phe Ala Ala Asp
 65                  70                  75                  80

Leu Asn Thr Val Leu Glu Thr Leu Asp Leu Gln Asp Ala Val Leu Val
                    85                  90                  95

Gly Phe Ser Met Gly Thr Gly Glu Val Ala Arg Tyr Val Ser Ser Tyr
                100                 105                 110

Gly Gly Gly Ser Gly Cys Asp Cys Ala Trp His Leu Gly Glu Leu Val
            115                 120                 125

Trp Cys Thr Cys Gly Ser Gly Gly Arg Ile Ala Ala Val Ala Phe
                    135                 140

Leu Ala Ser Leu Glu Pro Phe Leu Leu Lys Thr Asp Asp Asn Pro Asp
145                 150                 155                 160

Gly Ala Ala Pro Gln Glu Phe Phe Asp Gly Ile Val Ala Ala Val Lys
                    165                 170                 175

Ala Asp Arg Tyr Ala Phe Tyr Thr Gly Phe Phe Asn Asp Phe Tyr Asn
                180                 185                 190

Leu Asp Glu Asn Leu Gly Thr Arg Ile Ser Glu Glu Ala Val Arg Asn
                195                 200                 205

Ser Trp Asn Thr Ala Ala Ser Gly Gly Phe Phe Ala Ala Ala Ala Ala
210                 215                 220

Pro Thr Thr Trp Tyr Thr Asp Phe Arg Ala Asp Ile Pro Arg Ile Asp
225                 230                 235                 240

Val Pro Ala Leu Ile Leu His Gly Thr Gly Asp Arg Thr Leu Pro Ile
                    245                 250                 255

Glu Asn Thr Ala Arg Val Phe His Lys Ala Leu Pro Ser Ala Glu Tyr
                260                 265                 270

Val Glu Val Glu Gly Ala Pro His Gly Leu Leu Trp Thr His Ala Glu
            275                 280                 285

Glu Val Asn Thr Ala Leu Leu Ala Phe Leu Ala Lys Ala Gln Glu Ala
            290                 295                 300

Gln Lys Gln Lys Leu Leu Thr Glu Val Glu Thr Tyr Val Leu Ser Ile
305                 310                 315                 320

Ile Pro Ser Gly Pro Leu Lys Ala Glu Ile Ala Gln Arg Leu Glu Asp
                325                 330                 335

Val Phe Ala Gly Lys Asn Thr Asp Leu Glu Val Leu Met Glu Trp Leu
                340                 345                 350

Lys Thr Arg Pro Ile Leu Ser Pro Leu Thr Lys Gly Ile Leu Gly Phe
                355                 360                 365

Val Phe Thr Leu Thr Val Pro Ser Glu Arg Gly Leu Gln Arg Arg
            370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                    405                 410                 415

Gly Ala Lys Glu Ile Ser Leu Ser Tyr Ser Ala Gly Ala Leu Ala Ser
                420                 425                 430

Cys Met Gly Leu Ile Tyr Asn Arg Met Gly Ala Val Thr Thr Glu Val
            435                 440                 445

Ala Phe Gly Leu Val Cys Ala Thr Cys Glu Gln Ile Ala Asp Ser Gln
450                 455                 460
```

His Arg Ser His Arg Gln Leu Glu His His His His His His
465                 470                 475

<210> SEQ ID NO 20
<211> LENGTH: 478
<212> TYPE: PRT
<213> ORGANISM: Artificial Sequence
<220> FEATURE:
<223> OTHER INFORMATION: SAPNA sequence

<400> SEQUENCE: 20

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Gly Gly
305                 310                 315                 320

Gly Ser Gly Cys Asp Cys Ala Trp His Leu Gly Glu Leu Val Trp Cys
                325                 330                 335

Thr Cys Gly Ser Gly Gly Asp Leu Glu Val Leu Met Glu Trp Leu
            340                 345                 350

```
Lys Thr Arg Pro Ile Leu Ser Pro Leu Thr Lys Gly Ile Leu Gly Phe
            355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475
```

<210> SEQ ID NO 21
<211> LENGTH: 475
<212> TYPE: PRT
<213> ORGANISM: Artificial Sequence
<220> FEATURE:
<223> OTHER INFORMATION: SAPNA sequence

<400> SEQUENCE: 21

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240
```

```
Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475

<210> SEQ ID NO 22
<211> LENGTH: 478
<212> TYPE: PRT
<213> ORGANISM: Artificial Sequence
<220> FEATURE:
<223> OTHER INFORMATION: SAPNA sequence

<400> SEQUENCE: 22

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
    115                 120                 125
```

```
Phe Leu Leu Lys Thr Asp Asp Asn Pro Asp Gly Ala Ala Pro Gln Glu
            130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
                260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Gly Gly
305                 310                 315                 320

Arg Trp Gly Cys Asp Cys Ala Trp His Leu Gly Glu Leu Val Trp Cys
                325                 330                 335

Thr Cys Gly Trp Glu Gly Gly Asp Leu Glu Val Leu Met Glu Trp Leu
                340                 345                 350

Lys Thr Arg Pro Ile Leu Ser Pro Leu Thr Lys Gly Ile Leu Gly Phe
            355                 360                 365

Val Phe Thr Leu Thr Val Pro Ser Glu Arg Gly Leu Gln Arg Arg
370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
            435                 440                 445

Ala Phe Gly Leu Val Cys Ala Thr Cys Glu Gln Ile Ala Asp Ser Gln
450                 455                 460

His Arg Ser His Arg Gln Leu Glu His His His His His
465                 470                 475

<210> SEQ ID NO 23
<211> LENGTH: 478
<212> TYPE: PRT
<213> ORGANISM: Artificial Sequence
<220> FEATURE:
<223> OTHER INFORMATION: SAPNA sequence

<400> SEQUENCE: 23

Met Pro Phe Ile Thr Val Gly Gln Glu Asn Ser Thr Ser Ile Asp Leu
1               5                   10                  15
```

-continued

```
Tyr Tyr Glu Asp His Gly Thr Gly Thr Pro Val Val Leu Ile His Gly
             20                  25                  30

Phe Pro Leu Ser Gly His Ser Trp Glu Arg Gln Ser Ala Ala Leu Leu
             35                  40                  45

Asp Ala Gly Tyr Arg Val Ile Thr Tyr Asp Arg Arg Gly Phe Gly Gln
 50                  55                  60

Ser Ser Gln Pro Thr Thr Gly Tyr Asp Tyr Asp Thr Phe Ala Ala Asp
 65                  70                  75                  80

Leu Asn Thr Val Leu Glu Thr Leu Asp Leu Gln Asp Ala Val Leu Val
                 85                  90                  95

Gly Phe Ser Met Gly Thr Gly Glu Val Ala Arg Tyr Val Ser Ser Tyr
             100                 105                 110

Gly Thr Ala Arg Ile Ala Ala Val Ala Phe Leu Ala Ser Leu Glu Pro
             115                 120                 125

Phe Leu Leu Lys Thr Asp Asp Asn Pro Asp Gly Ala Ala Pro Gln Glu
             130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                 165                 170                 175

Thr Arg Ile Ser Glu Glu Ala Val Arg Asn Ser Trp Asn Thr Ala Ala
             180                 185                 190

Ser Gly Gly Phe Phe Ala Ala Ala Ala Pro Thr Thr Trp Tyr Thr
             195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                 245                 250                 255

Pro His Gly Leu Leu Trp Thr His Ala Glu Val Asn Thr Ala Leu
             260                 265                 270

Leu Ala Phe Leu Ala Lys Ala Gln Glu Ala Gln Lys Gln Lys Leu Leu
             275                 280                 285

Thr Glu Val Glu Thr Tyr Val Leu Ser Ile Ile Pro Ser Gly Pro Leu
 290                 295                 300

Lys Ala Glu Ile Ala Gln Arg Leu Glu Asp Val Phe Ala Gly Arg Trp
305                 310                 315                 320

Gly Ser Gly Cys Asp Cys Ala Trp His Leu Gly Glu Leu Val Trp Cys
                 325                 330                 335

Thr Cys Gly Ser Gly Trp Glu Asp Leu Glu Val Leu Met Glu Trp Leu
             340                 345                 350

Lys Thr Arg Pro Ile Leu Ser Pro Leu Thr Lys Gly Ile Leu Gly Phe
             355                 360                 365

Val Phe Thr Leu Thr Val Pro Ser Glu Arg Gly Leu Gln Arg Arg Arg
 370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                 405                 410                 415

Gly Ala Lys Glu Ile Ser Leu Ser Tyr Ser Ala Gly Ala Leu Ala Ser
             420                 425                 430

Cys Met Gly Leu Ile Tyr Asn Arg Met Gly Ala Val Thr Thr Glu Val
```

```
            435                 440                 445
Ala Phe Gly Leu Val Cys Ala Thr Cys Glu Gln Ile Ala Asp Ser Gln
        450                 455                 460

His Arg Ser His Arg Gln Leu Glu His His His His His His
465                 470                 475
```

<210> SEQ ID NO 24
<211> LENGTH: 474
<212> TYPE: PRT
<213> ORGANISM: Artificial Sequence
<220> FEATURE:
<223> OTHER INFORMATION: SAPNA sequence

<400> SEQUENCE: 24

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Glu
130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
            290                 295                 300

Lys Ala Glu Ile Ala Gln Arg Leu Glu Asp Val Phe Ala Gly Gly Gly
305                 310                 315                 320

Gly Cys Asp Cys Ala Trp His Leu Gly Glu Leu Val Trp Cys Thr Cys
```

```
                  325                 330                 335
Gly Gly Gly Asp Leu Glu Val Leu Met Glu Trp Leu Lys Thr Arg Pro
            340                 345                 350
Ile Leu Ser Pro Leu Thr Lys Gly Ile Leu Gly Phe Val Phe Thr Leu
            355                 360                 365
Thr Val Pro Ser Glu Arg Gly Leu Gln Arg Arg Phe Val Gln Asn
        370                 375                 380
Ala Leu Asn Gly Asn Gly Asp Pro Asn Met Asp Lys Ala Val Lys
385                 390                 395                 400
Leu Tyr Arg Lys Leu Lys Arg Glu Ile Thr Phe His Gly Ala Lys Glu
                405                 410                 415
Ile Ser Leu Ser Tyr Ser Ala Gly Ala Leu Ala Ser Cys Met Gly Leu
            420                 425                 430
Ile Tyr Asn Arg Met Gly Ala Val Thr Thr Glu Val Ala Phe Gly Leu
            435                 440                 445
Val Cys Ala Thr Cys Glu Gln Ile Ala Asp Ser Gln His Arg Ser His
450                 455                 460
Arg Gln Leu Glu His His His His His His
465                 470

<210> SEQ ID NO 25
<211> LENGTH: 470
<212> TYPE: PRT
<213> ORGANISM: Artificial Sequence
<220> FEATURE:
<223> OTHER INFORMATION: SAPNA sequence

<400> SEQUENCE: 25

Met Pro Phe Ile Thr Val Gly Gln Glu Asn Ser Thr Ser Ile Asp Leu
1               5                   10                  15
Tyr Tyr Glu Asp His Gly Thr Gly Thr Pro Val Val Leu Ile His Gly
                20                  25                  30
Phe Pro Leu Ser Gly His Ser Trp Glu Arg Gln Ser Ala Ala Leu Leu
            35                  40                  45
Asp Ala Gly Tyr Arg Val Ile Thr Tyr Asp Arg Arg Gly Phe Gly Gln
        50                  55                  60
Ser Ser Gln Pro Thr Thr Gly Tyr Asp Tyr Asp Thr Phe Ala Ala Asp
65                  70                  75                  80
Leu Asn Thr Val Leu Glu Thr Leu Asp Leu Gln Asp Ala Val Leu Val
                85                  90                  95
Gly Phe Ser Met Gly Thr Gly Glu Val Ala Arg Tyr Val Ser Ser Tyr
                100                 105                 110
Gly Thr Ala Arg Ile Ala Ala Val Ala Phe Leu Ala Ser Leu Glu Pro
            115                 120                 125
Phe Leu Leu Lys Thr Asp Asp Asn Pro Asp Gly Ala Ala Pro Gln Glu
        130                 135                 140
Phe Phe Asp Gly Ile Val Ala Ala Val Lys Ala Asp Arg Tyr Ala Phe
145                 150                 155                 160
Tyr Thr Gly Phe Phe Asn Asp Phe Tyr Asn Leu Asp Glu Asn Leu Gly
                165                 170                 175
Thr Arg Ile Ser Glu Glu Ala Val Arg Asn Ser Trp Asn Thr Ala Ala
                180                 185                 190
Ser Gly Gly Phe Phe Ala Ala Ala Ala Pro Thr Thr Trp Tyr Thr
            195                 200                 205
Asp Phe Arg Ala Asp Ile Pro Arg Ile Asp Val Pro Ala Leu Ile Leu
```

```
            210                 215                 220
His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
                260                 265                 270

Leu Ala Phe Leu Ala Lys Ala Gln Glu Ala Gln Lys Gln Lys Leu Leu
                275                 280                 285

Thr Glu Val Glu Thr Tyr Val Leu Ser Ile Ile Pro Ser Gly Pro Leu
                290                 295                 300

Lys Ala Glu Ile Ala Gln Arg Leu Glu Asp Val Phe Ala Gly Gly Cys
305                 310                 315                 320

Asp Cys Ala Trp His Leu Gly Glu Leu Val Trp Cys Thr Cys Gly Asp
                325                 330                 335

Leu Glu Val Leu Met Glu Trp Leu Lys Thr Arg Pro Ile Leu Ser Pro
                340                 345                 350

Leu Thr Lys Gly Ile Leu Gly Phe Val Phe Thr Leu Thr Val Pro Ser
                355                 360                 365

Glu Arg Gly Leu Gln Arg Arg Phe Val Gln Asn Ala Leu Asn Gly
                370                 375                 380

Asn Gly Asp Pro Asn Asn Met Asp Lys Ala Val Lys Leu Tyr Arg Lys
385                 390                 395                 400

Leu Lys Arg Glu Ile Thr Phe His Gly Ala Lys Glu Ile Ser Leu Ser
                405                 410                 415

Tyr Ser Ala Gly Ala Leu Ala Ser Cys Met Gly Leu Ile Tyr Asn Arg
                420                 425                 430

Met Gly Ala Val Thr Thr Glu Val Ala Phe Gly Leu Val Cys Ala Thr
                435                 440                 445

Cys Glu Gln Ile Ala Asp Ser Gln His Arg Ser His Arg Gln Leu Glu
                450                 455                 460

His His His His His His
465                 470

<210> SEQ ID NO 26
<211> LENGTH: 475
<212> TYPE: PRT
<213> ORGANISM: Artificial Sequence
<220> FEATURE:
<223> OTHER INFORMATION: SAPNA sequence

<400> SEQUENCE: 26

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
                35                  40                  45

Asp Ala Gly Tyr Arg Val Ile Thr Tyr Asp Arg Arg Gly Phe Gly Gln
                50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
```

```
                100             105             110
Gly Thr Arg Ile Ala Ala Val Ala Phe Leu Ala Ser Leu Glu Pro
            115                 120             125
Phe Leu Leu Lys Thr Asp Asp Asn Pro Asp Gly Ala Ala Pro Gln Lys
130             135                 140
Phe Phe Asp Gly Ile Val Ala Ala Val Lys Ala Asp Arg Tyr Ala Phe
145                 150             155                 160
Tyr Thr Gly Phe Phe Asn Asp Phe Tyr Asn Leu Asp Glu Asn Leu Gly
                165             170             175
Thr Arg Ile Ser Glu Glu Ala Val Arg Asn Ser Trp Asn Thr Ala Ala
            180             185             190
Ser Gly Gly Phe Phe Ala Ala Ala Ala Pro Thr Thr Trp Tyr Thr
            195             200             205
Asp Phe Arg Ala Asp Ile Pro Arg Ile Asp Val Pro Ala Leu Ile Leu
210             215             220
His Gly Thr Gly Asp Arg Thr Leu Pro Ile Glu Asn Thr Ala Arg Val
225             230             235             240
Phe His Lys Ala Leu Pro Ser Ala Glu Tyr Val Glu Val Glu Gly Ala
                245             250             255
Pro His Gly Leu Leu Trp Thr His Ala Glu Val Asn Thr Ala Leu
                260             265             270
Leu Ala Phe Leu Ala Lys Ala Gln Glu Ala Gln Lys Gln Lys Leu Leu
            275             280             285
Thr Glu Val Glu Thr Tyr Val Leu Ser Ile Ile Pro Ser Gly Pro Leu
    290             295             300
Lys Ala Glu Ile Ala Gln Arg Leu Glu Asp Val Phe Ala Gly Lys Asn
305             310             315             320
Thr Asp Leu Glu Val Leu Met Glu Trp Leu Lys Thr Arg Pro Ile Leu
                325             330             335
Ser Pro Leu Thr Lys Gly Ile Leu Gly Phe Val Phe Thr Leu Thr Val
            340             345             350
Pro Ser Glu Arg Gly Leu Gln Arg Arg Phe Val Gln Asn Ala Leu
            355             360             365
Asn Gly Asn Gly Asp Pro Asn Asn Met Asp Lys Ala Val Lys Leu Tyr
    370             375             380
Arg Lys Leu Lys Arg Glu Ile Thr Phe His Gly Ala Lys Glu Ile Ser
385             390             395             400
Leu Ser Tyr Ser Ala Gly Ala Leu Ala Ser Cys Met Gly Leu Ile Tyr
                405             410             415
Asn Arg Met Gly Ala Val Thr Thr Glu Val Ala Phe Gly Leu Val Cys
            420             425             430
Ala Thr Cys Glu Gln Ile Ala Asp Ser Gln Gly Gly Ser Gly Cys
            435             440             445
Asp Cys Ala Trp His Leu Gly Glu Leu Val Trp Cys Thr Cys Gly Ser
    450             455             460
Gly Gly Gly Leu Glu His His His His
465             470             475

<210> SEQ ID NO 27
<211> LENGTH: 475
<212> TYPE: PRT
<213> ORGANISM: Artificial Sequence
<220> FEATURE:
<223> OTHER INFORMATION: SAPNA sequence
```

<400> SEQUENCE: 27

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415
```

```
Asn Arg Met Gly Ala Val Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
450                 455                 460

Gly Gly Gly Leu Glu His His His His His
465                 470                 475

<210> SEQ ID NO 28
<211> LENGTH: 475
<212> TYPE: PRT
<213> ORGANISM: Artificial Sequence
<220> FEATURE:
<223> OTHER INFORMATION: SAPNA sequence

<400> SEQUENCE: 28

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
            85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
            165                 170                 175

Thr Arg Ile Ser Glu Glu Ala Val Arg Asn Ser Trp Asn Thr Ala Ala
        180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Lys Asn Thr Ala Arg Val
225                 230                 235                 240

Phe His Lys Ala Leu Pro Ser Ala Glu Tyr Val Glu Val Glu Gly Ala
            245                 250                 255

Pro His Gly Leu Leu Trp Thr His Ala Glu Glu Val Asn Thr Ala Leu
        260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
        290                 295                 300
```

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
            325                 330                 335

Ser Pro Leu Thr Lys Gly Ile Leu Gly Phe Val Phe Thr Leu Thr Val
        340                 345                 350

Pro Ser Glu Arg Gly Leu Gln Arg Arg Phe Val Gln Asn Ala Leu
    355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475

<210> SEQ ID NO 29
<211> LENGTH: 475
<212> TYPE: PRT
<213> ORGANISM: Artificial Sequence
<220> FEATURE:
<223> OTHER INFORMATION: SAPNA sequence

<400> SEQUENCE: 29

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
            85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Lys
130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
            165                 170                 175

Thr Arg Ile Ser Glu Glu Ala Val Arg Asn Ser Trp Asn Thr Ala Ala
        180                 185                 190

```
Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
            210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Gly Ala
            245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
        290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
            325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
        450                 455                 460

Gly Gly Gly Leu Glu His His His His His His
465                 470                 475

<210> SEQ ID NO 30
<211> LENGTH: 475
<212> TYPE: PRT
<213> ORGANISM: Artificial Sequence
<220> FEATURE:
<223> OTHER INFORMATION: SAPNA sequence

<400> SEQUENCE: 30

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80
```

```
Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Glu
            130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
            210                 215                 220

His Gly Thr Gly Asp Arg Thr Leu Pro Ile Lys Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
            355                 360                 365

Asn Gly Asn Gly Asp Pro Asn Asn Met Asp Lys Ala Val Lys Leu Tyr
370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
450                 455                 460

Gly Gly Gly Leu Glu His His His His
465                 470                 475

<210> SEQ ID NO 31
<211> LENGTH: 475
```

<212> TYPE: PRT
<213> ORGANISM: Artificial Sequence
<220> FEATURE:
<223> OTHER INFORMATION: SAPNA sequence

<400> SEQUENCE: 31

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
                35                  40                  45

Asp Ala Gly Tyr Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Lys
130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Lys Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
                355                 360                 365

Asn Gly Asn Gly Asp Pro Asn Asn Met Asp Lys Ala Val Lys Leu Tyr
370                 375                 380
```

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
            450                 455                 460

Gly Gly Gly Leu Glu His His His His His His
465                 470                 475

<210> SEQ ID NO 32
<211> LENGTH: 475
<212> TYPE: PRT
<213> ORGANISM: Artificial Sequence
<220> FEATURE:
<223> OTHER INFORMATION: SAPNA sequence

<400> SEQUENCE: 32

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
            85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Lys
130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
            165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Lys Asn Thr Ala Arg Val
225                 230                 235                 240

Phe His Lys Ala Leu Pro Ser Ala Glu Tyr Val Glu Val Glu Gly Ala
            245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
            325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
            355                 360                 365

Asn Gly Asn Gly Asp Pro Asn Asn Met Asp Lys Ala Val Lys Leu Tyr
370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
            450                 455                 460

Gly Gly Gly Leu Glu His His His His His
465                 470                 475

<210> SEQ ID NO 33
<211> LENGTH: 475
<212> TYPE: PRT
<213> ORGANISM: Artificial Sequence
<220> FEATURE:
<223> OTHER INFORMATION: SAPNA sequence

<400> SEQUENCE: 33

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
            35                  40                  45

Asp Ala Gly Ala Arg Val Ile Thr Tyr Asp Arg Arg Gly Phe Gly Gln
50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
            85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Glu
130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
            210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Gly Ala
                245                 250                 255

Pro His Gly Leu Leu Trp Thr His Ala Glu Glu Val Asn Thr Ala Leu
                260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
            290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
                340                 345                 350

Pro Ser Glu Arg Gly Leu Gln Arg Arg Phe Val Gln Asn Ala Leu
            355                 360                 365

Asn Gly Asn Gly Asp Pro Asn Asn Met Asp Lys Ala Val Lys Leu Tyr
370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Cys
            435                 440                 445

Asp Cys Ala Trp His Leu Gly Glu Leu Val Trp Cys Thr Cys Gly Ser
            450                 455                 460

Gly Gly Gly Leu Glu His His His His His
465                 470                 475

<210> SEQ ID NO 34
<211> LENGTH: 478
<212> TYPE: PRT
<213> ORGANISM: Artificial Sequence
<220> FEATURE:
<223> OTHER INFORMATION: SAPNA sequence

<400> SEQUENCE: 34

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
            35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
 65                  70                  75                  80

Leu Asn Thr Val Leu Glu Thr Leu Asp Leu Gln Asp Ala Val Leu Val
                 85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
             115                 120                 125

Phe Leu Leu Lys Thr Asp Asp Asn Pro Asp Gly Ala Ala Pro Gln Glu
130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
             180                 185                 190

Ser Gly Gly Phe Phe Ala Ala Ala Ala Pro Thr Thr Trp Tyr Thr
         195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
             260                 265                 270

Leu Ala Phe Leu Ala Lys Ala Gln Glu Ala Gln Lys Gln Lys Leu Leu
         275                 280                 285

Thr Glu Val Glu Thr Tyr Val Leu Ser Ile Ile Pro Ser Gly Pro Leu
     290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
             340                 345                 350

Pro Ser Glu Arg Gly Leu Gln Arg Arg Arg Phe Val Gln Asn Ala Leu
         355                 360                 365

Asn Gly Asn Gly Asp Pro Asn Asn Met Asp Lys Ala Val Lys Leu Tyr
     370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
             420                 425                 430

Ala Thr Cys Glu Gln Ile Ala Asp Ser Gln Gly Gly Ser Gly Gly
         435                 440                 445

Gly Gly Cys Asp Cys Ala Trp His Leu Gly Glu Leu Val Trp Cys Thr
450                 455                 460

Cys Gly Ser Gly Gly Gly Leu Glu His His His His His His

<210> SEQ ID NO 35
<211> LENGTH: 480
<212> TYPE: PRT
<213> ORGANISM: Artificial Sequence
<220> FEATURE:
<223> OTHER INFORMATION: SAPNA sequence

<400> SEQUENCE: 35

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
```

```
                    355                 360                 365
Asn Gly Asn Gly Asp Pro Asn Asn Met Asp Lys Ala Val Lys Leu Tyr
            370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Gly
                435                 440                 445

Gly Ser Gly Gly Cys Asp Cys Ala Trp His Leu Gly Glu Leu Val Trp
            450                 455                 460

Cys Thr Cys Gly Ser Gly Gly Leu Glu His His His His His His
465                 470                 475                 480
```

<210> SEQ ID NO 36
<211> LENGTH: 535
<212> TYPE: PRT
<213> ORGANISM: Artificial Sequence
<220> FEATURE:
<223> OTHER INFORMATION: SAPNA sequence

<400> SEQUENCE: 36

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
```

```
                    245                 250                 255
Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Ser Gly Gly
        435                 440                 445

Gly Ser Gly Gly Gly Ser Gly Gly Gly Ser Gly Gly Gly Ser Gly Gly
    450                 455                 460

Gly Ser Gly Gly Gly Ser Gly Gly Gly Ser Gly Gly Gly Ser Gly Gly
465                 470                 475                 480

Gly Ser Gly Gly Gly Ser Gly Gly Gly Ser Gly Gly Gly Ser Gly Gly
                485                 490                 495

Gly Ser Gly Gly Gly Ser Gly Gly Gly Cys Asp Cys Ala Trp
            500                 505                 510

His Leu Gly Glu Leu Val Trp Cys Thr Cys Gly Ser Gly Gly Leu
        515                 520                 525

Asp His His His His His His
    530                 535

<210> SEQ ID NO 37
<211> LENGTH: 478
<212> TYPE: PRT
<213> ORGANISM: Artificial Sequence
<220> FEATURE:
<223> OTHER INFORMATION: SAPNA sequence

<400> SEQUENCE: 37

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
```

```
                65                  70                  75                  80
Leu Asn Thr Val Leu Glu Thr Leu Asp Leu Gln Asp Ala Val Leu Val
                    85                  90                  95
Gly Phe Ser Met Gly Thr Gly Glu Val Ala Arg Tyr Val Ser Ser Tyr
                100                 105                 110
Gly Thr Ala Arg Ile Ala Ala Val Ala Phe Leu Ala Ser Leu Glu Pro
                115                 120                 125
Phe Leu Leu Lys Thr Asp Asp Asn Pro Asp Gly Ala Ala Pro Gln Glu
            130                 135                 140
Phe Phe Asp Gly Ile Val Ala Ala Val Lys Ala Asp Arg Tyr Ala Phe
145                 150                 155                 160
Tyr Thr Gly Phe Phe Asn Asp Phe Tyr Asn Leu Asp Glu Asn Leu Gly
                165                 170                 175
Thr Arg Ile Ser Glu Glu Ala Val Arg Asn Ser Trp Asn Thr Ala Ala
                180                 185                 190
Ser Gly Gly Phe Phe Ala Ala Ala Ala Pro Thr Thr Trp Tyr Thr
            195                 200                 205
Asp Phe Arg Ala Asp Ile Pro Arg Ile Asp Val Pro Ala Leu Ile Leu
210                 215                 220
His Gly Thr Gly Asp Arg Thr Leu Pro Ile Glu Asn Thr Ala Arg Val
225                 230                 235                 240
Phe His Lys Ala Leu Pro Ser Ala Glu Tyr Val Glu Val Glu Gly Ala
                245                 250                 255
Pro His Gly Leu Leu Trp Thr His Ala Glu Glu Val Asn Thr Ala Leu
            260                 265                 270
Leu Ala Phe Leu Ala Lys Ala Gln Glu Ala Gln Lys Gln Lys Leu Leu
            275                 280                 285
Thr Glu Val Glu Thr Tyr Val Leu Ser Ile Pro Ser Gly Pro Leu
            290                 295                 300
Lys Ala Glu Ile Ala Gln Arg Leu Glu Asp Val Phe Ala Gly Arg Trp
305                 310                 315                 320
Gly Ser Gly Ala Asp Cys Ala Trp His Leu Gly Glu Leu Val Trp Cys
                325                 330                 335
Thr Ala Gly Ser Gly Trp Glu Asp Leu Glu Val Leu Met Glu Trp Leu
                340                 345                 350
Lys Thr Arg Pro Ile Leu Ser Pro Leu Thr Lys Gly Ile Leu Gly Phe
            355                 360                 365
Val Phe Thr Leu Thr Val Pro Ser Glu Arg Gly Leu Gln Arg Arg
            370                 375                 380
Phe Val Gln Asn Ala Leu Asn Gly Asn Gly Asp Pro Asn Asn Met Asp
385                 390                 395                 400
Lys Ala Val Lys Leu Tyr Arg Lys Leu Lys Arg Glu Ile Thr Phe His
                405                 410                 415
Gly Ala Lys Glu Ile Ser Leu Ser Tyr Ser Ala Gly Ala Leu Ala Ser
            420                 425                 430
Cys Met Gly Leu Ile Tyr Asn Arg Met Gly Ala Val Thr Thr Glu Val
            435                 440                 445
Ala Phe Gly Leu Val Cys Ala Thr Cys Glu Gln Ile Ala Asp Ser Gln
            450                 455                 460
His Arg Ser His Arg Gln Leu Glu His His His His His
465                 470                 475

<210> SEQ ID NO 38
```

<211> LENGTH: 478
<212> TYPE: PRT
<213> ORGANISM: Artificial Sequence
<220> FEATURE:
<223> OTHER INFORMATION: SAPNA sequence

<400> SEQUENCE: 38

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Gly Gly
305                 310                 315                 320

Arg Trp Gly Ala Asp Cys Ala Trp His Leu Gly Glu Leu Val Trp Cys
                325                 330                 335

Thr Ala Gly Trp Glu Gly Gly Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
370                 375                 380

```
Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
            405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
            435                 440                 445

Ala Phe Gly Leu Val Cys Ala Thr Cys Glu Gln Ile Ala Asp Ser Gln
        450                 455                 460

His Arg Ser His Arg Gln Leu Glu His His His His His
465                 470                 475

<210> SEQ ID NO 39
<211> LENGTH: 470
<212> TYPE: PRT
<213> ORGANISM: Artificial Sequence
<220> FEATURE:
<223> OTHER INFORMATION: SAPNA sequence

<400> SEQUENCE: 39

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Gly Ala
                245                 250                 255

Pro His Gly Leu Leu Trp Thr His Ala Glu Glu Val Asn Thr Ala Leu
            260                 265                 270
```

```
Leu Ala Phe Leu Ala Lys Ala Gln Glu Ala Gln Lys Gln Lys Leu Leu
                275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Gly Ala
305                 310                 315                 320

Asp Cys Ala Trp His Leu Gly Glu Leu Val Trp Cys Thr Ala Gly Asp
                325                 330                 335

Leu Glu Val Leu Met Glu Trp Leu Lys Thr Arg Pro Ile Leu Ser Pro
                340                 345                 350

Leu Thr Lys Gly Ile Leu Gly Phe Val Phe Thr Leu Thr Val Pro Ser
                355                 360                 365

Glu Arg Gly Leu Gln Arg Arg Arg Phe Val Gln Asn Ala Leu Asn Gly
                370                 375                 380

Asn Gly Asp Pro Asn Asn Met Asp Lys Ala Val Lys Leu Tyr Arg Lys
385                 390                 395                 400

Leu Lys Arg Glu Ile Thr Phe His Gly Ala Lys Glu Ile Ser Leu Ser
                405                 410                 415

Tyr Ser Ala Gly Ala Leu Ala Ser Cys Met Gly Leu Ile Tyr Asn Arg
                420                 425                 430

Met Gly Ala Val Thr Thr Glu Val Ala Phe Gly Leu Val Cys Ala Thr
                435                 440                 445

Cys Glu Gln Ile Ala Asp Ser Gln His Arg Ser His Arg Gln Leu Glu
450                 455                 460

His His His His His
465                 470

<210> SEQ ID NO 40
<211> LENGTH: 456
<212> TYPE: PRT
<213> ORGANISM: Artificial Sequence
<220> FEATURE:
<223> OTHER INFORMATION: SAPNA sequence

<400> SEQUENCE: 40

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
                35                  40                  45

Asp Ala Gly Tyr Arg Val Ile Thr Tyr Asp Arg Arg Gly Phe Gly Gln
50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
                115                 120                 125

Phe Leu Leu Lys Thr Asp Asp Asn Pro Asp Gly Ala Ala Pro Gln Glu
                130                 135                 140

Phe Phe Asp Gly Ile Val Ala Ala Val Lys Ala Asp Arg Tyr Ala Phe
145                 150                 155                 160
```

```
Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln His Arg Ser His Arg Gln
        435                 440                 445

Leu Glu His His His His His His
    450                 455

<210> SEQ ID NO 41
<211> LENGTH: 13
<212> TYPE: PRT
<213> ORGANISM: Artificial Sequence
<220> FEATURE:
<223> OTHER INFORMATION: Sequence fragments of SAPNX scaffolding protein

<400> SEQUENCE: 41

Asp Cys Ala Trp His Leu Gly Glu Leu Val Trp Cys Thr
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Sequence fragments of SAPNX scaffolding protein
```

```
<400> SEQUENCE: 42

Gly Cys Asp Cys Ala Trp His Leu Gly Glu Leu Val Trp Cys Thr Cys
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: Sequence fragments of SAPNX scaffolding protein

<400> SEQUENCE: 43

Leu Thr Glu Val Glu Thr Tyr Val Leu Ser
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Sequence fragments of SAPNX scaffolding protein

<400> SEQUENCE: 44

Phe Thr Leu Thr Val Pro Ser Glu Arg Gly Leu Gln Arg
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Sequence fragments of SAPNX scaffolding protein

<400> SEQUENCE: 45

Cys Ala Thr Cys Glu Gln Ile Ala Asp
1               5

<210> SEQ ID NO 46
<211> LENGTH: 8
<212> TYPE: PRT
<213> ORGANISM: Artificial Sequence
<220> FEATURE:
<223> OTHER INFORMATION: Sequence fragments of SAPNX scaffolding protein

<400> SEQUENCE: 46

Ala Gln Glu Ala Gln Lys Gln Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Sequence fragments of SAPNX scaffolding protein

<400> SEQUENCE: 47

Tyr Gly Thr Ala Arg
1               5

<210> SEQ ID NO 48
<211> LENGTH: 3
<212> TYPE: PRT
<213> ORGANISM: Artificial Sequence
<220> FEATURE:
<223> OTHER INFORMATION: Sequence fragments of SAPNX scaffolding protein
```

```
<400> SEQUENCE: 48

Thr Asp Asp
1

<210> SEQ ID NO 49
<211> LENGTH: 8
<212> TYPE: PRT
<213> ORGANISM: Artificial Sequence
<220> FEATURE:
<223> OTHER INFORMATION: Sequence fragments of SAPNX scaffolding protein
<220> FEATURE:
<221> NAME/KEY: misc_feature
<222> LOCATION: (2)..(2)
<223> OTHER INFORMATION: Xaa can be any amino acid

<400> SEQUENCE: 49

Leu Xaa Glu Asn Leu Gly Thr Arg
1               5

<210> SEQ ID NO 50
<211> LENGTH: 3
<212> TYPE: PRT
<213> ORGANISM: Artificial Sequence
<220> FEATURE:
<223> OTHER INFORMATION: Sequence fragments of SAPNX scaffolding protein

<400> SEQUENCE: 50

Ile Asp Val
1

<210> SEQ ID NO 51
<211> LENGTH: 5
<212> TYPE: PRT
<213> ORGANISM: Artificial Sequence
<220> FEATURE:
<223> OTHER INFORMATION: Sequence fragments of SAPNX scaffolding protein
<220> FEATURE:
<221> NAME/KEY: misc_feature
<222> LOCATION: (3)..(3)
<223> OTHER INFORMATION: Xaa can be any amino acid

<400> SEQUENCE: 51

Thr Gly Xaa Arg Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Sequence fragments of SAPNX scaffolding protein

<400> SEQUENCE: 52

Glu His His His His His His
1               5

<210> SEQ ID NO 53
<211> LENGTH: 7
<212> TYPE: PRT
<213> ORGANISM: Artificial Sequence
<220> FEATURE:
<223> OTHER INFORMATION: Passenger peptide

<400> SEQUENCE: 53

Leu Val Pro Arg Gly Ser Gly
1               5
```

```
<210> SEQ ID NO 54
<211> LENGTH: 11
<212> TYPE: PRT
<213> ORGANISM: Artificial Sequence
<220> FEATURE:
<223> OTHER INFORMATION: Passenger peptide

<400> SEQUENCE: 54

Gly Ser Glu Asn Leu Tyr Phe Gln Gly Gly Ser
1               5                   10

<210> SEQ ID NO 55
<211> LENGTH: 431
<212> TYPE: PRT
<213> ORGANISM: Artificial Sequence
<220> FEATURE:
<223> OTHER INFORMATION: SAPNX scaffolding protein

<400> SEQUENCE: 55

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Ala Arg Val Ile Thr Tyr Asp Arg Arg Gly Phe Gly Gln
        50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Glu
        130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
                180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
        210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
                260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
        290                 295                 300
```

```
Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Phe Val Gln Asn Ala Leu
        355                 360                 365

Asn Gly Asn Gly Asp Pro Asn Asn Met Asp Lys Ala Val Lys Leu Tyr
        370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
            405                 410                 415

Asn Arg Met Gly Ala Val Thr Thr Glu Val Ala Phe Gly Leu Val
            420                 425                 430

<210> SEQ ID NO 56
<211> LENGTH: 25
<212> TYPE: PRT
<213> ORGANISM: Artificial Sequence
<220> FEATURE:
<223> OTHER INFORMATION: Optional additional segment of SAPNX
      scaffolding protein

<400> SEQUENCE: 56

Cys Ala Thr Cys Glu Gln Ile Ala Asp Ser Gln His Arg Ser His Arg
1               5                   10                  15

Gln Leu Glu His His His His His His
            20                  25

<210> SEQ ID NO 57
<211> LENGTH: 461
<212> TYPE: PRT
<213> ORGANISM: Artificial Sequence
<220> FEATURE:
<223> OTHER INFORMATION: SAPNX sequence comprising exemplary passenger
      peptide

<400> SEQUENCE: 57

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140
```

```
Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
            165                 170                 175

Thr Arg Ile Ser Glu Glu Ala Val Arg Asn Ser Trp Asn Thr Ala Ala
        180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
        210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Gly Ala
            245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Leu Val
290                 295                 300

Pro Arg Gly Ser Gly Pro Leu Lys Ala Glu Ile Ala Gln Arg Leu Glu
305                 310                 315                 320

Asp Val Phe Ala Gly Lys Asn Thr Asp Leu Glu Val Leu Met Glu Trp
                325                 330                 335

Leu Lys Thr Arg Pro Ile Leu Ser Pro Leu Thr Lys Gly Ile Leu Gly
            340                 345                 350

Phe Val Phe Thr Leu Thr Val Pro Ser Glu Arg Gly Leu Gln Arg Arg
        355                 360                 365

Arg Phe Val Gln Asn Ala Leu Asn Gly Asn Gly Asp Pro Asn Asn Met
370                 375                 380

Asp Lys Ala Val Lys Leu Tyr Arg Lys Leu Lys Arg Glu Ile Thr Phe
385                 390                 395                 400

His Gly Ala Lys Glu Ile Ser Leu Ser Tyr Ser Ala Gly Ala Leu Ala
            405                 410                 415

Ser Cys Met Gly Leu Ile Tyr Asn Arg Met Gly Ala Val Thr Thr Glu
            420                 425                 430

Val Ala Phe Gly Leu Val Cys Ala Thr Cys Glu Gln Ile Ala Asp Ser
            435                 440                 445

Gln His Arg Ser His Arg Gln His His His His His
            450                 455                 460

<210> SEQ ID NO 58
<211> LENGTH: 461
<212> TYPE: PRT
<213> ORGANISM: Artificial Sequence
<220> FEATURE:
<223> OTHER INFORMATION: SAPNX sequence comprising exemplary passenger
      peptide

<400> SEQUENCE: 58

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
```

```
          35                  40                  45
Asp Ala Gly Ala Arg Val Ile Thr Tyr Asp Arg Arg Gly Phe Gly Gln
 50                  55                  60

Ser Ser Gln Pro Thr Thr Gly Tyr Asp Tyr Asp Thr Phe Ala Ala Asp
 65                  70                  75                  80

Leu Asn Thr Val Leu Glu Thr Leu Asp Leu Gln Asp Ala Val Leu Val
                 85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
             115                 120                 125

Phe Leu Leu Lys Thr Asp Asp Asn Pro Asp Gly Leu Val Pro Arg Gly
             130                 135                 140

Ser Gly Ala Ala Pro Gln Glu Phe Phe Asp Gly Ile Val Ala Ala Val
145                 150                 155                 160

Lys Ala Asp Arg Tyr Ala Phe Tyr Thr Gly Phe Phe Asn Asp Phe Tyr
                165                 170                 175

Asn Leu Asp Glu Asn Leu Gly Thr Arg Ile Ser Glu Glu Ala Val Arg
            180                 185                 190

Asn Ser Trp Asn Thr Ala Ala Ser Gly Gly Phe Phe Ala Ala Ala Ala
            195                 200                 205

Ala Pro Thr Thr Trp Tyr Thr Asp Phe Arg Ala Asp Ile Pro Arg Ile
        210                 215                 220

Asp Val Pro Ala Leu Ile Leu His Gly Thr Gly Asp Arg Thr Leu Pro
225                 230                 235                 240

Ile Glu Asn Thr Ala Arg Val Phe His Lys Ala Leu Pro Ser Ala Glu
                245                 250                 255

Tyr Val Glu Val Glu Gly Ala Pro His Gly Leu Leu Trp Thr His Ala
            260                 265                 270

Glu Glu Val Asn Thr Ala Leu Leu Ala Phe Leu Ala Lys Ala Gln Glu
            275                 280                 285

Ala Gln Lys Gln Lys Leu Leu Thr Glu Val Glu Thr Tyr Val Leu Ser
        290                 295                 300

Ile Ile Pro Ser Gly Pro Leu Lys Ala Glu Ile Ala Gln Arg Leu Glu
305                 310                 315                 320

Asp Val Phe Ala Gly Lys Asn Thr Asp Leu Glu Val Leu Met Glu Trp
                325                 330                 335

Leu Lys Thr Arg Pro Ile Leu Ser Pro Leu Thr Lys Gly Ile Leu Gly
            340                 345                 350

Phe Val Phe Thr Leu Thr Val Pro Ser Glu Arg Gly Leu Gln Arg Arg
        355                 360                 365

Arg Phe Val Gln Asn Ala Leu Asn Gly Asn Gly Asp Pro Asn Asn Met
        370                 375                 380

Asp Lys Ala Val Lys Leu Tyr Arg Lys Leu Lys Arg Glu Ile Thr Phe
385                 390                 395                 400

His Gly Ala Lys Glu Ile Ser Leu Ser Tyr Ser Ala Gly Ala Leu Ala
                405                 410                 415

Ser Cys Met Gly Leu Ile Tyr Asn Arg Met Gly Ala Val Thr Thr Glu
            420                 425                 430

Val Ala Phe Gly Leu Val Cys Ala Thr Cys Glu Gln Ile Ala Asp Ser
        435                 440                 445

Gln His Arg Ser His Arg Gln His His His His His
        450                 455                 460
```

```
<210> SEQ ID NO 59
<211> LENGTH: 461
<212> TYPE: PRT
<213> ORGANISM: Artificial Sequence
<220> FEATURE:
<223> OTHER INFORMATION: SAPNX sequence comprising exemplary passenger
      peptide

<400> SEQUENCE: 59

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Leu
                245                 250                 255

Val Pro Arg Gly Ser Gly Ala Pro His Gly Leu Leu Trp Thr His Ala
            260                 265                 270

Glu Glu Val Asn Thr Ala Leu Leu Ala Phe Leu Ala Lys Ala Gln Glu
        275                 280                 285

Ala Gln Lys Gln Lys Leu Leu Thr Glu Val Thr Tyr Val Leu Ser
    290                 295                 300

Ile Ile Pro Ser Gly Pro Leu Lys Ala Glu Ile Ala Gln Arg Leu Glu
305                 310                 315                 320

Asp Val Phe Ala Gly Lys Asn Thr Asp Leu Glu Val Leu Met Glu Trp
                325                 330                 335

Leu Lys Thr Arg Pro Ile Leu Ser Pro Leu Thr Lys Gly Ile Leu Gly
            340                 345                 350

Phe Val Phe Thr Leu Thr Val Pro Ser Glu Arg Gly Leu Gln Arg Arg
```

```
               355                 360                 365
Arg Phe Val Gln Asn Ala Leu Asn Gly Asn Gly Asp Pro Asn Asn Met
        370                 375                 380

Asp Lys Ala Val Lys Leu Tyr Arg Lys Leu Lys Arg Glu Ile Thr Phe
385                 390                 395                 400

His Gly Ala Lys Glu Ile Ser Leu Ser Tyr Ser Ala Gly Ala Leu Ala
                405                 410                 415

Ser Cys Met Gly Leu Ile Tyr Asn Arg Met Gly Ala Val Thr Thr Glu
                420                 425                 430

Val Ala Phe Gly Leu Val Cys Ala Thr Cys Glu Gln Ile Ala Asp Ser
            435                 440                 445

Gln His Arg Ser His Arg Gln His His His His His
        450                 455                 460

<210> SEQ ID NO 60
<211> LENGTH: 462
<212> TYPE: PRT
<213> ORGANISM: Artificial Sequence
<220> FEATURE:
<223> OTHER INFORMATION: SAPNX sequence comprising exemplary passenger
      peptide

<400> SEQUENCE: 60

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
                180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Gly Leu Val Pro Arg Gly Ser Gly Ser Ala
                245                 250                 255
```

-continued

Glu Tyr Val Glu Val Gly Ala Pro His Gly Leu Leu Trp Thr His
            260                 265                 270

Ala Glu Glu Val Asn Thr Ala Leu Leu Ala Phe Leu Ala Lys Ala Gln
        275                 280                 285

Glu Ala Gln Lys Gln Lys Leu Leu Thr Glu Val Glu Thr Tyr Val Leu
    290                 295                 300

Ser Ile Ile Pro Ser Gly Pro Leu Lys Ala Glu Ile Ala Gln Arg Leu
305                 310                 315                 320

Glu Asp Val Phe Ala Gly Lys Asn Thr Asp Leu Glu Val Leu Met Glu
                325                 330                 335

Trp Leu Lys Thr Arg Pro Ile Leu Ser Pro Leu Thr Lys Gly Ile Leu
            340                 345                 350

Gly Phe Val Phe Thr Leu Thr Val Pro Ser Glu Arg Gly Leu Gln Arg
        355                 360                 365

Arg Arg Phe Val Gln Asn Ala Leu Asn Gly Asn Gly Asp Pro Asn Asn
    370                 375                 380

Met Asp Lys Ala Val Lys Leu Tyr Arg Lys Leu Lys Arg Glu Ile Thr
385                 390                 395                 400

Phe His Gly Ala Lys Glu Ile Ser Leu Ser Tyr Ser Ala Gly Ala Leu
                405                 410                 415

Ala Ser Cys Met Gly Leu Ile Tyr Asn Arg Met Gly Ala Val Thr Thr
            420                 425                 430

Glu Val Ala Phe Gly Leu Val Cys Ala Thr Cys Glu Gln Ile Ala Asp
        435                 440                 445

Ser Gln His Arg Ser His Arg Gln His His His His His His
    450                 455                 460

<210> SEQ ID NO 61
<211> LENGTH: 459
<212> TYPE: PRT
<213> ORGANISM: Artificial Sequence
<220> FEATURE:
<223> OTHER INFORMATION: SAPNX sequence comprising exemplary passenger
      peptide

<400> SEQUENCE: 61

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

```
Tyr Thr Gly Phe Phe Asn Asp Phe Tyr Asn Leu Asp Glu Asn Leu Gly
                165                 170                 175
Thr Arg Ile Ser Glu Glu Ala Val Arg Asn Ser Trp Asn Thr Ala Ala
            180                 185                 190
Ser Gly Gly Phe Phe Ala Ala Ala Ala Pro Thr Thr Trp Tyr Thr
        195                 200                 205
Asp Phe Arg Ala Asp Ile Pro Arg Ile Asp Val Pro Ala Leu Ile Leu
    210                 215                 220
His Gly Thr Gly Asp Arg Thr Leu Pro Ile Glu Asn Thr Ala Arg Val
225                 230                 235                 240
Phe His Lys Ala Leu Pro Ser Ala Glu Tyr Val Glu Val Glu Gly Ala
                245                 250                 255
Pro His Gly Leu Leu Trp Thr His Ala Glu Glu Val Asn Thr Ala Leu
            260                 265                 270
Leu Ala Phe Leu Ala Lys Ala Gln Glu Ala Gln Lys Gln Lys Leu Leu
        275                 280                 285
Thr Glu Val Glu Thr Tyr Val Leu Ser Ile Ile Pro Ser Gly Pro Leu
    290                 295                 300
Lys Ala Glu Ile Ala Gln Arg Leu Glu Asp Val Phe Ala Gly Lys Asn
305                 310                 315                 320
Thr Asp Leu Glu Val Leu Met Glu Trp Leu Lys Thr Arg Pro Ile Leu
                325                 330                 335
Ser Pro Leu Thr Lys Gly Ile Leu Gly Phe Val Phe Thr Leu Thr Gly
            340                 345                 350
Leu Val Pro Arg Gly Ser Gly Arg Gly Leu Gln Arg Arg Phe
        355                 360                 365
Val Gln Asn Ala Leu Asn Gly Asn Gly Asp Pro Asn Asn Met Asp Lys
    370                 375                 380
Ala Val Lys Leu Tyr Arg Lys Leu Lys Arg Glu Ile Thr Phe His Gly
385                 390                 395                 400
Ala Lys Glu Ile Ser Leu Ser Tyr Ser Ala Gly Ala Leu Ala Ser Cys
                405                 410                 415
Met Gly Leu Ile Tyr Asn Arg Met Gly Ala Val Thr Thr Glu Val Ala
            420                 425                 430
Phe Gly Leu Val Cys Ala Thr Cys Glu Gln Ile Ala Asp Ser Gln His
        435                 440                 445
Arg Ser His Arg Gln His His His His His
    450                 455

<210> SEQ ID NO 62
<211> LENGTH: 467
<212> TYPE: PRT
<213> ORGANISM: Artificial Sequence
<220> FEATURE:
<223> OTHER INFORMATION: SAPNX sequence comprising exemplary passenger
      peptide

<400> SEQUENCE: 62

Met Pro Phe Ile Thr Val Gly Gln Glu Asn Ser Thr Ser Ile Asp Leu
1               5                   10                  15
Tyr Tyr Glu Asp His Gly Thr Gly Thr Pro Val Val Leu Ile His Gly
                20                  25                  30
Phe Pro Leu Ser Gly His Ser Trp Glu Arg Gln Ser Ala Ala Leu Leu
            35                  40                  45
Asp Ala Gly Ala Arg Val Ile Thr Tyr Asp Arg Arg Gly Phe Gly Gln
```

```
                50                  55                  60
Ser Ser Gln Pro Thr Thr Gly Tyr Asp Tyr Asp Thr Phe Ala Ala Asp
 65                  70                  75                  80

Leu Asn Thr Val Leu Glu Thr Leu Asp Leu Gln Asp Ala Val Leu Val
                 85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
                115                 120                 125

Phe Leu Leu Lys Thr Asp Asp Asn Pro Asp Gly Ala Ala Pro Gln Glu
            130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
                180                 185                 190

Ser Gly Gly Phe Phe Ala Ala Ala Ala Pro Thr Thr Trp Tyr Thr
            195                 200                 205

Asp Phe Arg Ala Asp Ile Pro Arg Ile Asp Val Pro Ala Leu Ile Leu
210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
                260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Gly Ser
            290                 295                 300

Glu Asn Leu Tyr Phe Gln Gly Gly Ser Pro Leu Lys Ala Glu Ile Ala
305                 310                 315                 320

Gln Arg Leu Glu Asp Val Phe Ala Gly Lys Asn Thr Asp Leu Glu Val
                325                 330                 335

Leu Met Glu Trp Leu Lys Thr Arg Pro Ile Leu Ser Pro Leu Thr Lys
            340                 345                 350

Gly Ile Leu Gly Phe Val Phe Thr Leu Thr Val Pro Ser Glu Arg Gly
            355                 360                 365

Leu Gln Arg Arg Arg Phe Val Gln Asn Ala Leu Asn Gly Asn Gly Asp
            370                 375                 380

Pro Asn Asn Met Asp Lys Ala Val Lys Leu Tyr Arg Lys Leu Lys Arg
385                 390                 395                 400

Glu Ile Thr Phe His Gly Ala Lys Glu Ile Ser Leu Ser Tyr Ser Ala
                405                 410                 415

Gly Ala Leu Ala Ser Cys Met Gly Leu Ile Tyr Asn Arg Met Gly Ala
                420                 425                 430

Val Thr Thr Glu Val Ala Phe Gly Leu Val Cys Ala Thr Cys Glu Gln
                435                 440                 445

Ile Ala Asp Ser Gln His Arg Ser His Arg Gln Leu Glu His His His
            450                 455                 460

His His His
465
```

<210> SEQ ID NO 63
<211> LENGTH: 465
<212> TYPE: PRT
<213> ORGANISM: Artificial Sequence
<220> FEATURE:
<223> OTHER INFORMATION: SAPNX sequence comprising exemplary passenger peptide

<400> SEQUENCE: 63

Met Pro Phe Ile Thr Val Gly Gln Glu Asn Ser Thr Ser Ile Asp Leu
1               5                   10                  15

Tyr Tyr Glu Asp His Gly Gly Ser Glu Asn Leu Tyr Phe Gln Gly Gly
            20                  25                  30

Ser Thr Pro Val Val Leu Ile His Gly Phe Pro Leu Ser Gly His Ser
        35                  40                  45

Trp Glu Arg Gln Ser Ala Ala Leu Leu Asp Ala Gly Ala Arg Val Ile
    50                  55                  60

Thr Tyr Asp Arg Arg Gly Phe Gly Gln Ser Ser Gln Pro Thr Thr Gly
65                  70                  75                  80

Tyr Asp Tyr Asp Thr Phe Ala Ala Asp Leu Asn Thr Val Leu Glu Thr
                85                  90                  95

Leu Asp Leu Gln Asp Ala Val Leu Val Gly Phe Ser Met Gly Thr Gly
            100                 105                 110

Glu Val Ala Arg Tyr Val Ser Ser Tyr Gly Thr Ala Arg Ile Ala Ala
        115                 120                 125

Val Ala Phe Leu Ala Ser Leu Glu Pro Phe Leu Leu Lys Thr Asp Asp
    130                 135                 140

Asn Pro Asp Gly Ala Ala Pro Gln Glu Phe Phe Asp Gly Ile Val Ala
145                 150                 155                 160

Ala Val Lys Ala Asp Arg Tyr Ala Phe Tyr Thr Gly Phe Phe Asn Asp
                165                 170                 175

Phe Tyr Asn Leu Asp Glu Asn Leu Gly Thr Arg Ile Ser Glu Glu Ala
            180                 185                 190

Val Arg Asn Ser Trp Asn Thr Ala Ala Ser Gly Gly Phe Phe Ala Ala
        195                 200                 205

Ala Ala Ala Pro Thr Thr Trp Tyr Thr Asp Phe Arg Ala Asp Ile Pro
    210                 215                 220

Arg Ile Asp Val Pro Ala Leu Ile Leu His Gly Thr Gly Asp Arg Thr
225                 230                 235                 240

Leu Pro Ile Glu Asn Thr Ala Arg Val Phe His Lys Ala Leu Pro Ser
                245                 250                 255

Ala Glu Tyr Val Glu Val Glu Gly Ala Pro His Gly Leu Leu Trp Thr
            260                 265                 270

His Ala Glu Glu Val Asn Thr Ala Leu Leu Ala Phe Leu Ala Lys Ala
        275                 280                 285

Gln Glu Ala Gln Lys Gln Lys Leu Leu Thr Glu Val Glu Thr Tyr Val
    290                 295                 300

Leu Ser Ile Ile Pro Ser Gly Pro Leu Lys Ala Glu Ile Ala Gln Arg
305                 310                 315                 320

Leu Glu Asp Val Phe Ala Gly Lys Asn Thr Asp Leu Glu Val Leu Met
                325                 330                 335

Glu Trp Leu Lys Thr Arg Pro Ile Leu Ser Pro Leu Thr Lys Gly Ile
            340                 345                 350

Leu Gly Phe Val Phe Thr Leu Thr Val Pro Ser Glu Arg Gly Leu Gln

```
                355                 360                 365
Arg Arg Arg Phe Val Gln Asn Ala Leu Asn Gly Asn Gly Asp Pro Asn
370                 375                 380

Asn Met Asp Lys Ala Val Lys Leu Tyr Arg Lys Leu Lys Arg Glu Ile
385                 390                 395                 400

Thr Phe His Gly Ala Lys Glu Ile Ser Leu Ser Tyr Ser Ala Gly Ala
                405                 410                 415

Leu Ala Ser Cys Met Gly Leu Ile Tyr Asn Arg Met Gly Ala Val Thr
                420                 425                 430

Thr Glu Val Ala Phe Gly Leu Val Cys Ala Thr Cys Glu Gln Ile Ala
                435                 440                 445

Asp Ser Gln His Arg Ser His Arg Gln Leu Glu His His His His
                450                 455                 460

His
465

<210> SEQ ID NO 64
<211> LENGTH: 431
<212> TYPE: PRT
<213> ORGANISM: Artificial Sequence
<220> FEATURE:
<223> OTHER INFORMATION: SAPNX sequence comprising exemplary passenger
      peptide
<220> FEATURE:
<221> NAME/KEY: misc_feature
<222> LOCATION: (52)..(52)
<223> OTHER INFORMATION: Xaa can be any amino acid

<400> SEQUENCE: 64

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
                20                  25                  30

Phe Pro Leu Ser Gly His Ser Trp Glu Arg Gln Ser Ala Ala Leu Leu
            35                  40                  45

Asp Ala Gly Xaa Arg Val Ile Thr Tyr Asp Arg Arg Gly Phe Gly Gln
50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
                100                 105                 110

Gly Thr Ala Arg Ile Ala Ala Val Ala Phe Leu Ala Ser Leu Glu Pro
            115                 120                 125

Phe Leu Leu Lys Thr Asp Asp Asn Pro Asp Gly Ala Ala Pro Gln Glu
        130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Pro Thr Thr Trp Tyr Thr
        195                 200                 205

Asp Phe Arg Ala Asp Ile Pro Arg Ile Asp Val Pro Ala Leu Ile Leu
210                 215                 220
```

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
            245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
            275                 280                 285

Thr Glu Val Glu Thr Tyr Val Leu Ser Ile Ile Pro Ser Gly Pro Leu
290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
                340                 345                 350

Pro Ser Glu Arg Gly Leu Gln Arg Arg Phe Val Gln Asn Ala Leu
            355                 360                 365

Asn Gly Asn Gly Asp Pro Asn Asn Met Asp Lys Ala Val Lys Leu Tyr
370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val
                420                 425                 430

<210> SEQ ID NO 65
<211> LENGTH: 5
<212> TYPE: PRT
<213> ORGANISM: Artificial Sequence
<220> FEATURE:
<223> OTHER INFORMATION: Passenger peptide
<220> FEATURE:
<221> NAME/KEY: misc_feature
<222> LOCATION: (3)..(3)
<223> OTHER INFORMATION: Xaa can be any amino acid

<400> SEQUENCE: 65

Leu Pro Xaa Thr Gly
1               5

<210> SEQ ID NO 66
<211> LENGTH: 13
<212> TYPE: PRT
<213> ORGANISM: Artificial Sequence
<220> FEATURE:
<223> OTHER INFORMATION: Passenger peptide

<400> SEQUENCE: 66

Ala His Ile Val Met Val Asp Ala Tyr Lys Pro Thr Lys
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Passenger peptide

<400> SEQUENCE: 67

```
Ala Thr His Ile Lys Phe Ser Lys Arg Asp
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Passenger peptide

<400> SEQUENCE: 68

Cys Cys Pro Gly Cys Cys
1               5

<210> SEQ ID NO 69
<211> LENGTH: 23
<212> TYPE: PRT
<213> ORGANISM: Artificial Sequence
<220> FEATURE:
<223> OTHER INFORMATION: Passenger peptide

<400> SEQUENCE: 69

Asp Ile Pro Ala Thr Tyr Glu Phe Thr Asp Gly Lys His Tyr Ile Thr
1               5                   10                  15

Asn Glu Pro Ile Pro Pro Lys
            20

<210> SEQ ID NO 70
<211> LENGTH: 8
<212> TYPE: PRT
<213> ORGANISM: Artificial Sequence
<220> FEATURE:
<223> OTHER INFORMATION: Passenger peptide

<400> SEQUENCE: 70

Asp Leu Tyr Asp Asp Asp Asp Lys
1               5

<210> SEQ ID NO 71
<211> LENGTH: 13
<212> TYPE: PRT
<213> ORGANISM: Artificial Sequence
<220> FEATURE:
<223> OTHER INFORMATION: Passenger peptide

<400> SEQUENCE: 71

Asp Pro Ile Val Met Ile Asp Asn Asp Lys Pro Ile Thr
1               5                   10

<210> SEQ ID NO 72
<211> LENGTH: 8
<212> TYPE: PRT
<213> ORGANISM: Artificial Sequence
<220> FEATURE:
<223> OTHER INFORMATION: Passenger peptide

<400> SEQUENCE: 72

Asp Tyr Lys Asp Asp Asp Asp Lys
1               5

<210> SEQ ID NO 73
<211> LENGTH: 6
<212> TYPE: PRT
<213> ORGANISM: Artificial Sequence
<220> FEATURE:
<223> OTHER INFORMATION: Passenger peptide
```

```
<400> SEQUENCE: 73

Glu Glu Glu Glu Glu Glu
1               5

<210> SEQ ID NO 74
<211> LENGTH: 10
<212> TYPE: PRT
<213> ORGANISM: Artificial Sequence
<220> FEATURE:
<223> OTHER INFORMATION: Passenger peptide

<400> SEQUENCE: 74

Glu Gln Lys Leu Ile Ser Glu Glu Asp Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Passenger peptide

<400> SEQUENCE: 75

Glu Val His Thr Asn Gln Asp Pro Leu Asp
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Passenger peptide

<400> SEQUENCE: 76

Gly Ala Pro Val Pro Tyr Pro Asp Pro Leu Glu Pro Arg
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Passenger peptide

<400> SEQUENCE: 77

Gly Lys Pro Ile Pro Asn Pro Leu Leu Gly Leu Asp Ser Thr
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Passenger peptide

<400> SEQUENCE: 78

Gly Leu Asn Asp Ile Phe Glu Ala Gln Lys Ile Glu Trp His Glu
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Passenger peptide
```

```
<400> SEQUENCE: 79

Lys Glu Thr Ala Ala Ala Lys Phe Glu Arg Gln His Met Asp Ser
1               5                   10                  15

<210> SEQ ID NO 80
<211> LENGTH: 12
<212> TYPE: PRT
<213> ORGANISM: Artificial Sequence
<220> FEATURE:
<223> OTHER INFORMATION: Passenger peptide

<400> SEQUENCE: 80

Lys Leu Gly Asp Ile Glu Phe Ile Lys Val Asn Lys
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Passenger peptide

<400> SEQUENCE: 81

Lys Leu Gly Ser Ile Glu Phe Ile Lys Val Asn Lys
1               5                   10

<210> SEQ ID NO 82
<211> LENGTH: 26
<212> TYPE: PRT
<213> ORGANISM: Artificial Sequence
<220> FEATURE:
<223> OTHER INFORMATION: Passenger peptide

<400> SEQUENCE: 82

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 83
<211> LENGTH: 11
<212> TYPE: PRT
<213> ORGANISM: Artificial Sequence
<220> FEATURE:
<223> OTHER INFORMATION: Passenger peptide

<400> SEQUENCE: 83

Met Ala Ser Met Thr Gly Gly Gln Gln Met Gly
1               5                   10

<210> SEQ ID NO 84
<211> LENGTH: 38
<212> TYPE: PRT
<213> ORGANISM: Artificial Sequence
<220> FEATURE:
<223> OTHER INFORMATION: Passenger peptide

<400> SEQUENCE: 84

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35
```

<210> SEQ ID NO 85
<211> LENGTH: 12
<212> TYPE: PRT
<213> ORGANISM: Artificial Sequence
<220> FEATURE:
<223> OTHER INFORMATION: Passenger peptide

<400> SEQUENCE: 85

Pro Asp Arg Val Arg Ala Val Ser His Trp Ser Ser
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Passenger peptide

<400> SEQUENCE: 86

Ser Leu Ala Glu Leu Leu Asn Ala Gly Leu Gly Gly Ser
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Passenger peptide

<400> SEQUENCE: 87

Ser Arg Leu Glu Glu Glu Leu Arg Arg Arg Leu Thr Glu
1               5                   10

<210> SEQ ID NO 88
<211> LENGTH: 16
<212> TYPE: PRT
<213> ORGANISM: Artificial Sequence
<220> FEATURE:
<223> OTHER INFORMATION: Passenger peptide

<400> SEQUENCE: 88

Thr Asp Lys Asp Met Thr Ile Thr Phe Thr Asn Lys Lys Asp Ala Glu
1               5                   10                  15

<210> SEQ ID NO 89
<211> LENGTH: 9
<212> TYPE: PRT
<213> ORGANISM: Artificial Sequence
<220> FEATURE:
<223> OTHER INFORMATION: Passenger peptide

<400> SEQUENCE: 89

Thr Glu Thr Ser Gln Val Ala Pro Ala
1               5

<210> SEQ ID NO 90
<211> LENGTH: 18
<212> TYPE: PRT
<213> ORGANISM: Artificial Sequence
<220> FEATURE:
<223> OTHER INFORMATION: Passenger peptide

<400> SEQUENCE: 90

Thr Lys Glu Asn Pro Arg Ser Asn Gln Glu Glu Ser Tyr Asp Asp Asn
1               5                   10                  15

Glu Ser

```
<210> SEQ ID NO 91
<211> LENGTH: 8
<212> TYPE: PRT
<213> ORGANISM: Artificial Sequence
<220> FEATURE:
<223> OTHER INFORMATION: Passenger peptide

<400> SEQUENCE: 91

Thr Gln Asp Pro Ser Arg Val Gly
1               5

<210> SEQ ID NO 92
<211> LENGTH: 14
<212> TYPE: PRT
<213> ORGANISM: Artificial Sequence
<220> FEATURE:
<223> OTHER INFORMATION: Passenger peptide

<400> SEQUENCE: 92

Val Pro Thr Ile Val Met Val Asp Ala Tyr Lys Arg Tyr Lys
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Passenger peptide

<400> SEQUENCE: 93

Trp Ser His Pro Gln Phe Glu Lys
1               5

<210> SEQ ID NO 94
<211> LENGTH: 9
<212> TYPE: PRT
<213> ORGANISM: Artificial Sequence
<220> FEATURE:
<223> OTHER INFORMATION: Passenger peptide

<400> SEQUENCE: 94

Tyr Pro Tyr Asp Val Pro Asp Tyr Ala
1               5

<210> SEQ ID NO 95
<211> LENGTH: 11
<212> TYPE: PRT
<213> ORGANISM: Artificial Sequence
<220> FEATURE:
<223> OTHER INFORMATION: Passenger peptide

<400> SEQUENCE: 95

Tyr Thr Asp Ile Glu Met Asn Arg Leu Gly Lys
1               5                   10
```